United States Patent [19]

Erickson et al.

[11] Patent Number: 5,565,005

[45] Date of Patent: Oct. 15, 1996

[54] IMPLANTABLE GROWTH TISSUE STIMULATOR AND METHOD OPERATION

[75] Inventors: John H. Erickson, Plano; John C. Tepper, Carrollton; Ike C. Thacker, Galveston, all of Tex.; Greg Turi, Budd Lake, N.J.; Anthony J. Varrichio, Flanders, N.J.; Arthur A. Pilla, Ridgewood, N.J.; Mark A. Bettin; William C. Brosche, both of Plano, Tex.

[73] Assignee: AMEI Technologies Inc., Wilmington, Del.

[21] Appl. No.: 18,944

[22] Filed: Feb. 17, 1993

Related U.S. Application Data

[63] Continuation-in-part of Ser. No. 839,199, Feb. 20, 1992, abandoned.

[51] Int. Cl.⁶ ..................................................... A61N 1/05
[52] U.S. Cl. ............................................. 607/51; 128/903
[58] Field of Search ..................................... 607/9, 32, 50, 607/51; 128/903

[56] References Cited

U.S. PATENT DOCUMENTS

| | | |
|---|---|---|
| D. 320,659 | 10/1991 | Johansson et al. . |
| D. 353,889 | 12/1994 | Erickson et al. ............ D24/155 |
| 2,067,589 | 1/1937 | Antrim . |
| 2,298,232 | 10/1942 | Remund . |
| 3,055,372 | 9/1962 | Browner . |
| 3,702,755 | 11/1972 | Palmer . |
| 3,745,995 | 7/1973 | Kraus . |
| 3,783,880 | 1/1974 | Kraus . |
| 3,842,841 | 10/1974 | Brighton et al. . |
| 3,874,372 | 4/1975 | LeBon . |
| 3,881,873 | 5/1975 | Klowden . |
| 3,890,953 | 6/1975 | Kraus et al. . |
| 3,892,522 | 7/1975 | Gay, Jr. . |
| 3,914,900 | 10/1975 | Bigelow et al. . |
| 3,915,151 | 10/1975 | Kraus . |
| 3,918,440 | 11/1975 | Kraus . |
| 3,946,762 | 3/1976 | Green . |

(List continued on next page.)

FOREIGN PATENT DOCUMENTS

| | | |
|---|---|---|
| 0305791 | 3/1989 | European Pat. Off. . |
| 0561068 | 9/1993 | European Pat. Off. . |
| 1466730 | 6/1987 | U.S.S.R. . |
| 8302901 | 9/1983 | WIPO . |

OTHER PUBLICATIONS

Brokaw, A. Paul "A Simple Three–Terminal IC Bandgap Reference", 25 Jul. 1977.
Dohrmann, George J. and Rubin, Jonathan M., "Intraoperative Ultrasound Imaging of the Spinal cord: Syringomyelia, Cysts, and Tumors—A Preliminary Report", *Surgical Neurologist*, vol. 18, No. 6, Dec. 1982. pp. 395–399, Little, Brown & Co., Boston Massachusetts.
Saba, Joseph M., "Echo–Encephalography", *Medical Electronics*, Sep.–Oct. 1970, pp. 96–103.
"The Alternate Treatment of Fracture Nounion—Electrical Stimulation to Induce Osteogenesis" Brochure by Zimmer–USA, 1979.

*Primary Examiner*—William E. Kamm
*Assistant Examiner*—Jeffrey R. Jastrzab
*Attorney, Agent, or Firm*—Baker & Botts, L.L.P.

[57] ABSTRACT

A hand-held programmer/monitor (500) for programming and monitoring an implantable tissue growth stimulator (10) is provided. The stimulator (10) includes circuitry (46) for implementing selected operations in response to a down-link signal transmitted by the programmer/monitor (500). The stimulator (10) also includes circuitry (46) for transmitting up-link signals to the programmer/monitor (500). The programmer/monitor (500) includes a control circuit (518) for generating the down-link signal. The control circuit (518) also processes the up-link signal to monitor the status of the implantable tissue growth stimulator (10). The programmer/monitor (500) also includes a transmit/receive circuit (514) for transmitting the down-link signal to and for receiving the up-link signal from the implantable tissue growth stimulator (10). The transmit/receive circuit (514) also couples the up-link signal to the control circuit (518).

39 Claims, 35 Drawing Sheets

U.S. PATENT DOCUMENTS

| | | |
|---|---|---|
| 4,026,304 | 5/1977 | Levy . |
| 4,105,017 | 8/1978 | Ryaby et al. . |
| 4,216,548 | 8/1980 | Kraus . |
| 4,232,679 | 11/1980 | Schulman . |
| 4,237,895 | 12/1980 | Johnson . |
| 4,313,438 | 2/1982 | Greatbatch . |
| 4,314,554 | 2/1982 | Greatbatch . |
| 4,333,469 | 6/1982 | Jeffcoat et al. . |
| 4,344,250 | 8/1982 | Fahlstrom . |
| 4,414,979 | 11/1982 | Hirschorn et al. . |
| 4,432,361 | 2/1984 | Christensen et al. . |
| 4,459,988 | 7/1984 | Dugot . |
| 4,461,300 | 7/1984 | Christensen . |
| 4,467,808 | 8/1984 | Brighton et al. . |
| 4,506,673 | 3/1985 | Bonnell . |
| 4,506,674 | 3/1985 | Brighton et al. . |
| 4,514,865 | 5/1985 | Harris . |
| 4,519,394 | 5/1985 | Black et al. . |
| 4,530,360 | 7/1985 | Durante . |
| 4,535,775 | 8/1985 | Brighton et al. . |
| 4,549,546 | 10/1985 | Kelly et al. . |
| 4,549,547 | 10/1985 | Brighton et al. . |
| 4,550,370 | 10/1985 | Baker . |
| 4,556,051 | 12/1985 | Maurer . |
| 4,561,426 | 12/1985 | Stewart . |
| 4,561,443 | 12/1985 | Hogrefe et al. . |
| 4,598,713 | 7/1986 | Hansjürgens et al. . |
| 4,600,010 | 7/1986 | Dugot . |
| 4,602,638 | 7/1986 | Adams . |
| 4,611,597 | 9/1986 | Kraus . |
| 4,613,937 | 9/1986 | Batty, Jr. . |
| 4,619,264 | 10/1986 | Singh . |
| 4,651,468 | 3/1987 | Martinez et al. . |
| 4,654,574 | 3/1987 | Thaler . |
| 4,665,896 | 5/1987 | LaForge et al. . |
| 4,665,920 | 5/1987 | Campbell . |
| 4,679,560 | 7/1987 | Galbraith . |
| 4,683,896 | 8/1987 | Herbst et al. . |
| 4,781,591 | 11/1988 | Allen . |
| 4,785,244 | 11/1988 | Jin et al. . |
| 4,793,325 | 12/1988 | Cadossi et al. . |
| 4,889,111 | 12/1989 | Ben-Dov . |
| 4,905,671 | 3/1990 | Senge et al. . |
| 4,944,299 | 7/1990 | Silvian . |
| 4,974,114 | 11/1990 | Kammerer . |
| 4,993,413 | 2/1991 | McLeod et al. . |
| 5,000,178 | 3/1991 | Griffith . |
| 5,014,699 | 5/1991 | Pollack et al. . |
| 5,030,236 | 7/1991 | Dean . |
| 5,038,780 | 8/1991 | Boetzkes . |
| 5,056,518 | 10/1991 | Pethica et al. . |
| 5,058,582 | 10/1991 | Thaler . |
| 5,088,488 | 2/1992 | Markowitz et al. . |
| 5,103,806 | 4/1992 | McLeod et al. . |
| 5,137,020 | 8/1992 | Wayne et al. ............... 607/32 X |
| 5,154,172 | 10/1992 | Terry, Jr. et al. . |
| 5,191,880 | 3/1993 | McLeod et al. . |

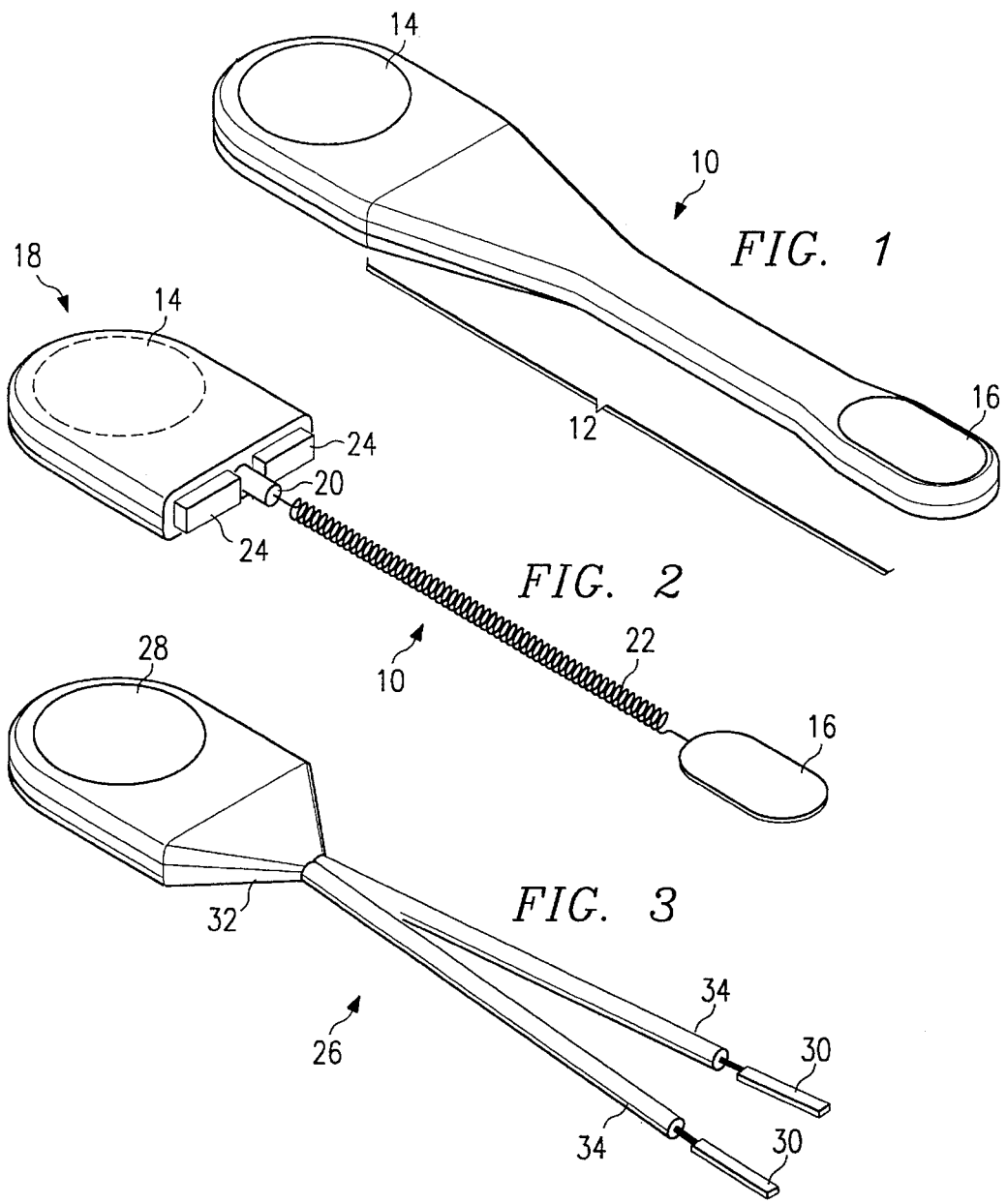
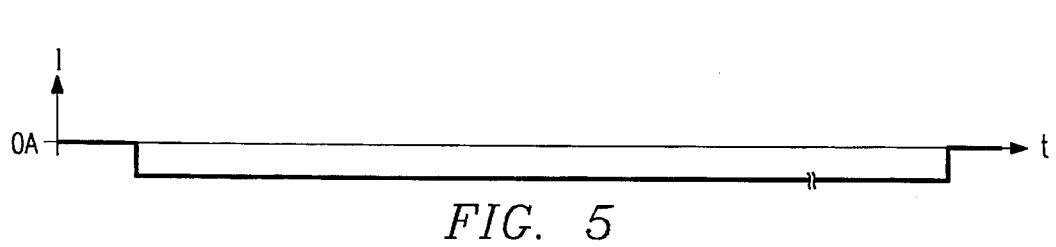

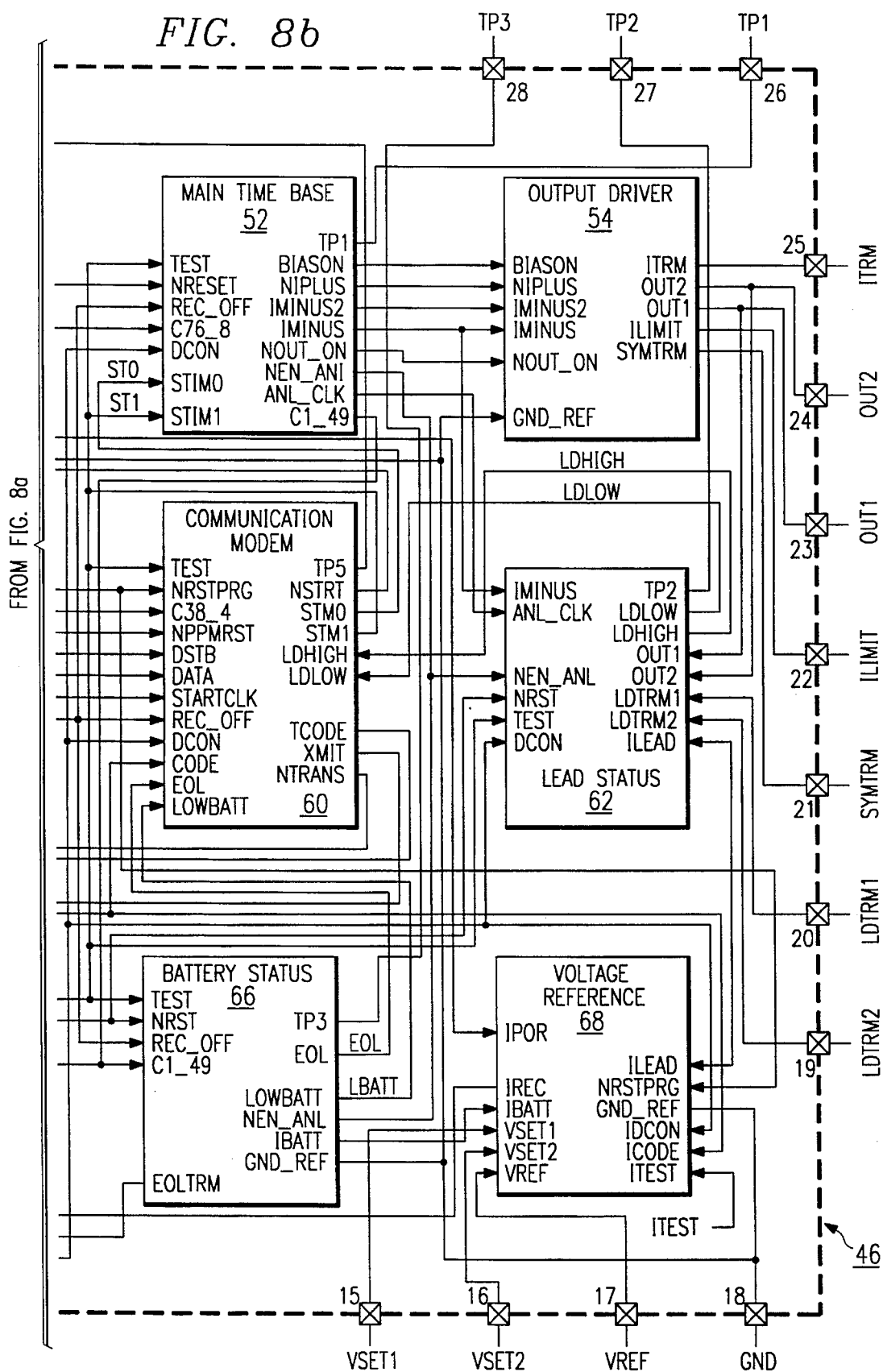

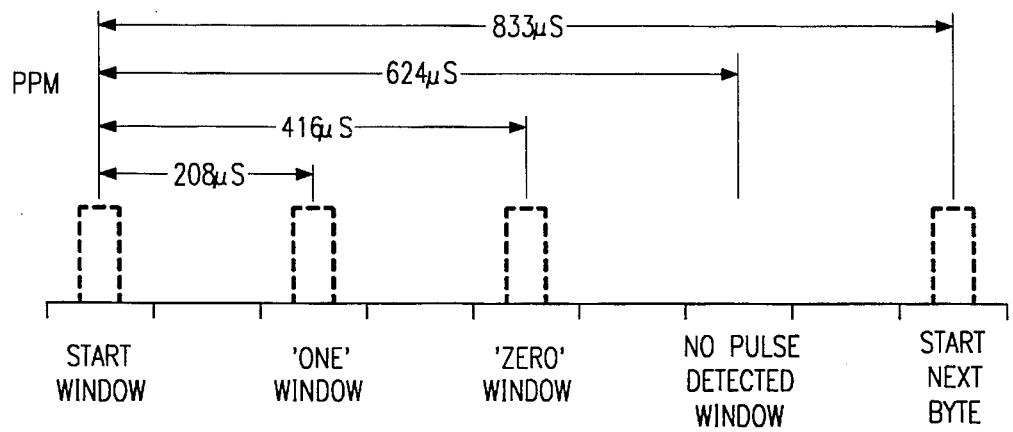

FIG. 9a

DOWN-LINK

| START | RNW | STIM0 | STIM1 | 'ZERO' | 'ONE' | 'ONE' | 'ZERO' | DCON | CODE | STOP |
|---|---|---|---|---|---|---|---|---|---|---|
| | LSB | | | | | | | | MSB | |
| 1 | 0=WRITE<br>1=READ | 0 OFF 0<br>1 4 HOURS 0<br>0 8 HOURS 1<br>1 CONTIN. 1 | | 0 | 1 | 1 | 0 | MUST FOLLOW<br>HARD WIRED<br>CONTROL BITS | | 0 |

FIG. 9b

UP-LINK

| START | STIM0 | STIM1 | DCON | CODE | LEAD0 | LEAD1 | BATT0 | BATT1 | PARITY | STOP |
|---|---|---|---|---|---|---|---|---|---|---|
| | LSB | | | | | | | | MSB | |
| 1 | 0 OFF 0<br>1 4 HOURS 0<br>0 8 HOURS 1<br>1 CONTIN. 1 | | WILL FOLLOW<br>HARD WIRED<br>CONTROL BITS | | 0 LEAD OK 0<br>1 LEAD LOW 0<br>0 LEAD HI 1<br>1 N/A 1 | | 0 BATT OK 0<br>1 LOW BATT 0<br>0 N/A 1<br>1 EOL 1 | | ODD<br>PARITY | 0 |

DC MODE
0 LEADS OK 0
1 LD1 HIGH 0
0 LD2 HIGH 1
1 BOTH HIGH 1

FIG. 9c

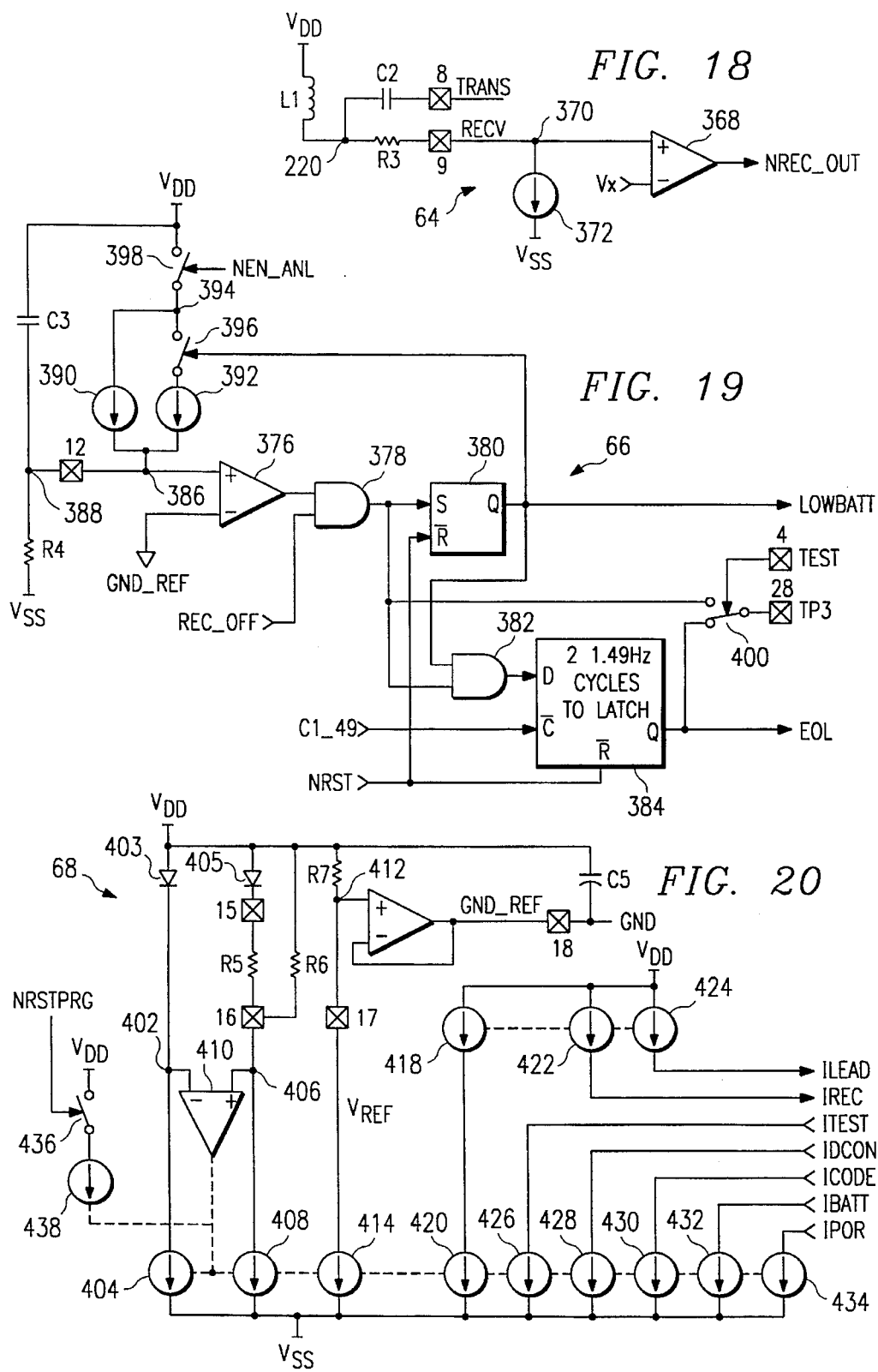

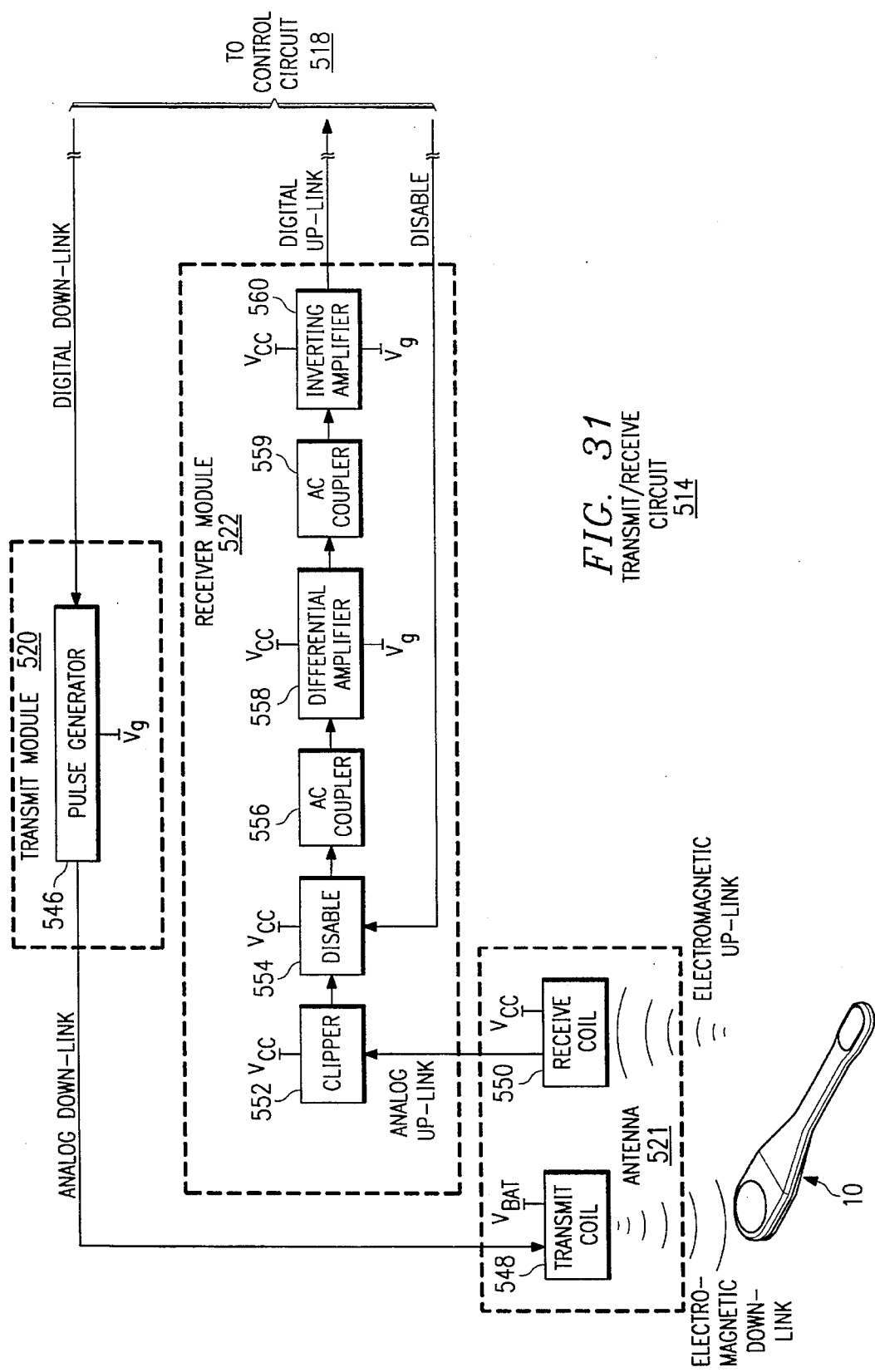

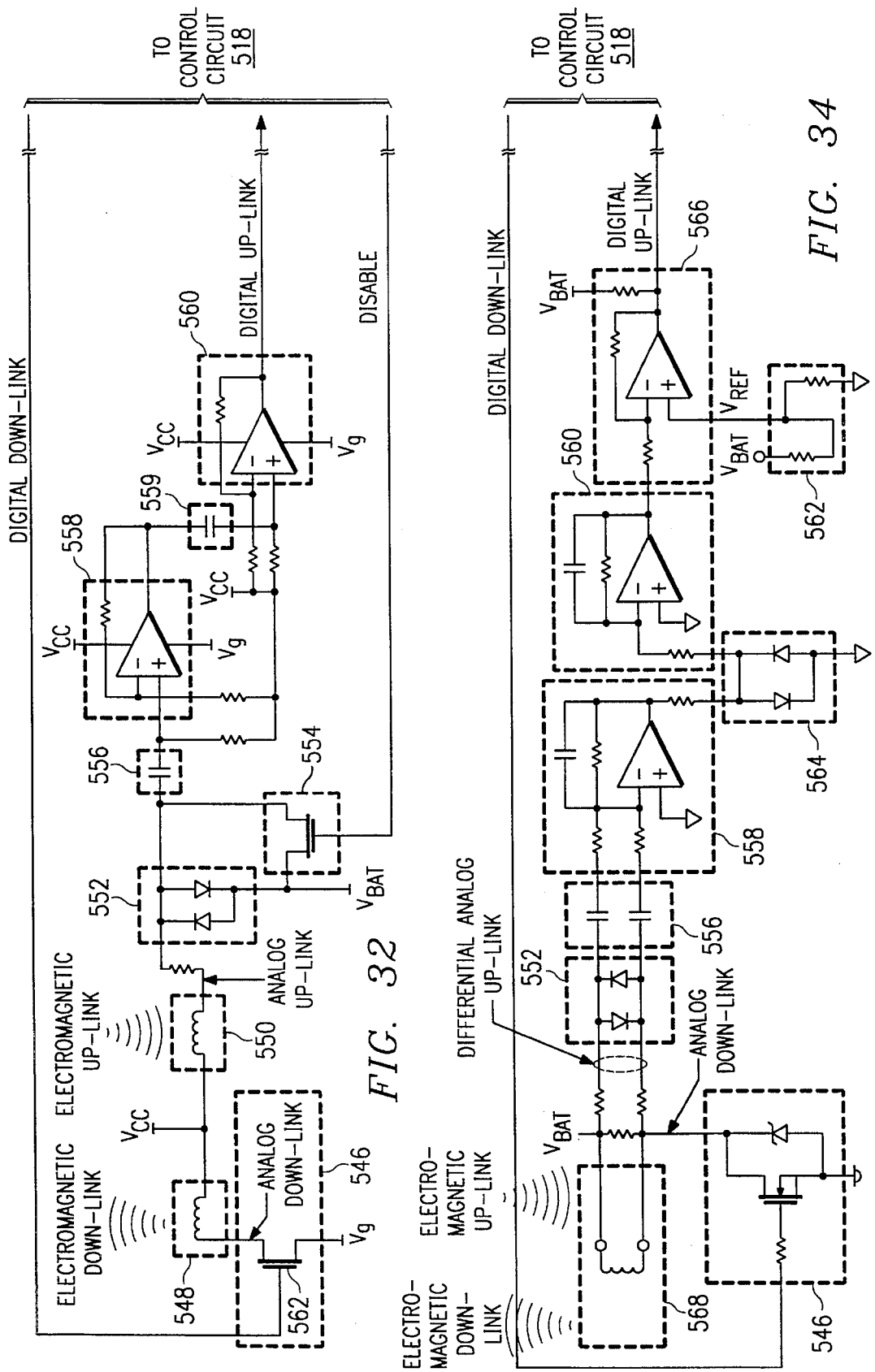

TRANSMIT/RECEIVE CIRCUIT
514

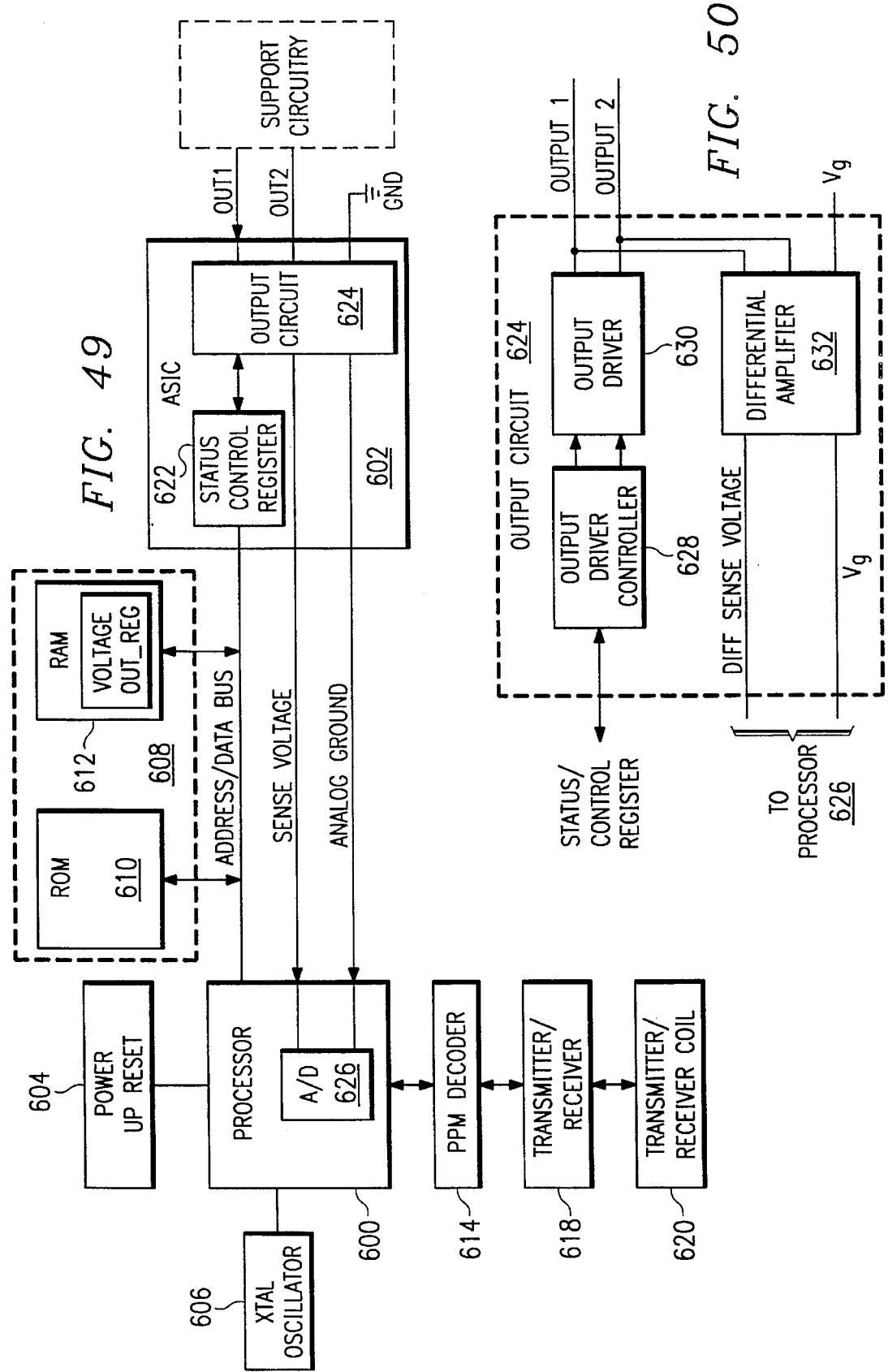

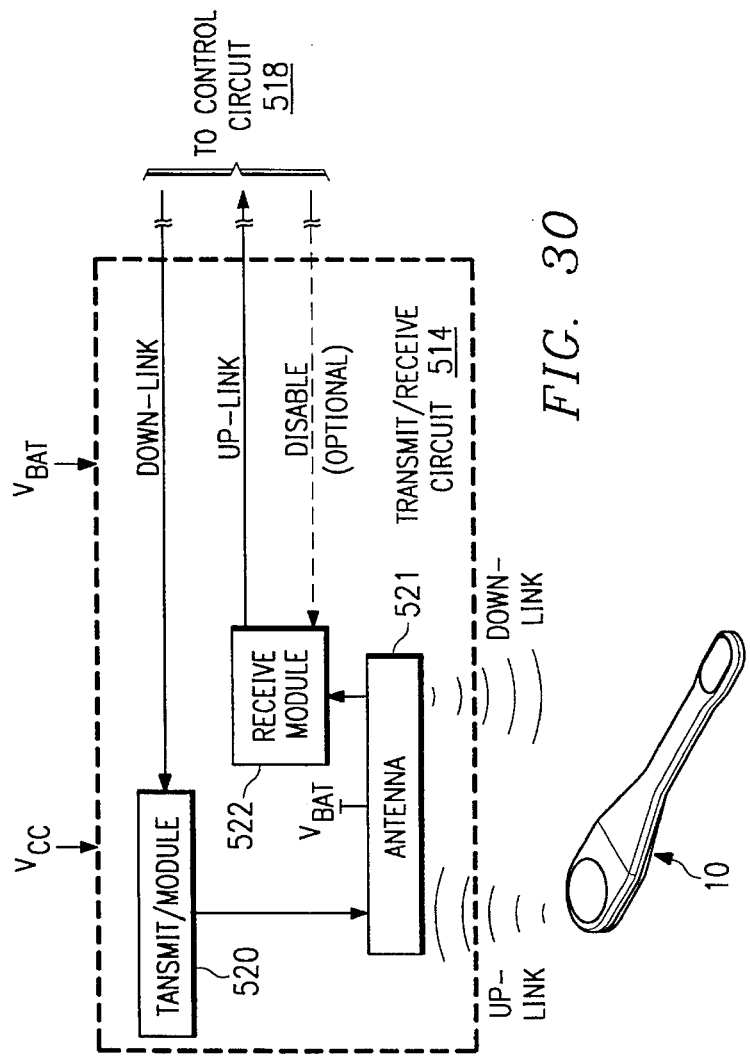

FIG. 52a

MODIFIED DOWN-LINK

| START | RNW | | STIM 0 | STIM 1 | 'ZERO' | 'ONE' | 'ONE' | 'ZERO' | DCON CODE | PARITY | STOP |
|---|---|---|---|---|---|---|---|---|---|---|---|
| | 00 | WRITE | | | | | | | | | |
| | 01 | READ | | | | | | | | | |
| | 10 | WRITE CURRENT | | | | | | | | | |
| | 11 | WRITE DUTY CYCLE | | | | | | | | | |

LSB ←———————————————————————————→ MSB

←——— CURRENT SET ———→
←——— DUTY CYCLE SET ———→

FIG. 52b

UP-LINK2

| START | VOLTAGE_OUT | PARITY | STOP |
|---|---|---|---|

LSB ←———————————————————————————→ MSB

FIG. 52c

UP-LINK3 (AC MODE ONLY)

| START | DUTY_CYCLE | PARITY | STOP |
|---|---|---|---|

LSB ←———————————————————————————→ MSB

IMPLANTABLE GROWTH TISSUE STIMULATOR AND METHOD OPERATION

This application is a continuation-in-part of application Ser. No. 07/839,199 filed Feb. 20, 1992, entitled "IMPLANTABLE BONE GROWTH STIMULATOR AND METHOD OF OPERATION" now abandoned. This application is also related to Design U.S. application Ser. No. 29/004,975 filed Feb. 17, 1993, entitled "IMPLANTABLE GROWTH STIMULATOR", Design U.S. application Ser. No. 29/004,938, filed Feb. 17, 1993, entitled "HAND-HELD PROGRAMMER/MONITOR", U.S. application Ser. No. 08/186,230, filed Jan. 24, 1994, entitled "IMPLANTABLE BONE GROWTH STIMULATOR AND METHOD OF OPERATION", and U.S. application Ser. No. 08/239,401, filed May 5, 1994, entitled "APPARATUS AND METHOD FOR STIMULATING TISSUE GROWTH WITH ULTRASOUND".

TECHNICAL FIELD OF THE INVENTION

This invention relates in general to medical devices, and more particularly to an implantable tissue growth stimulator and method of operation.

BACKGROUND OF THE INVENTION

Known tissue growth stimulators generally fall into at least two broad categories. The first category consists of implantable direct current ("DC") devices. The generator of such stimulators are implanted in the body near the site of tissue damage, a bone fracture or a fusion. A cathode typically exits the case of the DC stimulator leading directly to the injury site. The stimulator case acts as the anode. Electronics within the stimulator cause a direct current to flow between cathode and anode and thereby through the tissue site bone fracture or fusion site generally. A second class of tissue growth stimulators are external or noninvasive stimulators. These stimulators are aligned adjacent to a tissue site, bone fracture or fusion site outside the body. Typically, these devices generate either a pulsed electromagnetic field ("PEMF") or a 60 kHz sinusoidal electric field to promote healing at the injury site. These subgroups of noninvasive stimulators are referred to as PEMF and capacitive coupling stimulators.

There are numerous disadvantages associated with known direct current implantable tissue growth stimulators. In general, the DC characteristics of these stimulators require the leads to be routed directly to the injury site. It is believed that the chemical change at the cathode surface induces tissue growth. Additionally, the cathode (or cathodes) is usually embedded in the tissue, fracture or bone graft mass. It may be required during explant of the stimulator that the implanted cathode be left in the body. This may be necessary after the tissue heals and encapsulates the cathode originally implanted into the tissue mass. If the cathode is damaged, or otherwise becomes inoperative, extensive surgery will be required to replace it at the tissue site. This increases the likelihood of surgical complications such as infection. Also, the DC stimulator and its cathode will degrade imaging results due to their proximity to relevant body structures. Imaging techniques such as magnetic resonance imaging, computer-aided tomography and x-ray photography will all be affected.

External tissue growth stimulators also have disadvantages associated with them. Because of their placement outside the human body, these stimulators are vulnerable from ambulatory or semiambulatory patients. Their movement, whether intentional or inadvertent, may cause damage to the unit. These devices are also cumbersome and usually require the patient to operate them. This creates a question of patient compliance and ultimately of stimulator effectiveness. Furthermore, capacitive coupled stimulators require a conductive gel between the patient's skin and each electrode. This gel must be replaced often and is known to cause skin irritation.

Most known stimulators simply are turned on by the manufacturer and turned off when the stimulator battery dies or the power supply is otherwise disconnected. U.S. Pat. No. 4,414,979 to Hirshorn, entitled "Monitorable Bone Growth Stimulator" issued Nov. 15, 1983, discloses an implantable DC bone growth stimulator which transmits pulses of electromagnetic energy at a rate proportional to the current being delivered to the injury site. This allows some degree of monitorability of the energy delivered to the bone site. However, other parameters of tissue growth stimulators are also of interest. It may be important for the attending physician to know the mode of operation of the stimulator, the expected lifetime of the associated stimulator battery, and the condition of the leads. Conversely, it is also desirable to be able to program certain operating modes of a tissue growth stimulator. Such capability is particularly important with implantable tissue growth stimulators since they are inaccessible otherwise. Such monitorability and programmability have not been available with prior implantable stimulators.

Therefore, a need has arisen for a tissue growth stimulator which is implantable, which is easily replaced and completely removable after use, which is both monitorable and programmable during operation, which does not require patient participation, and which does not interfere with imaging results.

SUMMARY OF THE INVENTION

According to the present invention, a hand-held programmer/monitor for programming and monitoring an implantable tissue growth stimulator is provided. The stimulator includes circuitry for implementing selected operations in response to a down-link signal transmitted by the programmer/monitor. The stimulator also includes circuitry for transmitting up-link signals, representative of the status of the stimulator, to the programmer/monitor. The hand-held programmer/monitor includes a control circuit for generating the down-link signal to program the implantable tissue growth stimulator to perform selected operations. The control circuit also processes the up-link signal to monitor the status of the implantable tissue growth stimulator. The programmer/monitor also includes a transmit/receive circuit for transmitting the down-link signal to the implantable tissue growth stimulator and for receiving the up-link signal from said implantable tissue growth stimulator. The transmit/receive circuit also couples the up-link signal to the control circuit.

A first technical advantage of the present invention is that it can be comfortably held and operated with one hand for an extended period of time.

A second technical advantage of the present invention is that it can program and monitor an implanted stimulator without physical connection thereto.

A third technical advantage of the present invention is that it is self-contained, i.e., it need not be coupled to any external devices for proper operation.

BRIEF DESCRIPTION OF THE DRAWINGS

For a more complete understanding of the present invention, and the advantages thereof, reference is now made to the following descriptions taken in conjunction with the accompanying drawings, in which:

FIGS. 1 and 2 are isometric illustrations of the disclosed tissue growth stimulator configured for generating an alternating current output;

FIG. 3 is an isometric illustration of the disclosed tissue growth stimulator configured for generating a direct current output;

FIG. 4 is a graphical representation of the output of the tissue growth stimulator depicted in FIGS. 1 and 2;

FIG. 5 is a graphical representation of the output of the tissue growth stimulator depicted in FIG. 3;

FIGS. 8a and 8b depict left and right halves of a block diagram of the application specific integrated circuit used in the tissue growth stimulator depicted in FIGS. 1 through 3;

FIG. 9a is a graphical representation of the communication protocol used by the circuit depicted in FIGS. 8a and 8b;

FIGS. 9b and 9c depict tables containing an explanation of the down-link program data word and up-link handshake, respectively, of the circuit depicted in FIGS. 8a and 8b;

FIG. 10 illustrates a block diagram of the crystal oscillator circuit depicted in FIG. 8a;

FIG. 11 illustrates a block diagram of the power on reset circuit depicted in FIG. 8a;

FIG. 14 illustrates schematically the transmitter circuit depicted in FIG. 8a;

FIGS. 15a and 15b illustrate schematically the PPM decoder circuit depicted in FIG. 8a;

FIG. 18 illustrates schematically the receiver circuit depicted in FIG. 8a;

FIG. 19 illustrates schematically the battery status indicator circuit depicted in FIG. 8b;

FIG. 20 illustrates a block diagram of the voltage reference/regulator circuit depicted in FIG. 8b;

FIG. 27 is a block diagram of the block of registers of FIG. 26;

FIG. 28 is a detailed view of the FLAG-REG register of FIG. 27;

FIG. 30 is a block diagram of the transmit/receive circuit of FIG. 24;

FIG. 31 is a block diagram of the preferred embodiment of the transmit/receiver circuit of FIG. 30;

FIG. 32 is a detailed schematic of the preferred alternative embodiment of the transmit/receive circuit of FIG. 31;

FIG. 34 is a detailed schematic of the alternate embodiment of FIG. 33.

FIG. 49 is an alternative embodiment of the circuitry of FIGS. 8a and 8b;

FIG. 50 is a block diagram of the output circuit of FIG. 49;

FIGS. 52a–c are diagrams of the modified DOWN-LINK, UP-LINK2 and UP-LINK3 respectively, as required for the alternate embodiment of FIG. 49.

DETAILED DESCRIPTION OF THE INVENTION

Figure 6:
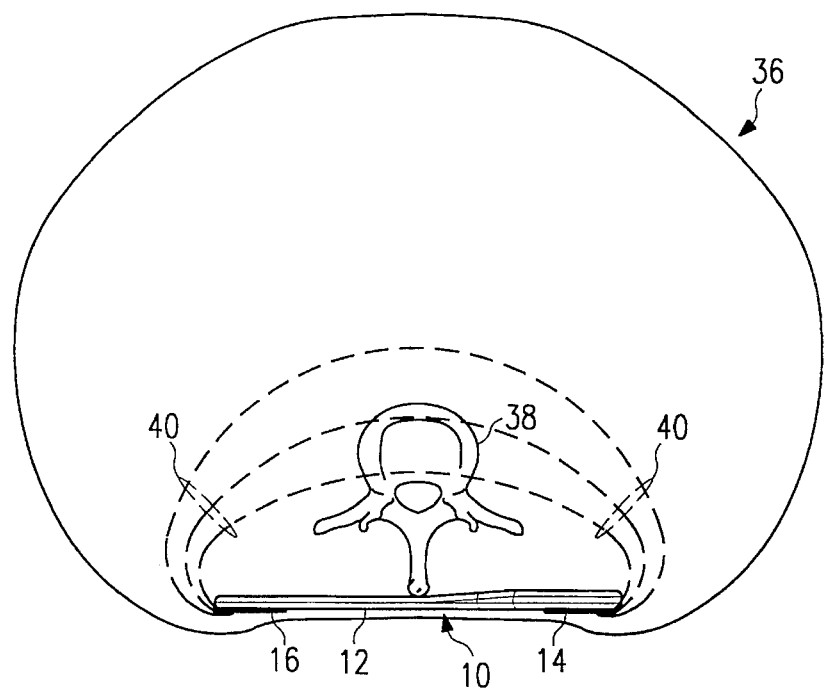
FIG. 6 is a simplified cross-sectional view of the human body depicting one embodiment of an implant configuration for the tissue growth stimulator depicted in FIGS. 1 and 2.

The preferred embodiment of the present invention and its advantages are best understood by referring to FIGS. 1 through 22 of the drawings, like numerals being used for like and corresponding parts of the various drawings.

The present invention will be described in conjunction with the following Table of Contents:

A. MECHANICAL PACKAGING
  1. AC Configuration
  2. DC Configuration
B. OUTPUT CHARACTERISTICS
  1. AC Configuration
  2. DC Configuration
C. IMPLANTATION CONFIGURATION
  1. AC Configuration
  2. DC Configuration
D. ELECTRONIC IMPLEMENTATION
  1. Overview
  2. Communications Protocol
  3. Signal/External Input Description
  4. Circuit Description
    a. Crystal Oscillator
    b. Power-On Reset
    c. Main Time Base
    d. Output Driver
    e. Transmitter
    f. PPM Decoder
    g. Communications Modem
    h. Lead Status
    i. Receiver
    j. Battery Status Indicator
    k. Voltage Reference/Regulator
  5. Stimulator Circuit Configurations
    a. AC Configuration
    b. DC Configuration
E. PROGRAMMER/MONITOR
  1. Circuit Description
    a. Power Circuit
    b. Control Circuit
    c. Transmit/Receive Circuit
      i. Preferred Embodiment
        A. Operation of Preferred Embodiment
      ii. Alternate Embodiment
        A. Operation of Alternative Embodiment
  2. Programming/monitoring of ITGS
F. MODIFIED IMPLANTABLE TISSUE GROWTH STIMULATOR
  1. Circuit Operation
  2. Interactive Programming/Monitoring of Modified Implantable Tissue Growth Stimulator

A. MECHANICAL PACKAGING

1. AC Configuration

FIGS. 1 and 2 are isometric illustrations of the disclosed implantable tissue growth stimulator (ITGS) configured for generating an alternating current output. In particular, FIG. 1 depicts the AC ITGS for implantation into a patient. FIG. 2 depicts the disclosed ITGS prior to final assembly.

FIG. 1 depicts a ITGS configured for an alternating current ("AC") output generally at 10. (Hereinafter the "AC stimulator"). AC ITGS 10 comprises a thin elongate arm 12 made of a flexible elastomeric material connecting a first electrode 14 and a second electrode 16. Arm 12 maintains a predetermined distance between electrodes 14 and 16 while AC ITGS 10 is generally flat. Arm 12, however, flexes allowing AC ITGS 10 to more readily conform to the contours of the patient into which it is surgically implanted.

In the preferred embodiment, arm 12 is fabricated from silicon manufactured by Dow-Corning designated MDX 4-4516. Other implantable grade materials such as urethane and silicon-urethane blends may be used in place of silicon. Electrodes 14 and 16 are manufactured from titanium. Additionally, electrode 14 is an exposed portion of a titanium housing imbedded in AC ITGS 10. (shown in FIG. 2.) The housing is coated with an electrically non-conductive material such as parylene such that no portion of titanium other than electrode 14 is exposed. AC ITGS 10 is approximately 6 inches long and 0.2 inches thick. Approximately 5.5 inches of AC ITGS 10 consists of arm 12. The remaining portion of AC ITGS 10 comprises a coated electronics housing (shown in FIG. 2).

In operation, AC ITGS 10 generates an alternating current between electrodes 14 and 16. The resulting electric field may be used to stimulate tissue and bone healing.

FIG. 2 depicts AC ITGS 10 before arm 12 has been formed and before a non-conducting layer of parylene has been applied to a housing 18. Housing 18 comprises a feed-through assembly 20. Feed-through assembly 20 passes an electrical lead 22 to electrode 16. The dashed line on housing 18 indicates the location of electrode 14 after final assembly. Additionally, housing 18 has two lips 24 which have an irregular surface. Lips 24 thereby facilitate a secure union between arm 12 (shown in FIG. 1) and housing 18.

In one embodiment, housing 18 is manufactured from two clam-shell halves having a length equal to the final length of housing 18. In this first embodiment, the electronics are inserted between the two clam shells and the clam shells are welded together to form a hermetic seal. In the second embodiment, housing 18 is formed from two clam-shell halves which are slightly longer than the final length. These clam shells are welded together initially without the electronic assembly. The end portion is then removed, the electronics are inserted therein and a cap is welded over the opening to form a hermetic seal. In the one embodiment, lead 22 is a helical coil comprised of a medical grade metal alloy such as MP35N.

2. DC Configuration

FIG. 3 depicts an isometric illustration of the disclosed ITGS 26 configured for generating a direct current output (hereinafter the "DC ITGS"). DC ITGS 26 comprises an anode 28 and two cathodes 30. Anode 28 is a quantity of platinum electroplated onto the housing of DC ITGS 26 (shown substantially in FIG. 2). DC ITGS 26 has a short elastomeric arm 32 to better smooth DC ITGS 26 for insertion into the human body and to insulate the feed-through assembly (depicted in FIG. 2). As described in connection with FIGS. 1 and 2, DC ITGS 26 has a titanium housing. It is not coated with a non-conductive material. In addition, cathodes 30 are coupled to electronics within DC ITGS 26 by a coil manufactured from a suitable medical grade metal alloy such as MP35N. Leads 34 are not completely incased in arm 32 so that cathodes 30 may be more easily placed on or within the bone mass to be treated. Leads 34 are sheathed in a tube of elastomeric material.

In operation, DC ITGS 26 generates a DC current between cathodes 30 and anode 28. As will be described in connection with FIGS. 10 through 22, each cathode 30 of DC ITGS is an independent current path.

B. OUTPUT CHARACTERISTICS

1. AC Configuration

FIG. 4 is a graphical representation of the output of the ITGS depicted in FIGS. 1 and 2. AC ITGS 10 (depicted in FIGS. 1 and 2) generates an alternating current output. In the preferred embodiment, AC ITGS 10 generates an asymmetric output of 99 pulses (a "burst") followed by a rest period. After the rest period, the burst/rest cycle is repeated until AC ITGS 10 is turned off. The positive portion of the output pulse, indicated having the duration $t_1$, is approximately 65 µs long and has an amplitude of 2.1 mA. This current generates approximately 3 mV/cm at the healing site in implantation configuration depicted in FIG. 6. The negative portion of the output, indicated having the duration $t_2$, is approximately 195 µs long and has an amplitude of <−0.7 mA. This generates −1 mV/cm at the same healing site. The AC output signal is off after 99 pulses for approximately 640 milliseconds. The resulting burst/rest rate has a frequency of 1.49 Hz.

It should be understood that AC ITGS 10 may be made to output other wave forms, both symmetric and asymmetric. For instance, AC ITGS 10 could produce a wave form having a sinusoidal form. The amplitude of the negative portion of the output may be modified to provide a field strength of 0.3 to 3 mV/cm at the bone or tissue site with corresponding 3× amplitude of the positive side of the waveform. This range produces optimum healing results.

2. DC Configuration

FIG. 5 is a graphical representation of the output of the ITGS depicted in FIG. 3. DC ITGS 26 (shown in FIG. 3) generates a constant negative current between its two cathodes and anode of approximately −20 µA during its operation.

C. IMPLANTATION CONFIGURATION

1. AC Configuration

FIG. 6 is a simplified cross-sectional view of the human body depicting one embodiment of an implant configuration for AC ITGS 10 depicted in FIGS. 1 and 2. AC ITGS selected along its longitudinal axis in a plane generally perpendicular to the planes containing the electrodes 14 and 16. AC ITGS 10 is typically implanted in the human body indicated generally by 36, near a vertebra 38. AC ITGS 10 is placed near vertebra 38 so that the electric field generated between electrodes 14 and 16 is made to penetrate a portion of vertebra 38 in need of bone growth stimulation. The outer limit of the electric field generated by AC ITGS 10 is indicated generally by field lines 40. Vertebra 38 typically is in need of bone growth stimulation when two or more vertebrae are clinically fused together.

Because of the AC nature and the electrode spacing of AC ITGS 10, vertebra 38 will receive the benefit of the electric field 40 even if AC ITGS 10 does not abut vertebra 38. For instance, AC ITGS 10 may be placed further than 1 centimeter away from the injured section of vertebra 38. This allows a surgeon to implant AC ITGS 10 subcutaneously. This simplifies implant and explant, reduces the chance of infection and improves imaging results. Imaging results are improved because there are no foreign objects near vertebra 38.

In the preferred embodiment, AC ITGS 10 is implanted subcutaneously with its electrodes 14 and 16 facing away from vertebra 38. Empirical studies have determined that this placement results in a better electric field distribution and lower inadvertent muscle stimulation.

2. DC Configuration

Figure 7:
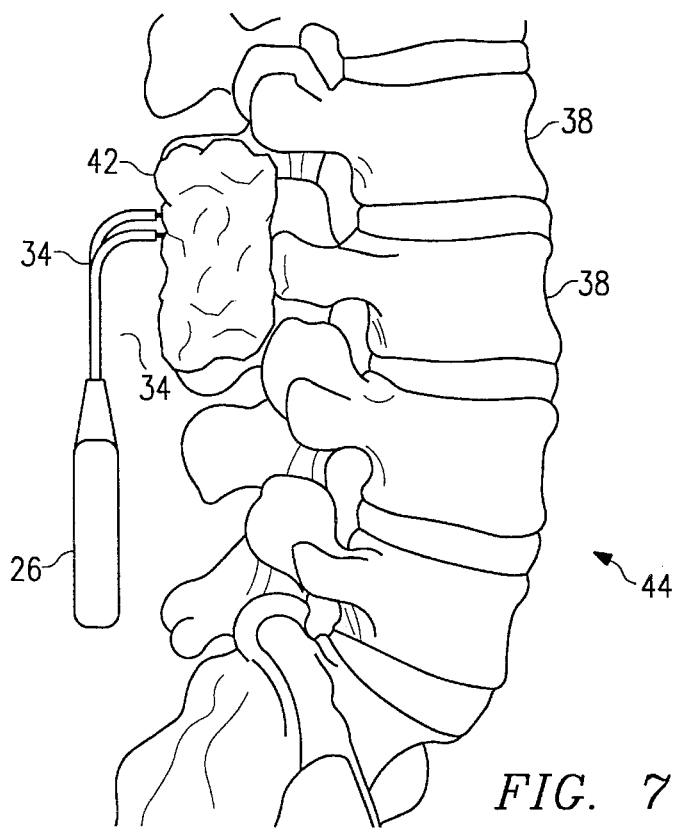
FIG. 7 is a simplified isometric view of the human body depicting one embodiment of an implant configuration for the tissue growth stimulator depicted in FIG. 3.

FIG. 7 is a simplified isometric view of the human body depicting one embodiment of an implant configuration for the DC ITGS 26 depicted in FIG. 3. Here, DC ITGS 26 is used to fuse a bone growth mass 42 to two adjacent vertebrae 38 of spine 44. DC ITGS 26 may be implanted subcutaneously. However, leads 34 must be inserted such that cathodes 30 (not shown) are directly in or adjacent to bone growth mass 42. It is not required that both cathodes 30 be placed at the same bone site.

It should be understood that both AC ITGS 10 and DC ITGS 26 may be implanted near any bone for the repair of several types of bone injuries. Additionally, both AC ITGS 10 and DC ITGS 26 may be implanted near any other type of tissue for repair of several types of tissue injuries. For instance, both AC and DC ITGS may be used to promote bone healing in the long bones of the body in connective tissue (such as cartilage and ligaments), as well as to promote nerve regeneration. Also, both the AC and DC ITGS may be used at a bone site to promote the healing of a bone fracture.

D. ELECTRONIC IMPLEMENTATION

1. Overview

Figure 8A:
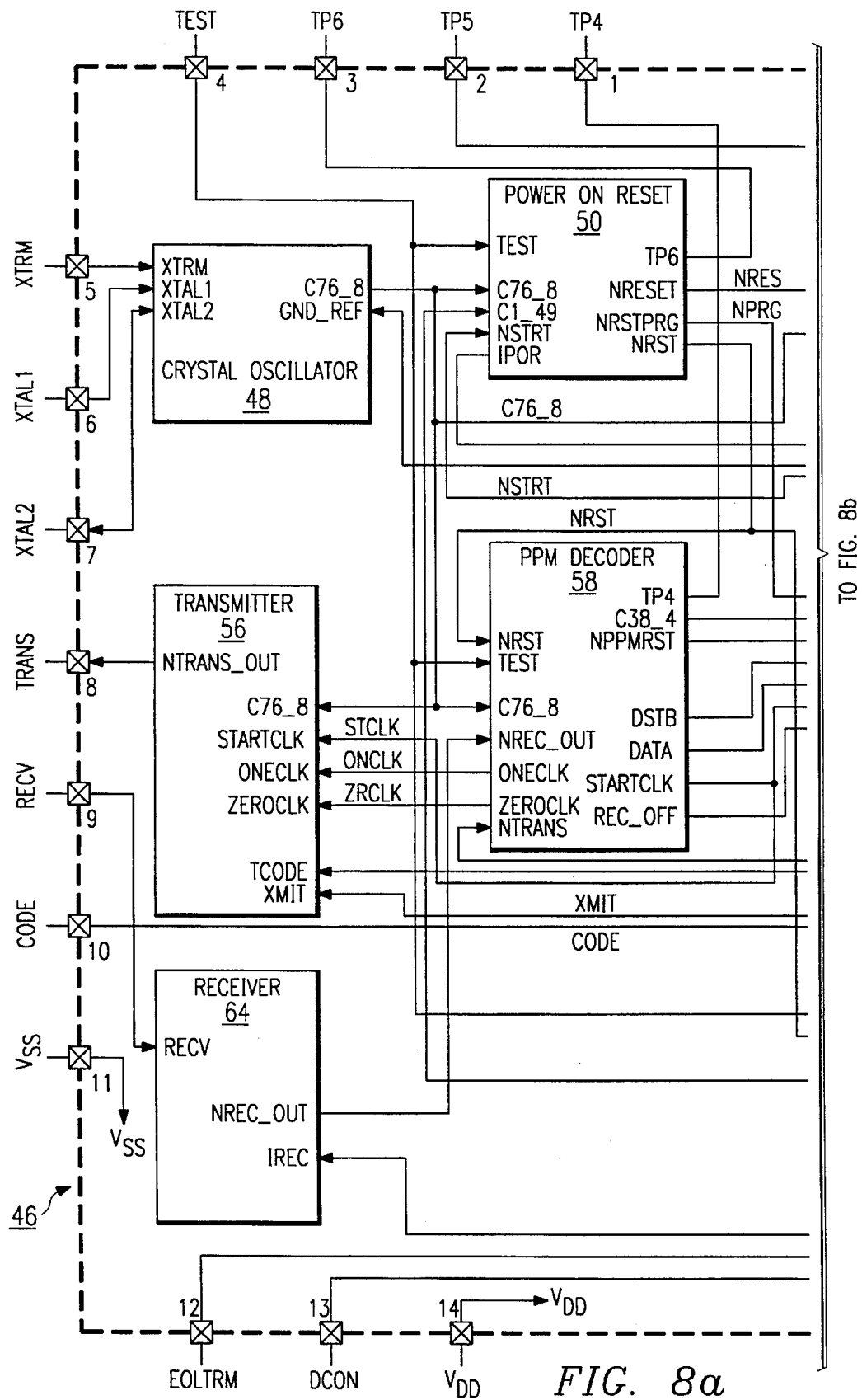

FIGS. 8a and 8b depict left and right halves of a block diagram of the application specific integrated circuit ("ASIC") 46 used in the ITGS depicted in FIGS. 1 through 3. Integrated circuit 46 has 28 external connections, pads 1 through 28. Internally, IC 46 comprises a crystal oscillator circuit 48, a power on reset circuit 50, a main time base circuit 52, an output driver circuit 54, a transmitter circuit 56, a PPM decoder circuit 58, a communication modem circuit 60, a lead status circuit 62, a receiver circuit 64, a battery status circuit 66, and a voltage reference/regulator circuit 68.

Crystal oscillator circuit 48 generates a 76.8 kHz clock signal labeled C76_8. This circuit has three external connections, XTRM, XTAL1, and XTAL2, and one input GND_REF. This circuit is more fully described in connection with FIG. 10.

Power on reset circuit 50 generates three reset outputs, NRESET, NRSTPRG, NRST, to put all other circuits in an initial condition after powering up. This circuit has four inputs, C76_8, C1_49, NSTRT and IPOR, and two test points, TEST and TP6. Power on reset circuit 50 is more fully described in connection with FIG. 11.

Main time base circuit 52 generates the pulse timing signals for control of the output driver circuit 54. In addition, main time base circuit 52 acts as the 24-hour timer for IC 46. This circuit generates 8 outputs, BIASON, NIPLUS, IMINUS, IMINUS2, NOUT_ON, NEN_ANL, ANL_CLK, and C1_49. This circuit has six inputs, NRESET, REC_OFF, C76_8, DCON, STIM0, STIM1, and two test points, TEST and TP1. Main time base circuit 52 is more fully described in connection with FIG. 12.

Output driver circuit 54 controls the output signal, OUT1 and OUT2 delivered to the patient. This circuit has inputs GND_REF, NOUT_ON, IMINUS, IMINUS2, NIPLUS, and BIASON and external connections ILIMIT, ITRM, and SYMTRM. Output driver circuit 54 is more fully described in connection with FIG. 13.

Transmitter circuit 56 combines the pulse timing parameters from PPM decoder 58 with the data output from communication modem 60 to transmit a low frequency magnetic pulse to an external receiver through NTRANS_OUT. This circuit has inputs C76_8, STARTCLK, ONECLK, ZEROCLK, TCODE and XMIT. Transmitter circuit 56 is more fully described in connection with FIG. 14.

PPM decoder circuit 58 determines if received information from receiver circuit 64 is a valid down-link communication. Also, PPM decoder circuit 58 generates the pulse position protocol used by transmitter circuit 56. This circuit has outputs C38_4, NPPMRST, DSTB, DATA, START-CLK, REC_OFF, ZEROCLK, ONECLK. PPM decoder circuit 58 also has inputs C76_8, NREC_OUT, NTRANS, NRST, and 2 test points, TEST and TP4. This circuit is more fully described in connection with FIGS. 15a and 15b.

Communication modem circuit 60 controls the mode of operation of IC 46 through two of its output bits, STIM0 and STIM1. These two bits define the four possible modes of operation: off, four hours on/20 hours off, eight hours on/16 hours off, or continuously on. Also this circuit receives signals from battery status circuit 66 indicating the status of the battery (EOL and LOWBATT) and from lead status circuit 62 indicating the impedance of the output leads (LDHIGH and LDLOW). The circuit then generates an 11-bit communication word and transmit enable (TCODE and XMIT) for transmission by transmitter circuit 56. Communication modem circuit 60 circuit has eleven other inputs, NRSTPRG, C38_4, NPPMRST, DSTB, DATA, START-CLK, REC_OFF, DCON, and CODE, two other outputs, NTRANS and NSTRT, and two test points, TEST and TP5. Communication modem circuit 60 is more fully described in connection with FIG. 16.

Lead status circuit 62 compares the impedance of the output leads with a predetermined threshold or thresholds. It has two outputs, LDLOW and LDHIGH. The circuit has inputs, NRST, IMINUS, ANL_CLK, DCON, NEN_ANL, ILEAD, and connections to OUT1, OUT2, LDTRM1 and LDTRM2, and two test points, TEST and TP2. Lead status circuit 62 is more fully described in connection with FIG. 17.

Receiver circuit 64 generates a digital output, NREC_OUT, from an analog input RECV. This signal is received from a device external to IC 46. Receiver circuit 64 has an additional input IREC. This circuit is more fully described in connection with FIG. 18.

Battery status circuit 66 monitors the voltage supplied by the associated battery and signals the communication modem circuit 60 when the battery reaches two trip points with LOWBATT and EOL. This circuit has inputs, NRST, REC_OFF, C1_49, NEN_ANL, IBATT, and GND_REF, an external connection to EOLTRM and two test points, TEST and TP3. Battery status circuit 66 is more fully described in connection with FIG. 19.

Voltage reference/regulator circuit 68 generates the bias currents used in IC 46: IPOR, IREC, IBATT, ILEAD, IDCON, ICODE, and ITEST. This circuit has inputs NRST-PRG, VSET1, VSET2, and VREF and output GND_REF. Voltage reference regulator circuit 68 is more fully described in connection with FIG. 20.

2. Communications Protocol

FIG. 9a is a graphical representation of the communication protocol used by the circuit depicted in FIGS. 8a and 8b. Integrated circuit 46 transmits and receives data at 1200 Hz. This rate results in a 833 µs overall transmission window. After receiving a start pulse at the start window, integrated circuit 46 looks for the presence or absence of a data pulse in the "one window," "zero window" or "no pulse detected window." As depicted, these three data windows occur approximately 208 µsec, 416 µsec, and 624 µsec after the start pulse. The communication protocol results in a data logic level one if a pulse is received in the one window and a data value zero if a pulse is received in the zero window. A communications error is indicated if a pulse is received in the no pulse detected window. The disclosed communications protocol permits additional error checking by requiring a pulse at both start windows and requiring one but not both of the one window and zero window to have a data value. Each window is approximately 104 µs long. Data detection is enabled only in the four windows described above during each communication.

An external receiver/transmitter may be fabricated from a microprocessor with 1200 Baud capability connected to a suitable coil.

FIGS. 9b and 9c depict tables containing an explanation of the down-link program data word and up-link handshake respectively of the circuit depicted in FIGS. 8a and 8b. Integrated circuit 46 uses an 11 bit program data word. The down-link, or received data word comprises three programmable data bits. The second, third, and fourth bits of the down link program data word contain data which is used by integrated circuit 46 to adjust its mode of operation. Bit 2 is a read-not write (RNW) bit. When RNW equals zero, IC 46 acts upon the third and fourth bits as subsequently described. If RNW equals one, then IC 46 will simply up-link an 11 bit program data word to the external transmitter/receiver. The third and fourth bits, STIM0 and STIM1 indicate how long the ITGS runs. As depicted in FIG. 9a, the bone growth stimulator has four modes of operation. (1) It may be continuously off. (2) It may be on 4 hours, off 20 hours. (3) It may be on 8 hours, off 16 hours. (4) It may operate continuously. All other bits in the down link program data word do not vary. The first, sixth, and seventh bits must be a logic 1 while the fifth, eighth, and eleventh bits must be a 0. The ninth and tenth bits must follow the hard-wired control bits DCON and CODE respectively. DCON is an externally hard-wired bit indicating whether the ITGS is configured for AC or DC output. A logical level of 0 indicates an AC output while a logic level of 1 indicates a DC output. CODE is an externally hard-wired input bit. It may be used, for instance, to indicate a first and second version of manufactured stimulators. The down-link program data word is transmitted left to right.

The up-link program data word transmitted from integrated circuit 46 to an external receiver has 8 bits of data, an odd parity check, and start and stop bits. The start and stop bits are logic high and low respectively. The second and third bits indicate the present mode of operation of IC 46 as described in connection with the down-link program data word. The fourth and fifth bits indicate whether the DCON or CODEs bits are high or low. The sixth and seventh bits indicate the status of the stimulator leads. In the AC mode, these bits indicate whether electrode 16 (shown in FIGS. 1 and 2) is normal, has a low impedance or has a high impedance. In the DC mode, these bits indicate whether either of leads 34 (shown in FIG. 3) has an abnormally high impedance. The particular logic values for each condition in each mode is defined in this FIGURE. The eighth and ninth bits indicate the status of the internal battery of the ITGS. The battery status circuitry 66 (depicted in FIG. 8) monitors the battery voltage for two trip points, 2.1 V and 2.4 V. These voltages correspond to the end of life (EOL) and low battery (LOWBATT) as indicated in the FIGURE. The tenth data bit is an odd parity check bit. It is high when the number of ones preceding it is even and it is low when the number of ones preceding it is odd.

3. Signal/External Input Description

The following signals are used by integrated circuit 46 internally and as external connections:

ANL_CLK is generated by main time base circuit 52. It enables lead status circuit 62 during certain intervals of the DC output signal.

BIASON is generated by the main time base circuit 52. In the AC mode, it turns on the bias current for the positive portion of the output signal. It is disabled during the negative portion of the AC signal output. In the DC mode, it is continuously high. BIASON is used by the output driver.

C1_49 is generated by main time-base circuit 52. It is a clock signal of 1.49 Hz. It is used as a gating signal for the control logic of the output switches of output driver 54.

C76_8 is generated by crystal oscillator circuit 48. It is a clock signal of 76.8 kHz. It is the main time signal used by integrated circuit 46.

CODE is an externally hardwired input bit (Pad 10). The communication protocol requires that communication words have a matching bit for a valid downlink.

DATA is generated by PPM decoder block 58. It is the output from the PPM decoder indicating a valid data 0 or data 1 received from receiver circuit 64.

DCON is an externally hardwired bit (Pad 13). It is used to indicate for which configuration, AC or DC, the circuit is set up. A logic level of 0 indicates the AC configuration while logic level 1 indicates DC configuration.

DSTB is generated by PPM decoder circuit 58. It strobes valid data into communication modem circuit 60.

EOL is generated by battery status circuit 66. This bit will have a logic value of 1 when the battery voltage is less than or equal to 2.1 V. Otherwise it will have a logic value of 0.

EOLTRM is an input to battery status circuit 66. It is coupled to $V_{DD}$ through an external capacitor and resistor (Pad 12). It is used to trim the low battery and end of life voltages to the desired trip points (here, 2.4 and 2.1 V respectively).

GND_REF is generated by voltage reference/regulator circuit 68. It is a buffered voltage level, 1.5 V less than $V_{DD}$. It is brought off-chip through pad 18.

IBATT is generated by voltage reference regulator circuit 68. It produces a 20 nA current sink used to establish the bias current in battery status circuit 66.

ICODE is generated by the voltage reference/regulator circuit 68. It produces a 100 nA current sink used to pull down the CODE pin if that pin is left open.

IDCON is generated by voltage reference/regulator circuit 68. It produces a 100 nA current sink used to pull down the DCON pin if that pin is left open.

ILEAD is generated by voltage reference/regulator circuit 68. It is a 20 nA current source used to bias lead status circuit 62.

ILIMIT is an external connection to output driver circuit 54 (Pad 22). In the AC mode, ILIMIT is not used. In the DC mode, ILIMIT is connected to the stimulator housing and acts as the unit anode.

IMINUS is generated by main time base circuit 52. In the AC mode, it switches the negative output portion of the signal. In the DC mode, it switches the output current. It is used by output driver circuit 54.

IMINUS2 is generated by main time base circuit 52. In the AC mode, it is not used. In the DC mode, it switches the output current for OUT2. It is used by output driver circuit 54.

IPOR is generated by voltage reference/regulator 68. It is a 10 nA current sink used to bias the power on reset circuit 50.

IREC is generated by voltage reference/regulator 68. It is a 20 nA current source used by the receiver circuit 64.

ITEST is generated by the voltage reference/regulator 68. It is a 100 nA current sink used to pull down the TEST pin if that pin is not connected.

ITRM is an external connection to $V_{DD}$ through an external resistor (Pad 25). The resistor is used to trim the output current in both the AC and DC modes. It is an input to output driver circuit 54.

LDHIGH is generated by the lead status unit. In the AC mode, a logic level 1 indicates a high lead impedance. In the DC mode, a logic level 1 indicates a high lead impedance for OUT2.

LDLOW is generated by the lead status unit. In the AC mode, a logic level of 1 indicates a low lead impedance. In the DC mode, logic level of 1 indicates a high lead impedance for OUT1.

LDTRM1 is an input to lead status circuit 62. It is coupled to GND_REF through an external resistor (Pad 20). It sets the trip points for lead status circuit 62.

LDTRM2 is an input to lead status circuit 62. It is coupled to GND_REF through two resistors in series (Pad 19). It is used to set the trip points for lead status circuit 62.

LOWBATT is generated in battery status circuit 66. This signal is normally low. When the battery output drops below 2.4 V, this signal switches to logic level 1.

NEN_ANL is generated by main time base unit 52. In the AC mode, this signal enables the battery and lead status circuits during the negative portion of the output signal. Otherwise, these circuits are disabled to conserve power. In the DC mode, this signal enables the battery and lead status circuits once every 1.49 Hz.

NIPLUS is generated by main time base circuit 52. In the AC mode, this signal controls the output switch for the positive portion of the output signal. It is not used in the DC mode.

NOUT_ON is generated by main time base circuit 52. In the AC mode, this signal enables the output driver during the burst period. It is otherwise off. In the DC mode, this signal is on for the duration of the stimulus, i.e., 4 hours, 8 hours, or continuous.

NPPMRST is generated by PPM decoder circuit 58. It is a primary reset for the communication modem circuit 60.

NREC_OUT is generated by the receiver circuit 64. It is a digital representation of the received external input.

NRESET is generated by power on reset circuit 50. It is reset on power up and after a valid downlink/up-link communication. In either case, it returns high after two 76.8 kHz clock cycles.

NRST is generated by power on reset circuit 50. It is reset on power up and after a valid downlink/up-link communication. In either case, it returns to its high state after one 1.49 Hz clock cycle.

NRSTPRG is generated by power on reset circuit 50. It is reset on power up. It returns to its high state after NRST transitions high.

NSTRT is generated by communication modem circuit 60. It initiates a reset after a valid downlink/up-link communication.

NTRANS is generated by communication modem circuit 60. It indicates the completion of a valid downlink communication.

NTRANS OUT is generated by transmitter unit 56. It is the output signal of the driver stage of the transmitter circuit 56. It is connected to an external coil (Pad 8).

ONECLK is generated by PPM decoder circuit 58. It is the decoded clock signal corresponding to the data position for logic level one in the communications protocol.

OUT1 is an output from output driver circuit 54 (Pad 23). In the both the AC and DC modes, this is the output signal.

OUT2 is an output from output driver circuit 54 (Pad 24). In the AC mode, OUT2 is connected to OUT1. In the DC mode, OUT2 is the second independent current path.

REC_OFF is generated by PPM decoder circuit 58. This signal disables the receiver, battery status and output driver circuits during an up-link operation.

RECV is input to receiver unit 64. It is coupled to an external coil (Pad 9).

STARTCLK is generated by PPM decoder circuit 58. It is a decoded clock signal corresponding to the start position in the communications protocol.

STIM0 is generated by communication modem circuit 60. It is used with the STIM1 bit to generate the four stimulation modes (off, on 4 hours, on 8 hours, on continuously).

STIM1 is generated by communication modem circuit 60. It is used with the STIM0 signal to generate the four stimulation modes (off, on 4 hours, on 8 hours, on continuously).

SYMTRM is an input to output driver circuit 54. It may be coupled to GND_REF or $V_{DD}$ through an external resistor (Pad 21). It is used to trim the positive portion of the output current. It is presently not used.

TCODE is generated by communication modem circuit 60. It is the data output sent to transmitter circuit 56 for external transmission.

TEST is a testing signal used in conjunction with TP1 through TP6. It is brought off chip at pad 4. TP1 through TP6 are external test points (Pads 26, 27, 28, 1, 2, and 3 respectively). They output data from the various cell blocks for testing purposes.

$V_{DD}$ is an external connection to the positive terminal of the 2.8 V battery (Pad 14).

$V_{SS}$ is an external connection to the negative terminal of the 2.8 V battery (Pad 11).

VREF is an input to voltage reference/regulator circuit 68. It is coupled to a 1.5 V unbuffered reference voltage (Pad 17).

VSET1 is an input to voltage reference/regulator circuit 68. It is coupled to $V_{DD}$ through two external resistors in series (Pad 15). It is used to trim VREF.

VSET2 is an input to voltage reference/regulator circuit 68. It is coupled to $V_{DD}$ through a resistor (Pad 16). It is also used to trim VREF.

XMIT is generated by communication modem circuit 60. It enables the transmitter output.

XTAL1 is an external connection to one terminal of a 76.8 kHz oscillator/resistor circuit (Pad 6). It is an input to crystal oscillator circuit 48.

XTAL2 is an external connection to one terminal of a 76.8 kHz oscillator/resistor pair (Pad 7). It is an input to crystal oscillator circuit 48.

XTRM is an external connection to $V_{DD}$ through a resistor (Pad 5). It sets the bias current on the 76.8 kHz crystal oscillator.

ZEROCLK is generated by PPM decoder circuit 58. It is the decoded clock signal corresponding to a logic level zero in the communications protocol.

4. Circuit Description a. Crystal Oscillator

Figure 10:
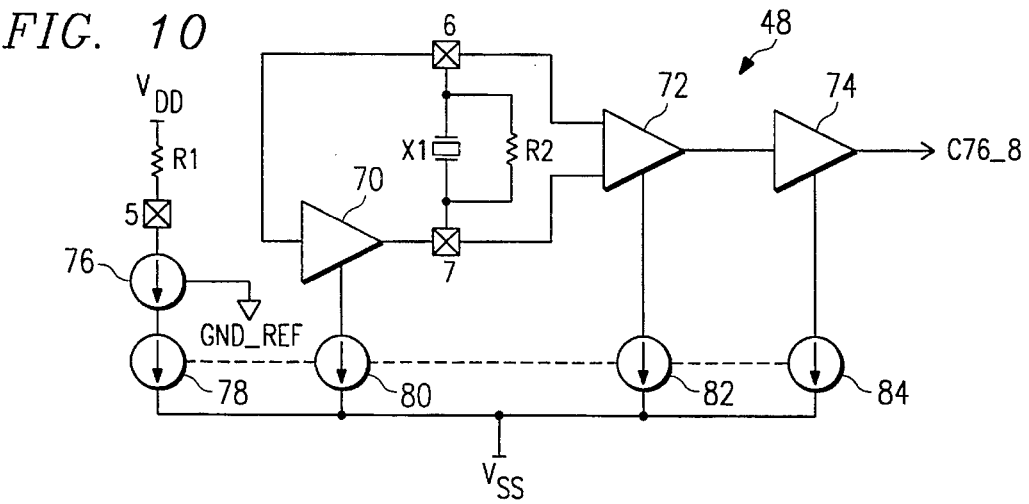

FIG. 10 illustrates a block diagram of the crystal oscillator circuit 48 depicted in FIG. 8*a*. Crystal oscillator circuit 48 comprises a crystal driver 70, a hysteresis comparator 72, and an output driver 74. Crystal driver 70 is connected to crystal X1 and resistor R2 through pads 6 and 7. Crystal X1 and resistor R2 are themselves connected in parallel. The inputs of hysteresis comparator 72 are also coupled to crystal X1 and resistor R2 through pads 6 and 7. The output of hysteresis comparator 72 is connected to output driver 74 which outputs signal C76_8. An external resistor R1 is coupled between $V_{DD}$ and pad 5. Pad 5 is coupled to two current sources 76 and 78 in series. Current source 76 is controlled by the signal GND_REF. Current mirrors 80, 82, and 84 supply the bias current to crystal driver 70, hysteresis comparator 72, and output driver 74, respectively. Each of these current mirrors mirror current source 78 times some integer. This relationship is indicated by the dashed line. In particular, current mirror 80 sources a current five times that of current source 78, current mirror 82 sources three times the amount of current sourced by current source 78 and current mirror 84 sources two times the current of current source 78. Current source 78 and current mirrors 80, 82 and 84 are connected to $V_{SS}$.

In operation, crystal driver 70 applies a voltage across crystal X1 such that crystal X1 oscillates at the regular frequency of 76.8 kHz. Hysteresis comparator 72 toggles if the potential across crystal X1 swings approximately 100 mV. The digital high low output of hysteresis comparator 72 is amplified by output driver 74. Driver 74 ensures that the final signal swings rail to rail ($V_{SS}$ to $V_{DD}$). Resistor R1 in conjunction with GND_REF is used to adjust the bias current mirrors 80, 82, and 84.

b. Power On Reset

Figure 11:
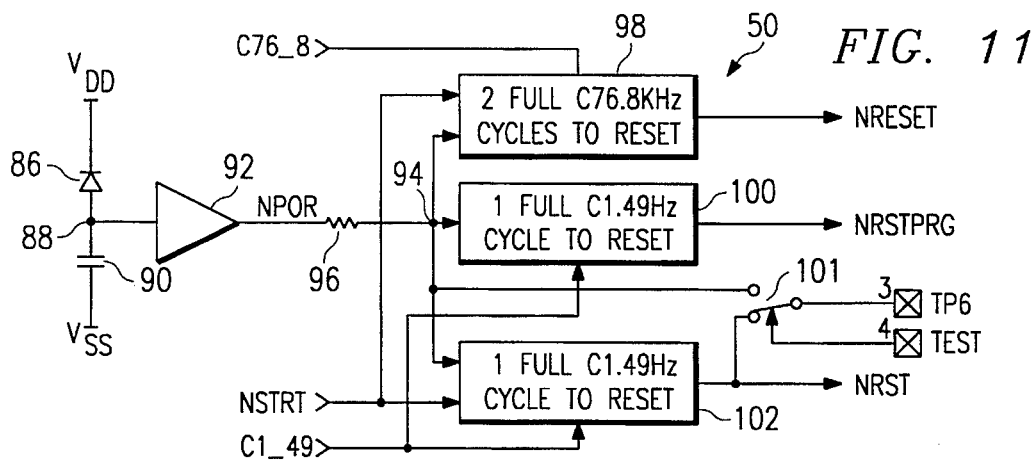

FIG. 11 illustrates a block diagram of the power on reset circuit 50 depicted in FIG. 8*a*. Power on reset circuit 50 comprises a diode 86 connected between $V_{DD}$ and a node 88. Node 88 is coupled to $V_{SS}$ through a capacitor 90. Capacitor 90 may have a capacitance of 6 pF. Node 88 is coupled to the input of a buffer 92. Buffer 92 is coupled to a node 94 through a 10 kOhm resistor 96. Node 94 acts as one input to latches 98, 100, and 102. Latches 98 and 102 are dual reset latches, while latch 100 is a single reset latch. Latch 98 gets set (NRESET goes high) two 76.8 kHz clock cycles after both reset conditions (NPOR, node 94, is low or NSTRT is low) return to logic one. Similarly, latch 102 gets set one 1.49 Hz cycle after both reset conditions go high. Latch 100 gets set one 1.49 Hz cycle after reset condition NPOR goes high. As depicted, the outputs of latches 98, 100, and 102 generate signals NRESET, NRSTPRG, and NRST respectively.

TP6 is connected through pad 3 to either node 94 or NRST. The particular connection is dependant upon the logic level of TEST applied at pad 4. When TEST equals zero, TP6 is connected to NRST. When TEST equals one, TPC is connected to node 94.

In operation, a power drop will cause capacitor 90 to discharge. This will momentarily bring node 88 low. Buffer 92 will reset latches 98, 100, and 102. Latch 98 will return high after two full clock cycles of the clock signal C76_8. Latches 100 and 102 will return high after one cycle of the clock signal C1_49. In addition, latches 98 and 102 may be reset by NSTRT.

During testing, TP6 views the output of slow buffer 92 at node 94 or the output of latch 102. Resistor 96 prevents TP6 from pulling down the output of buffer 92 during testing.

c. Main Time Base

Figure 12:
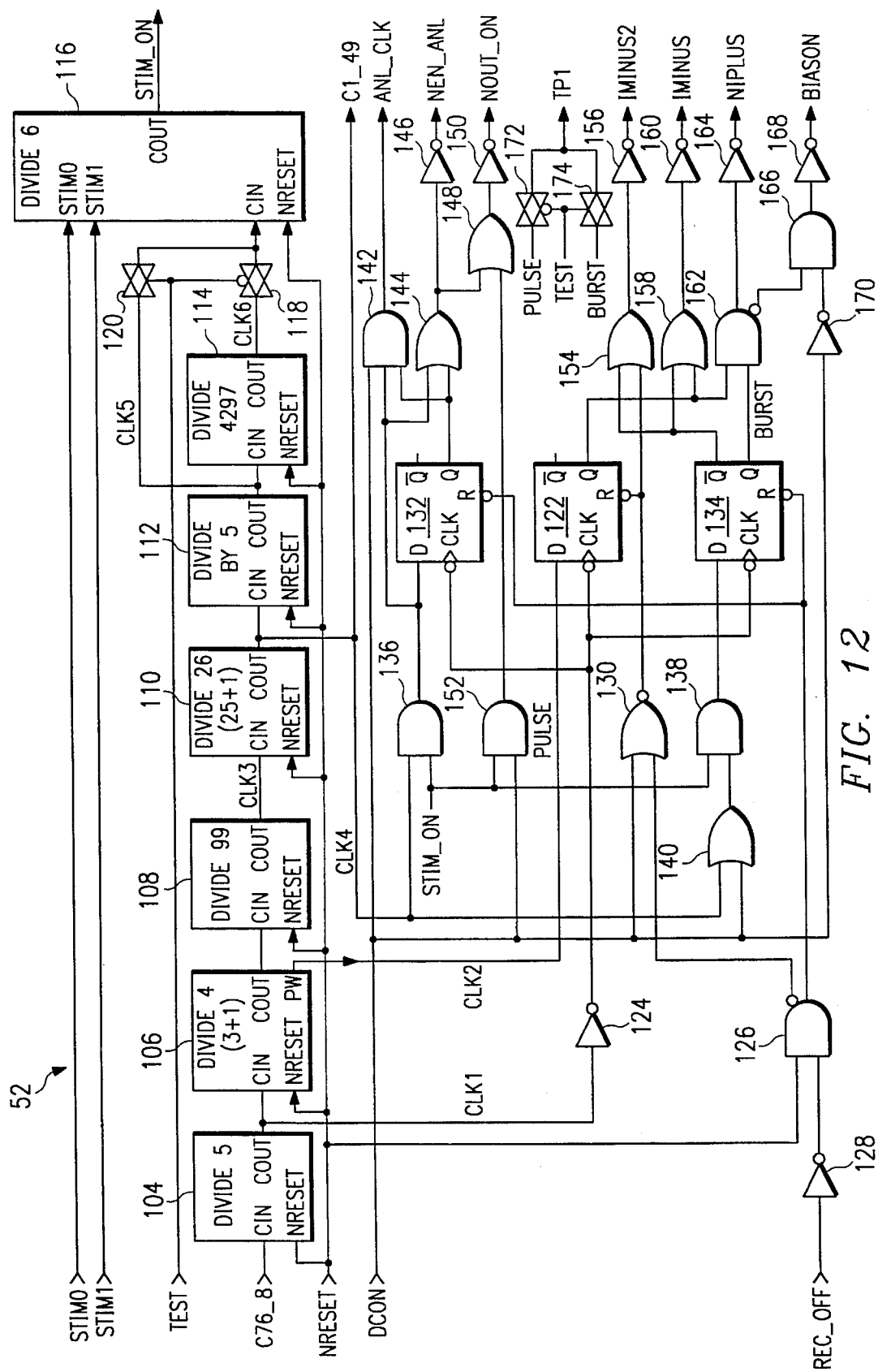
FIG. 12 illustrates schematically the main time base circuit depicted in FIG. 8b.

FIG. 12 illustrates schematically the main time base circuit 52 depicted in FIG. 8b. Main time base circuit 52 generates the clock signals necessary for output driver circuit 54 (shown in FIG. 13). Main time base circuit 52 comprises a series of cascaded divide-by circuits 104, 106, 108, 110, 112, 114, and 116 and various logic gates driven by the divide-by circuits. Each divide-by circuit lowers the frequency of the clock signal input to it by a particular value. Divide-by circuit 104 is a divide-by 5 circuit which has as an input signal C76_8. Divide-by circuit 104 therefore outputs a 15.36 kHz signal. The output of divide-by circuit 104 is connected to the input of divide-by circuit 106. Divide-by circuit 106, a divide-by 4 circuit, generates a 3.84 kHz output. The output of divide-by circuit 106 is connected to the input of divide-by circuit 108. Divide-by circuit 108, a divide-by 99 circuit, generates a 38.8 Hz clock signal. The output of divide-by circuit 108 is input to the divide-by circuit 110. Divide-by circuit 110, a divide-by 26 circuit, generates a 1.49 Hz signal, C1_49. The output of divide-by circuit 110 is input to divide-by circuit 112. Divide-by circuit 112, a divide-by 5 circuit generates a clock signal having a period of 3.35 seconds. The output of divide-by circuit 112 is input to divide-by circuit 114. Divide-by circuit 114, a divide-by 4,297 circuit, generates a clock signal having a period of 4 hours. The output of divide-by circuit 114 is input to divide-by circuit 116 through T-gate 118. Divide-by circuit 116, a divide-by 6 circuit, generates a clock signal having a period of 24 hours. Divide-by circuit 116 may alternately have as its input the output from divide-by circuit 112. The signal, CLK5 may be fed through T-gate 120 as depicted. T-gates 118 and 120 are controlled by TEST. Divide-by circuit 116 also has as its inputs signals STIM0 and STIM1. As depicted, each divide-by circuit 104 through 116 is reset by the signal NRESET.

The control logic of main time base circuit 52 generates the signals ANL_CLK, NEN_ANL, NOUT_ON, IMINUS2, IMINUS, NIPLUS and BIASON as depicted. C1_49 is the output of divide-by circuit 110. The output of divide-by circuit 104 clocks D-type flipflops 122, 132 and 134. The output of divide-by circuit 104 is first inverted by an inverter 124 before clocking flipflop 122. The input of flipflop 122, PULSE, is connected to an alternate output (PW) of divide-by circuit 106. Output PW, labeled CLK2, generates a pulse identical to the output of divide-by circuit 106 occurring on the falling edge of the output of divide-by circuit 106. NRESET and REC_OFF are input to an AND/NAND gate 126 after REC_OFF is inverted by an inverter 128. The NANDed output of gate 126 is combined with DCON by a NOR gate 130. The output of gate 130 is connected to the RESET input of flipflop 122. The ANDed output of gate 126 is connected to the reset input of a D-type flipflops 132 and 134. Flipflop 132 has as its input the output of an AND gate 136. Gate 136 has two inputs, STIM_ON (the output of divide-by circuit 116) and the output from divide-by circuit 110. The input to flipflop 134 is connected to the output of an AND gate 138. Gate 138 has as its two inputs STIM_ON and the output from an OR gate 140. OR gate 140 has two inputs, DCON and the output from divide-by circuit 110.

ANL_CLK is the output from a three input AND gate 142. Gate 142 has inputs DCON, the output of gate 136 and the output of flipflop 132. NEN_ANL is generated from the output of an OR gate 144 inverted by an inverter 146. OR gate 144 has inputs which are the outputs of gate 136 and flipflop 132. NOUT_ON is generated by the output of an OR gate 148 inverted by an inverter 150. Gate 148 has inputs which are the outputs of OR gate 144 and of an AND gate 152. Gate 152 has two inputs STIM_ON and DCON. IMINUS2 is generated from the output of an OR gate 154 inverted by an inverter 156. Gate 154 has inputs which are the outputs of flipflop 134 (inverted) and gate 130. IMINUS is generated from the output of an OR gate 158 inverted by an inverter 160. Gate 158 has inputs which are the outputs of flipflop 134 (inverted) and flipflop 122. NIPLUS is generated from the ANDed output of a dual AND/NAND gate 162 inverted by an inverter 164. Gate 162 has as its inputs the outputs from flipflops 122 and 134. BIASON is generated by the output of an AND gate 166 inverted by inverter 168. Gate 166 has as its input the NANDed output of gate 162 and DCON inverted by an inverter 170.

In addition, T-gates 172 and 174 have their outputs coupled to TP1. The input of T-gates 172 and 174 are coupled to the alternate output, PW, of divide-by circuit 106 and the output of flipflop 134, respectively. T-gates 172 and 174 are controlled by TEST. When TEST equals 0, TP1 is connected to output PW of divide-by circuit 106. When TEST equals 1, TP1 is connected to the output of flipflop 134.

In operation, the output of divide-by circuit 116 (STIM_ON) generates a series of four-hour PULSES depending upon the values of STIM1 and STIM0 according to the following values: If STIM1=0 and STIM0=0, then STIM_ON is low continuously, if STIM1=0 and STIM0=1 then STIM_ON is periodically high for 4 hours and low for 20, if STIM1=1 and STIM0=0, then STIM_ON is periodically high for 8 hours and low for 16, if STIM1=1 and STIM0=1, then STIM_ON is continuously high. This internal signal controls the four modes of operation of the stimulator. The output of divide-by circuit 104 acts as the timing clock for main time base circuit 52. The alternate output, PW, of divide-by circuit 106 generates the 25% high/75% low duty cycle in the AC mode. Divide-by circuit 108 generates 99 PULSES for each burst of the AC signal. Divide-by circuit 110 generates the burst to rest ratio of 1:25. This is the 1.49 Hz output in the AC mode.

The final divide-by operations are split among three divide-by circuits 112, 114 and 116 to facilitate testing. This allows main time base circuit 52 to be tested using an artificial 20-second day. As described above, when TEST=1 the divide-by circuit 114 is bypassed. Also, as described above, the output of divide-by circuit 106 and flipflop 134 may be viewed directly through T-gates 172 and 174 through TP1.

d. Output Driver

Figure 13:
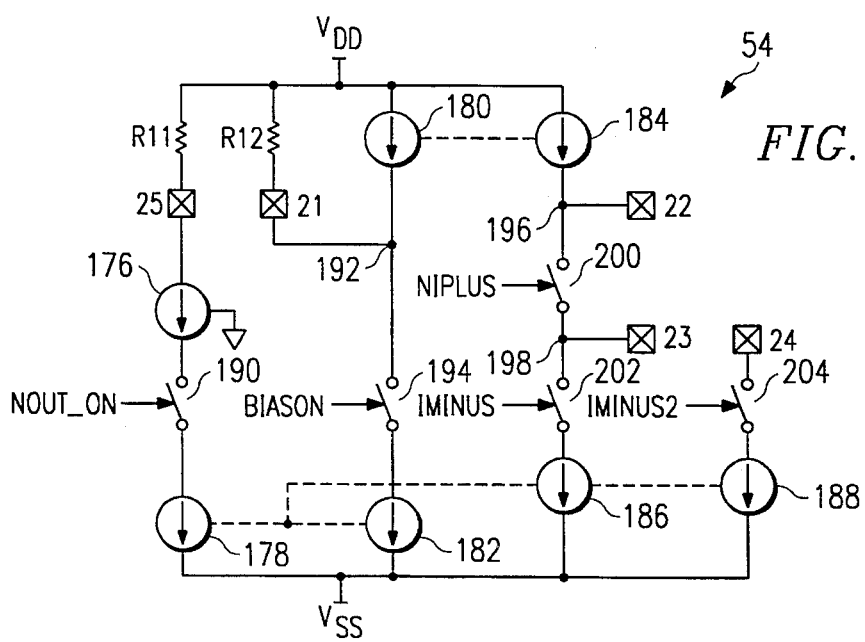
FIG. 13 illustrates a block diagram of the output driver circuit depicted in FIG. 8b.

FIG. 13 illustrates a block diagram of the output driver circuit 54 depicted in FIG. 8b. Output driver 54 comprises current mirrors 176, 178, 180, 182, 184, 186, and 188. Current mirror 176 is connected to $V_{DD}$ through pad 25 and an external resistor R11. Current mirror 176 has a control voltage input, GND_REF. Current mirror 176 is connected to current mirror 178 through a switch 190. Switch 190 is controlled by NOUT_ON. Current mirror 178 mirror is connected between switch 190 and $V_{SS}$. Current mirror 180 is connected between $V_{DD}$ and node 192. Node 192 is connected to $V_{DD}$ also through an optional external resistor R12 at pad 21. Node 192 is also connected to current mirror 182 through a switch 194. Switch 194 is controlled by BIASON. Current mirror 182 is also connected to $V_{SS}$. Current mirror 184 is connected between $V_{DD}$ and a node 196. Node 196 is connected externally to ILIMIT, at pad 22. Node 196 is also coupled to a node 198 through a switch 200. Switch 200 is controlled by NIPLUS. Node 198 is connected externally to OUT1, at pad 23 and to control mirror 186 through a switch 202. Switch 202 is controlled by IMINUS. Control mirror 186 is also connected to $V_{SS}$. A switch 204 is controlled by IMINUS2 and connects an external output, OUT2, at pad 24 to current mirror 188. Current mirror 188 is also connected to $V_{SS}$.

Resistor R11 trims the current through current mirror 176 and hence the current through current mirror 178. Current mirror 182 is designed such that it sinks three times the current of current mirror 178. Current mirrors 186 and 188 are designed such that they sink 33 times the current of current mirror 178. Current mirror 180 sources the same current as current mirror 182 when resistor R12 is omitted. Resistor R12 may be included to trim the current through current mirror 180. Current mirror 184 is designed such that it sources 33 times the current through current mirror 180 or approximately 99 times the current of current mirror 178.

In the AC mode of operation, switch 204 is open allowing OUT2 to be externally connected to OUT1. Simultaneously, switches 200 and 202 are asymmetrically open and closed to periodically source and sink current to OUT1 from current sources 184 and 186. BIASON disables current mirrors 180 and 184 during the negative portion of the output. NOUT_ON enables output drive circuit 54 only during the pulse portion of the output signal. ILIMIT is not used. In this embodiment of output driver circuit 54, the current sourced and sunk from OUT1 is kept at a relatively constant level. In other embodiments, however, the voltage at OUT1 is kept at a constant level.

In the DC mode of operation, ILIMIT is connected to the ITGS housing (depicted in FIG. 2) and acts as the anodes. Switch 200 is open and switch 194 is closed. OUT1 and OUT2 are connected to the 2 cathodes (depicted in FIG. 3) and each is connected to current mirrors 186 and 188, respectively, by switches 202 and 204, respectively. The DC output is controlled by IMINUS and IMINUS2.

e. Transmitter

Figure 14:
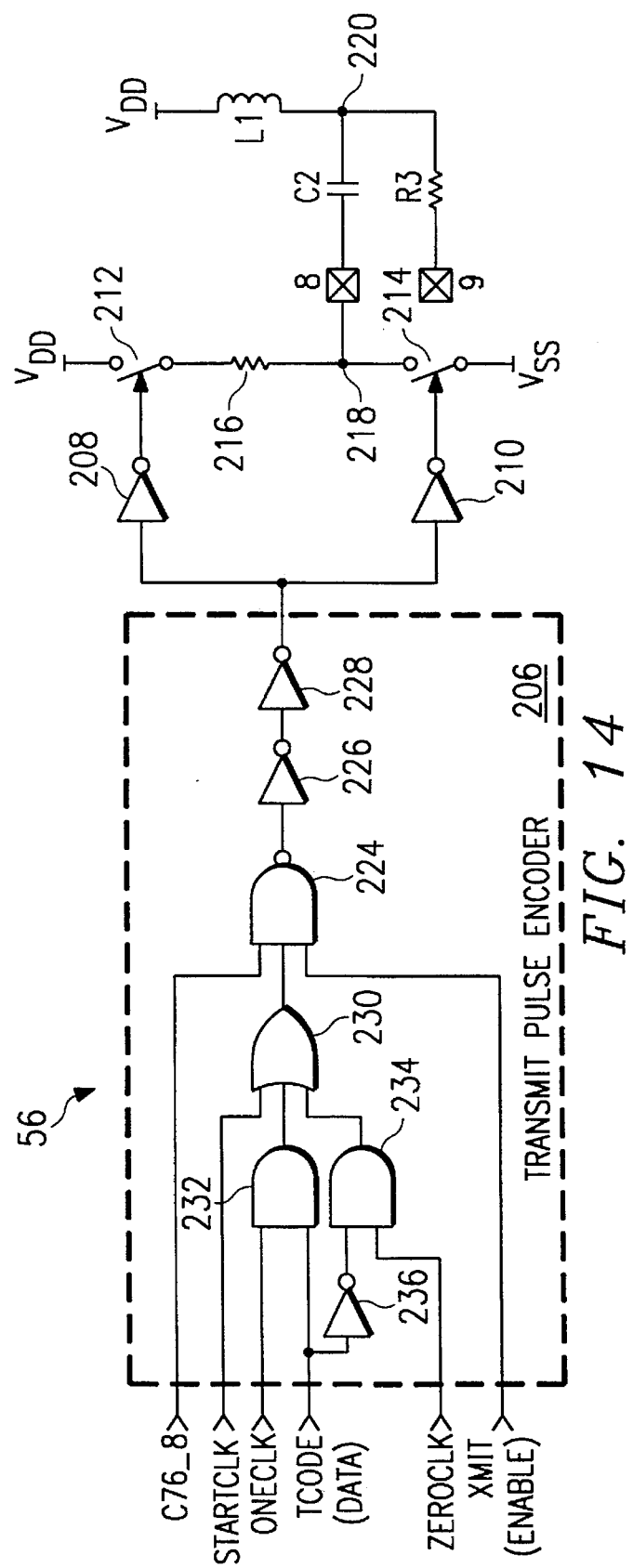

FIG. 14 illustrates schematically the transmitter circuit 56 depicted in FIG. 8. Transmitter circuit 56 comprises switching logic 206 which drives inverter drivers 208 and 210. Inverter drivers 208 and 210 control switches 212 and 214, respectively. Switch 212 connects $V_{DD}$ to a resistor 216. Resistor 216 is connected to a node 218. Switch 214 connects node 218 to $V_{SS}$. Node 218 is connected to a node 220 through an external connection, TRANS, at pad 8 through an external capacitor C2. Node 220 is connected to $V_{DD}$ through an external inductor L1. Also, node 220 is connected through an external resistor R3 back into integrated circuit 46 through RECV, at pad 9.

In one embodiment of transmitter circuit 56, resistors 216 and R3 are 10 kOhm resistors, C2 is a 1000 pF capacitor, and inductor L1 is a 4.8 mH inductor.

Logic 206 outputs to inverter drivers 208 and 210 the output of a NAND gate 224 twice inverted by inverters 226 and 228. Gate 224 is a three input NAND gate which combines C76_8 the output from an OR gate 230, and XMIT. Gate 230 is a three input OR gate having inputs STARTCLK, the output of an AND gate 232 and the output from an AND gate 234. Gate 232 has inputs ONECLK and TCODE. Gate 234 has inputs TCODE inverted by an inverter 236 and ZEROCLK.

In operation, logic 206 synchronizes output data on TCODE with the appropriate communications protocol window. In particular, a high data bit is synchronized with ONECLK and C76_8. A data low is synchronized with ZEROCLK and C76_8. XMIT acts as an enabling signal. The synchronized output signal from logic 206 will cause inverter 208 and 210 to close switches 212 and 214. Current will then flow through inductor 222. Logic 206 will peck inductor L1 twice per data bit due to the length of the pulses of the clocking signals and of TCODE.

f. PPM Decoder

Figure 15A:
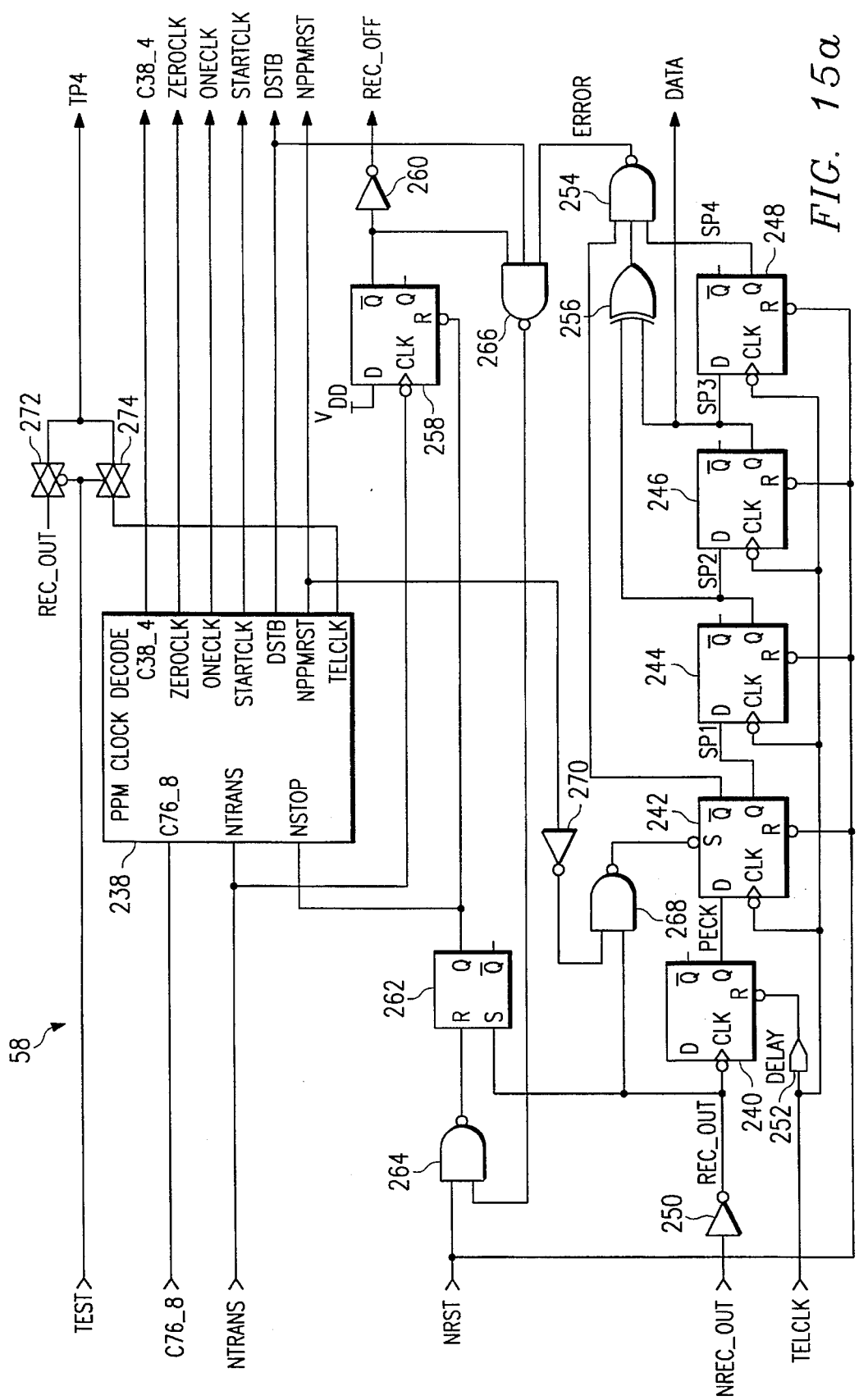
Figure 15B:
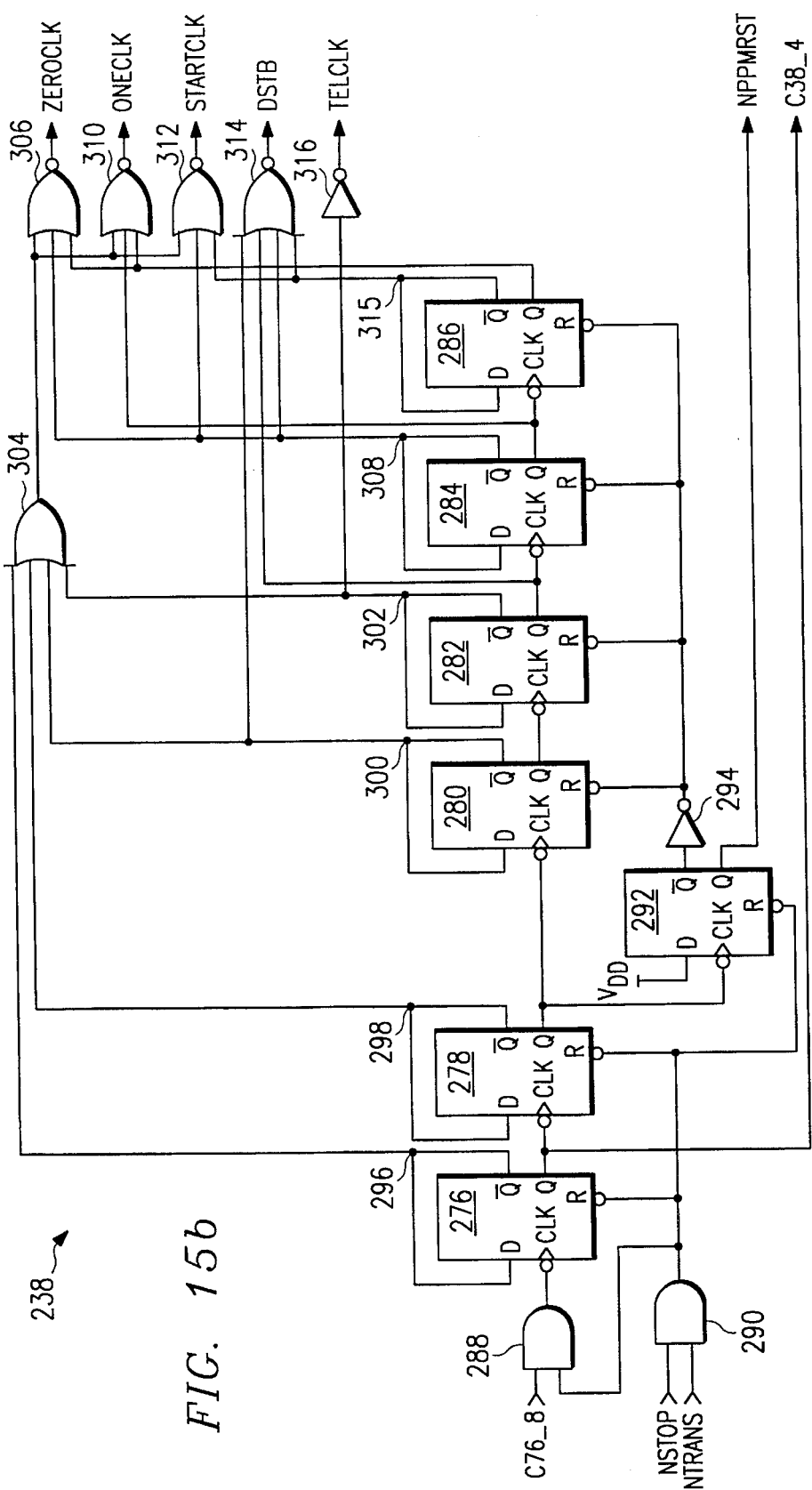

FIGS. 15*a* and 15*b* illustrate schematically the PPM decoder circuit 58 depicted in FIG. 8*a*. PPM decoder circuit 58 comprises a PPM clock decode block 238 and related data checking logic. Block 238 as depicted in the FIGURE generates C38_4, ZEROCLK, ONECLK, STARTCLK, DSTB and NPPMRST. Block 238 also generates signal TELCLK, a timing signal, for use within PPM decoder circuit 58. Block 238 is more fully described in connection with FIG. 15*b*.

FIG. 15*a* comprises five cascading D-type flipflops 240, 242, 244, 246 and 248. As depicted, the output of flipflops 240, 242, 244 and 246 are connected to the input of the next flipflop. Flipflop 240 is clocked by NREC_OUT inverted by an inverter 250. Flipflop 240 is reset by TELCLK after that signal is momentarily delayed by delay circuit 252. (Delay circuit 252 might be an AND gate with both of its inputs tied to TELCLK.) Flipflops 242, 244, 246 and 248 are each clocked by TELCLK and reset by NRST.

A NAND gate 254 ensures that the data bit input on NREC_OUT complies with the communication protocol described in FIG. 9*a*. Gate 254 has three inputs, the inverted output of flipflop 242, the output of an XOR gate 256 and the output of flipflop 248. The inputs to gate 256 are connected to the outputs of flipflops 244 and 246.

DATA is generated from the output of flipflop 246. REC_OFF is generated from the inverted output of a D-type flipflop 258 inverted by an inverter 260. Flipflop 258 has its input connected to $V_{DD}$ and is clocked by NTRANS. The reset signal to flipflop 258 is connected to the output of a RS flipflop 262. Flipflop 262 has a first input from the output of a NAND gate 264 and a second from the output of inverter 250. NAND gate 264 has inputs NRST and the output of a NAND gate 266. NAND gate 266 is a three input NAND gate having inputs of the inverted output of flipflop 258, DSTB and the output of a NAND gate 254. The set input to flipflop 242 is connected to the output of a NAND gate 268. The inputs to NAND gate 268 are connected to the output of inverter 250 and to NPPMRST through an inverter 270.

T-gates 272 and 274 alternately switch REC_OUT and TELCLK to TP4 under control of TEST. When TEST equals zero, TP4 is connected to the 4800 Hz signal TELCLK. When TEST equals one TP4 is connected to REC_OUT.

In operation, flipflops 240, 242, 244, 246 and 248 capture data present on NREC_OUT which is synchronized with the 4800 Hz TELCLK signal. Gate 254 ensures that the data bit follows the PPM protocol described in connection with FIG. 9*a*. Gate 254 outputs a high signal if any of the three PPM conditions are not met: (1) the start bit is high, (2) either the second or third bit is high, but not both or neither and (3) the no pulse detected window is low. Flipflop 258 and inverter 260 generate REC_OFF.

FIG. 15*b* illustrates a schematic diagram of PPM clock decode block 238 depicted in FIG. 15*a*. Block 238 comprises six D-type flipflops 276, 278, 280, 282, 284 and 286. These flipflops are cascaded together such that the output of flipflops 276, 278, 280, 282 and 284 are connected to the clock input of flipflops 278, 280, 282, 284 and 286, respectively. The clock input to flipflop 276 is connected to the output of AND gate 288. Gate 288 has two inputs, C76_8 and the output of an AND gate 290. AND gate 290 has inputs NSTOP and NTRANS. The output gate 290 is also connected to the resets of flipflops 276, 278 and to a D-type flipflop 292. Flipflop 292 is clocked by the output of flipflop 278 and its input is held high by $V_{DD}$. The output of flipflop 292 generates the signal NPPMRST. The inverted output of flipflop 292 inverted by an inverter 294 resets flipflops 280, 282, 284 and 286.

The input and inverted output of each of flipflops 276, 278, 280, and 282 are tied together to form nodes 296, 298, 300, and 302. These nodes form the inputs to OR gate 304. ZEROCLK is generated by a NOR gate 306. Gate 306 has three inputs, the output of gate 304, a node 308 and the output of flipflop 286. Node 308 is connected to the input and inverted output of flipflop 284. ONECLK is generated by a NOR gate 310. Gate 310 has three inputs, the output of gate 304, the output of flipflop 284 and the output of latch 286. STARTCLK is generated by a NOR gate 312. NOR gate 312 has three inputs, the output of gate 304, node 308 and the inverted output of flipflop 286. DSTB is generated by a NOR gate 314. NOR gate 314 has four inputs, node 300, the output of flipflop 282, node 308 and a node 315. Node 315 is connected to the input and the inverted output of flipflop 286. TELCLK is generated from node 302 inverted by an inverter 316.

g. Communications Modem

Figure 16:
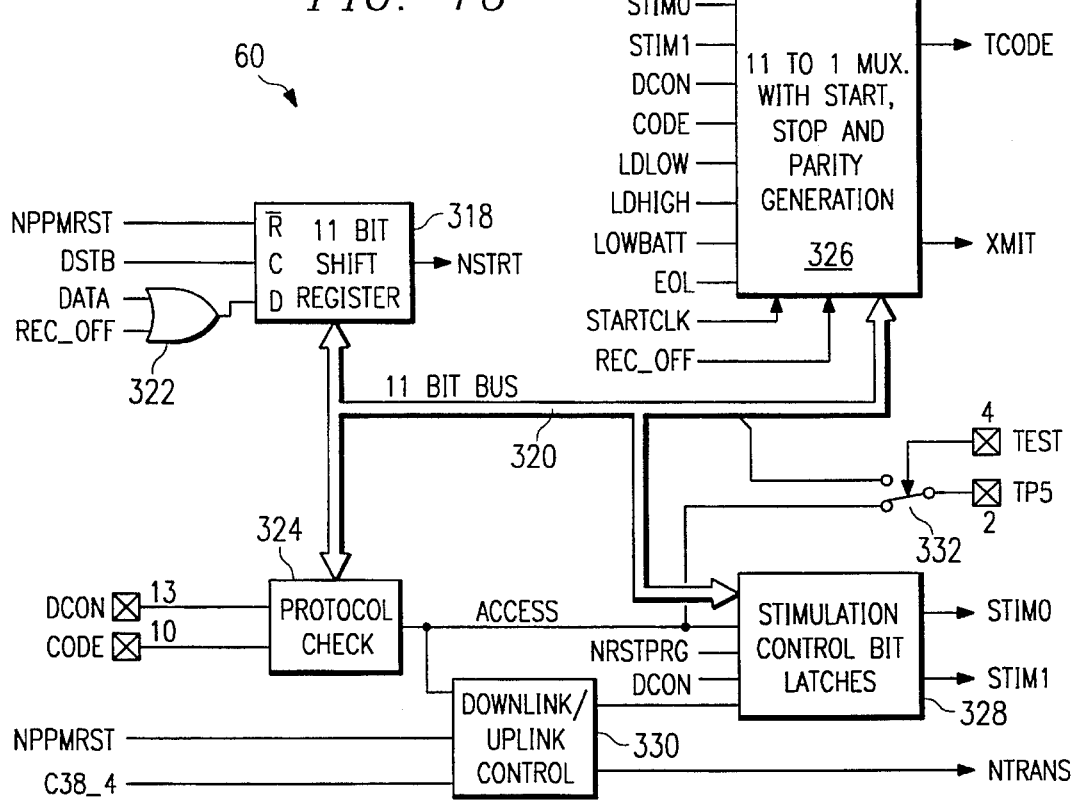
FIG. 16 illustrates a block diagram of the communication modem circuit depicted in FIG. 8b.

FIG. 16 illustrates a block diagram of the communication modem circuit 60 depicted in FIG. 8b. Communication modem circuit 60 comprises an 11 bit shift register 318 with outputs NSTRT and an 11 bit bus 320. Shift register 318 is reset by NPPMRST and is clocked by DSTB. DATA and REC_OFF are logically combined by an OR gate 322. The output of gate 322 is the data input to shift register 318. Bus 320 connects shift register 318 to protocol check circuit 324, to 11-to-1 multiplexer 326 and to stimulation control bit latches 328.

Protocol check circuit 324 has inputs DCON, CODE through pads 13 and 10, respectively. Protocol check circuit 324 has a single output ACCESS input to latches 328 and to a downlink/up-link control circuit 330. Latches 328 also have inputs NRSTPRG, DCON, and the output from circuit 330. Latches 328 output STIM0 and STIM1. Circuit 330 also has inputs NPPMRST and C38_4. As depicted, multiplexer 326 has data inputs STIM0, STIM1, DCON, CODE, LDLOW, LDHIGH, LOWBATT, and EOL. Multiplexer 326 also has two control inputs STARTCLK and REC_OFF. Multiplexer 326 outputs TCODE and XMIT.

A switch 332 alternately switches an external connection, TP5, to either the tenth data line in bus 320 or to ACCESS depending upon the logic value of TEST. If TEST=0, then TP5 is connected to ACCESS. If TEST=1, TP5 is connected to a data line within bus 320 containing the final or stop bit of information. Pad 2 is connected to TP5 while pad 4 is connected to TEST.

In operation, 11 bits of data are strobed into shift register 318 through DSTB and DATA. These bits are then made available on bus 320. Protocol check circuit 324 then compares the received data with the programmed data word requirements described in connection with FIG. 9b. If these requirements are met, then protocol check circuit 324 outputs a logic one on ACCESS. Latches 328 check the second received data bit to determine if STIM0 and STIM1 should be written to (RNW=0) or simply read from (RNW=1). If a write command is indicated on bus 320, latches 328 will be loaded with new data. If only a read operation is indicated, communication modem 60 will up-link a handshake communication to the external receiver. Circuit 330 outputs a logic zero on NTRANS after a valid communication is received as indicated by protocol check circuit 324.

After a valid downlink, communication modem 60 outputs 11 data bits according to the communication protocol described in connection with FIG. 9c on TCODE. Multiplexer enables transmitter circuit 56 through XMIT. Multiplexer 326 outputs each bit in the proper order by receiving sequentially a jammed bit on each of the 11 bus lines 320 from shift register 318. A logic 1 is jammed into shift register 318 through REC_OFF. Multiplexer 326 sequentially enables each data line as the one ripples through bus 320. This procedure causes the contents of STIM0, STIM1, DCON, CODE, LDLOW, LDHIGH, LOW, BATT and EOL data lines along with the start bit to be serially outputted through TCODE in the proper order without requiring an address counter. An internal toggle generates an odd parity bit after the last data bit is output and immediately prior to the stop bit. It should be understood that a conventional multiplexer with address bits could be employed in place of multiplexer 326.

h. Lead Status

Figure 17:
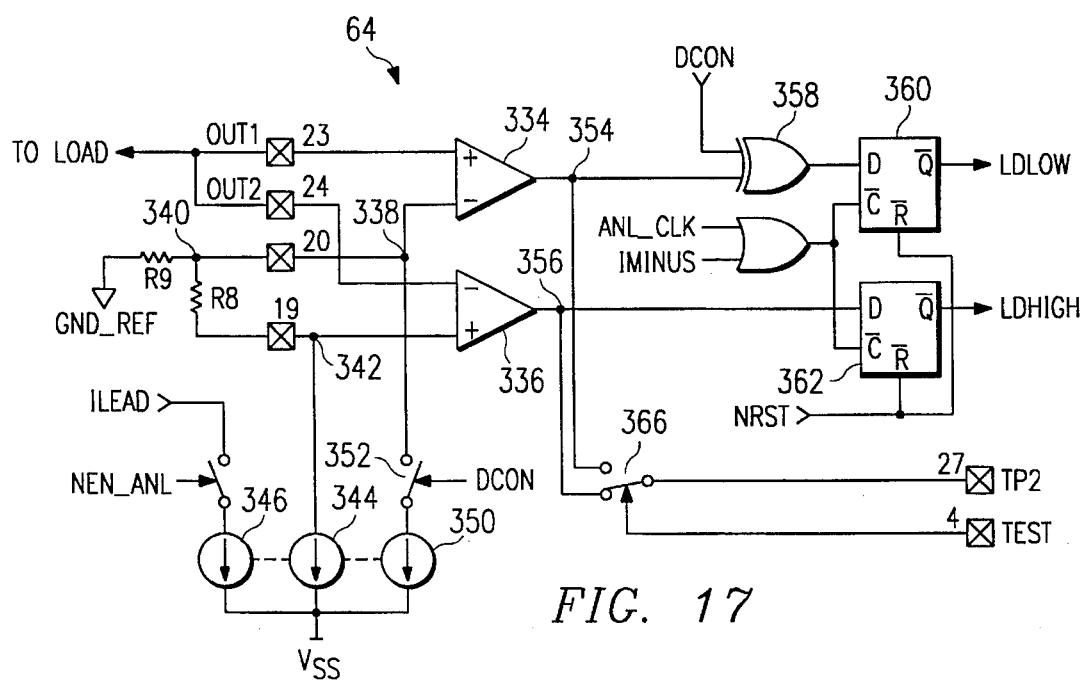
FIG. 17 illustrates schematically the lead status circuit depicted in FIG. 8b.

FIG. 17 illustrates schematically the lead status circuit 62 depicted in FIG. 8b. Lead status circuit 62 comprises a first and second comparator 334 and 336. OUT1 is connected to the first input of comparator 334 through pad 23. A node 338 is connected to the second input of comparator 334. Node 338 is also connected to node 340 through external pad 20. Node 340 is connected to GND_REF through resistor R9. The first input to comparator 336 is connected to node 342. Node 342 is connected to a node 340 through external resistor R8 and pad 19. Node 342 is also coupled to a current mirror 344. Current mirror 344 is connected to $V_{SS}$ and mirrors current through a current mirror 346. Current mirror 346 is connected to ILEAD through switch 348 under the control of NEN_ANL current mirror. Current mirror 346 is also connected to $V_{SS}$. Node 338 is coupled to a second current mirror 350 through a switch 352 under the control of DCON. Current mirror 350 also mirrors current mirror 346 and is connected to $V_{SS}$. The outputs to comparators 334 and 336 are connected to nodes 354 and 356. Node 354 is one input to a XOR gate 358. Gate 358 has DCON as its second input. The output to gate 358 is connected to the input of a flipflop 360. Node 356 is connected to the input of a flipflop 362. Flipflops 360 and 362 are reset by NRST and are clocked by the output from an OR gate 364. Gate 364 has inputs ANL_CLK and IMINUS. Flipflops 360 and 362 generate LDLOW and LDHIGH, respectively.

Switch 366 alternately connects TP2 through pad 27 to each of the outputs of comparators 334 and 336. Switch 366 is under the control of TEST through pad 4. When TEST equals 0, TP2 is connected to node 356. When TEST equals 1, TP2 is connected to node 354.

In the AC mode of operation, the ITGS has a single electrode output. OUT1 and OUT2 are therefore shorted together off chip. Comparator 334 compares the voltage on OUT1 to the voltage at node 340. If voltage on OUT1 drops below the voltage at node 340, comparator 334 will output a zero to flipflop 360 and onto LDLOW. The voltage at node 340 is determined by the choice of resistor R9. Comparator 336 compares the voltage on OUT1 with a voltage at node 342. When the voltage on OUT2 exceeds the voltage at node 342, comparator 336 outputs a logic level zero which is latched by flipflop 362 and output on LDHIGH. The voltage at node 342 is determined by the choice of resistors R8 and R9. NEN_ANL disables lead status circuit 62 during the positive portion and rest portion of the output signal to conserve power. Current mirror 344 sinks nA 100 of current from node 342.

In the DC mode of operation, OUT1 and OUT2 are each connected to a cathode through pads 23 and 24. Also, node 342 is connected to GND_REF through resistor R8. (Resistor R8 is not connected to node 340). Switch 352 is closed by DCON, allowing current mirror 350 to sink nA 100 from node 338. Both comparators 334 and 336 compare the voltages on OUT1 and OUT2 to the voltages on nodes 338 and 342, respectively. Comparator 334 will output a logic level zero if OUT1 is lower than the voltage at node 340 (high lead impedance on OUT1). Comparator 336 will output a logic level one if OUT2 is lower than the voltage at made 342 (high lead impedance on OUT2). These outputs will be latched by flipflops 360 and 362.

i. Receiver

FIG. 18 illustrates schematically the receiver circuit 64 depicted in FIG. 8a. Receiver circuit 64 comprises a power transconductance comparator 368 which outputs NREC_OUT. The first input to comparator 368 is connected to a node 370. The second input is connected to an internal voltage supply which will range from 75 to 150 mV. Current is sunk from node 370 by a current source 372. Current source 372 is coupled to $V_{SS}$. Node 370 is connected to an external node 220 by resistor R3 through external pad 9. Node 370 is also connected to $V_{DD}$ through inductor L1. Pad 8 is an external connection for a transmitter circuit 56. It is connected to node 374 through capacitor C2.

As described in connection with FIG. 14, inductor L1 has an inductance of 4.8 mH, resistor R3 has a resistance of 10 kOhms and capacitor C2 has a capacitance of 1000 pF.

In operation, comparator 368 pulses low when inductor L1 receives a pulse from an external transmitter. Comparator 368 can detect a pulse of approximately 20 mV in amplitude, 7.5 μsec in width, and pulses spaced as close together as 75 μsec.

j. Battery Status Indicator

FIG. 19 illustrates schematically the battery status indicator circuit 66 depicted in FIG. 8b. Battery status circuit 66 comprises a comparator 376. The output from comparator 376 is logically combined with REC_OFF by an AND gate 378. The output of gate 378 is connected to the input of a latch 380. Latch 380 is reset by NRST and its output generates LOWBATT. The output of latch 380 is combined with the output from gate 378 by an AND gate 382. The output of AND gate 382 is connected to the input of a latch 384. Latch 384 is reset by NRST and clocked by C1_49. Latch 384 requires two clock cycles to latch. The output of latch 384 generates EOL.

The first input to comparator 376 is connected to a node 386. Node 386 is connected to an external node 388 through EOLTRM and pad 12. External capacitor C3 is connected between node 388 and $V_{DD}$. An external resistor R4 is connected between the node 388 and $V_{SS}$. Two current mirrors 390 and 392 are connected in parallel between node 386 and a node 394. A switch 396 selectively connects current source 392 to node 394 under control of the output of latch 380. Node 394 is coupled to $V_{DD}$ by a switch 398 under control of NEN_ANL. The second input of comparator 376 is connected to GND_REF.

A switch 400 alternately connects TP3 through pad 28 to either the output of gate 378 or the output of latch 384. Switch 400 is controlled by TEST through external pad 4. When TEST equals zero, TP3 is connected to the output of gate 378. When TEST equals one, TP3 is connected to the output of latch 384.

In operation, comparator 376 compares the voltage at node 386 with GND_REF. The first voltage, that of node 386, is constant depending upon how much current is drawn through resistor R4 by current mirrors 390 and 392. GND_REF however drops as $V_{DD}$ drops during the lifetime of the circuit.

Initially, the output of latch 380 is low and switch 396 is closed. Current mirrors 390 and 392 sink 120 nA through resistor R4. Initially, GND_REF is at a higher potential than node 386. The output of comparator 376 is therefore low. As the battery ages, GND_REF will drop below the constant voltage at node 386 and trip the output of comparator 376 high. This will output a LOWBATT bit from latch 380 and open switch 396. Node 386 will therefore only have 80 nA current flowing through it. This will lower the voltage of node 388. GND_REF will again be higher than the voltage at node 386 causing output of comparator 376 to go low again. Eventually as the battery continues to age, GND_REF will drop below the second, even lower, voltage level at node 386 tripping the output of comparator 376 high. The second high output will be combined with the output from latch 380 by gate 382 and output as EOL.

k. Voltage Reference/Regulator

FIG. 20 illustrates a block diagram of the voltage reference/regulator circuit 68 depicted in FIG. 8b. Voltage reference/regulator circuit 68 comprises a diode 403 connected to $V_{DD}$ and node 402, biased as depicted. Node 402 is connected to $V_{SS}$ through a current mirror 404. A second diode 405 is connected between $V_{DD}$ and VSET1 through pad 15. VSET1 is coupled to VSET2 through external resistor R5. VSET2 exits the circuit through pad 16. VSET2 is coupled to a node 406. Node 406 is coupled to $V_{SS}$ through a current mirror 408. An op-amp 410 has its first input to node 406 and its second input connected to node 402. An external resistor R6 is connected between $V_{DD}$ and pad 16. External resistor R7 is connected between $V_{DD}$ and a node 412. Node 412 is coupled to VREF through pad 17. Pad 17 is connected to $V_{SS}$ through a current mirror 414. Node 412 is the first input of comparator 416. The second input to comparator 416 is tied to its output. The output of comparator 416 generates GND_REF (internally and GND externally). GND_REF is coupled to one terminal of an external capacitor C5 through external pad 18. The second terminal of capacitor C5 is coupled to $V_{DD}$. First and second current mirrors 418 and 420 are connected in series between $V_{DD}$ and $V_{SS}$. Current mirrors 422 and 424 are coupled to $V_{DD}$ and generate the 20 nA bias currents IREC and ILEAD respectively. ITEST is connected to $V_{SS}$ through a current mirror 426. IDCON is connected to $V_{SS}$ through a current mirror 428. ICODE is connected to $V_{SS}$ through a current mirror 430. IBATT is connected to $V_{SS}$ through a current mirror 432. IPOR is connected to $V_{SS}$ through a current mirror 434. Current mirrors 426, 428, and 430 generate 100 nA bias currents. Current mirrors 432 and 434 generate a 20 and 10 nA bias current respectively.

NRSTPRG controls a switch 436. Switch 436 connects $V_{DD}$ to a current mirror 438. The output of voltage mirror 438 is connected to output of op-amp 410. The currents flowing through current mirrors 438, 404, 408, 414, 420, 426, 428, 430, 432 and 434 are governed by the output of op-amp 410 and are compensated for variation in temperature as will be described below. Current mirrors 418, 422 and 424 are controlled by the output of op-amp 410 through current mirror 420. Current mirror 438 enables voltage reference/regulator circuit 68.

Voltage reference/regulator circuit 68 is based on the Band Gap principal. Op-amp 410 sets the current mirrors such that the voltages at nodes 402 and 406 are equal. Therefore, the current through R6 is directly proportional to the single diode 403. The current through R5 is based on the difference in the two diodes 403 and 405, which are selected to have an 8:1 difference in current density. When R5 is selected in the proper balance with R6 (R6/R5=16.2), the current sum will be temperature independent. VREF is set by the mirrored current and external resistor R7. In the illustrated embodiment, VREF equals GND (GND_REF) or VDD−1.5 Volts.

5. Stimulator Circuit Configurations a. AC Configuration

Figure 21:
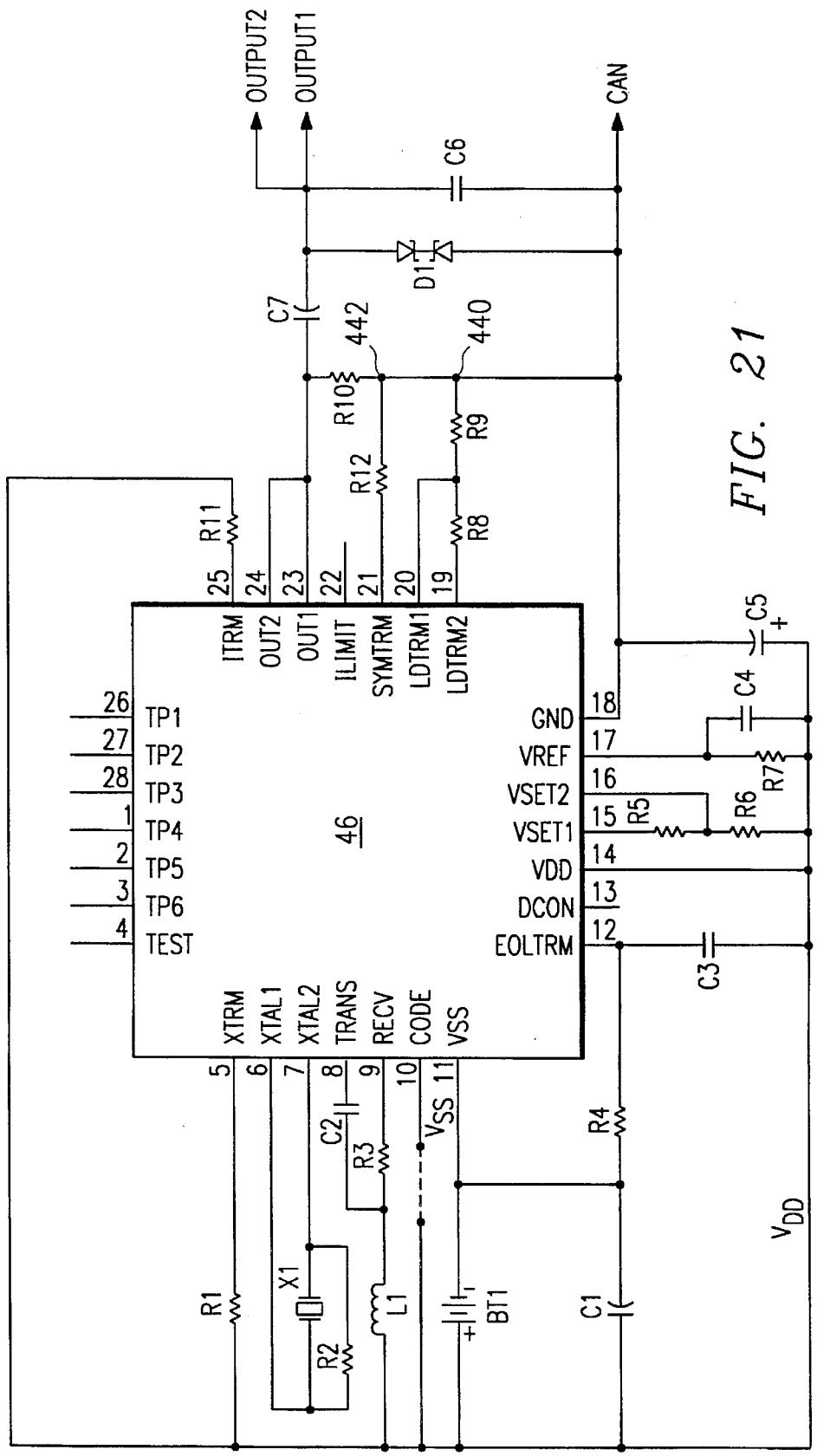
FIG. 21 illustrates schematically the circuit depicted in FIGS. 8a and 8b configured for the AC mode of operation.

FIG. 21 illustrates schematically the circuit depicted in FIGS. 82 and 85 configured for the AC output signal. When packaged, pins 1–4 and 26–28 are left open on integrated circuit 46. Testing is done before final assembly.

XTRM is connected to $V_{DD}$ 5 through resistor R1. Resistor R1 is a 10 MOhm resistor. XTAL1 is connected to crystal X1 in parallel with resistor R2. XTAL2 is connected to the other terminal of crystal X1 and resistor R2. Crystal X1 is a 76.8 kHz crystal and resistor R2 has a resistance of 20 MOhm. TRANS, is connected to one terminal of capacitor C2. RECV is connected to the first terminal of external resistor R3. The remaining terminal of capacitor C2 and resistor R3 are tied together and to the first terminal of inductor L1. The second terminal of inductor L1 is connected to $V_{DD}$. Capacitor C2 has a capacitance of 1,000 pF, resistor R3 has a resistance of 10 kOhm, and inductor L1 has an inductance of 4.8 mH. CODE may or may not be connected to $V_{DD}$ through external pad 10. $V_{SS}$ is connected to the negative terminal of battery BT1. Battery BT1 is a 2.8 volt lithium iodine battery rated for 200 mAH. A slightly larger battery may be substituted increasing the rating of the battery BT1 to 0.5 AH.

As depicted, $V_{SS}$ is also connected to one terminal of capacitor C1 and one terminal of resistor R4. The second terminal of capacitor C1 is connected to $V_{DD}$ and the second terminal of resistor R4 is connected to EOLTRIM. EOLTRIM is also connected to $V_{DD}$ through capacitor C3. Capacitors C1 and C3 have a capacitance of 22 µF and 100 pF respectively. Resistor R4 is actively trimmed with a range of 3–9 MOhm to achieve a LOWBATT trip point of 2.4 prior to final assembly. DCON is left floating at external pad 13. $V_{DD}$ is connected to the positive terminal of battery BT1. VSET1 is connected to $V_{DD}$ through resistor series combination of resistors R5 and R6. VSET2 is connected to the node formed by the inner connection of resistor R5 to resistor R6. VREF is connected to parallel resistor/capacitor combination. Parallel resistor capacitor combination comprises resistor R7 and capacitor C4. The second terminal of R7 and C4 are connected to $V_{DD}$. Resistors R6 and R7 have a resistance of 18.75 MOhm. Resistor R5 is actively trimmed prior to assembly to generate GND=$V_{DD}$−1.5 Volts. GND is coupled to $V_{DD}$ through capacitor C5 and to the electrode window on the bone growth stimulator.

LDTRM2 is connected to a node 440 through a resistor series comprising resistors R8 and R9. Node 440 is connected to GND. LDTRM1 is connected to the node formed by the connection of resistors R8 and R9. The low lead impedance trip point is set by actively trimming resistor R9. The high impedance trip point is set by actively trimming resistor R8 after resistor R9. SYMTRIM is connected to a node 442 through optional resistor R12. ILIMIT exits integrated circuit 46 at external pad 22. OUT1 is connected to the output electrode through capacitor C7. Capacitor C7 ensures that the output has no net DC component. Capacitor C7 has the capacitance of 10 µF. OUT1 is also connected to node 442 through resistor R10. Resistor R10 has a resistance of 2 MOhm. Nodes 442 and 440 are electrically connected. OUT2 is connected to OUT1. ITRIM is connected to $V_{DD}$ through resistor R11. Resistor R11 is actively trimmed to set the output current. In addition, zener diode D1 is coupled between GND and output and are biased as depicted. They provide high voltage protection to the circuit. Capacitor C6 is also connected between OUTPUT1 and GND. Capacitor C6 protects the circuit from EMI. Capacitor C6 has a capacitance of 1,000 pF.

b. DC Configuration

Figure 22:
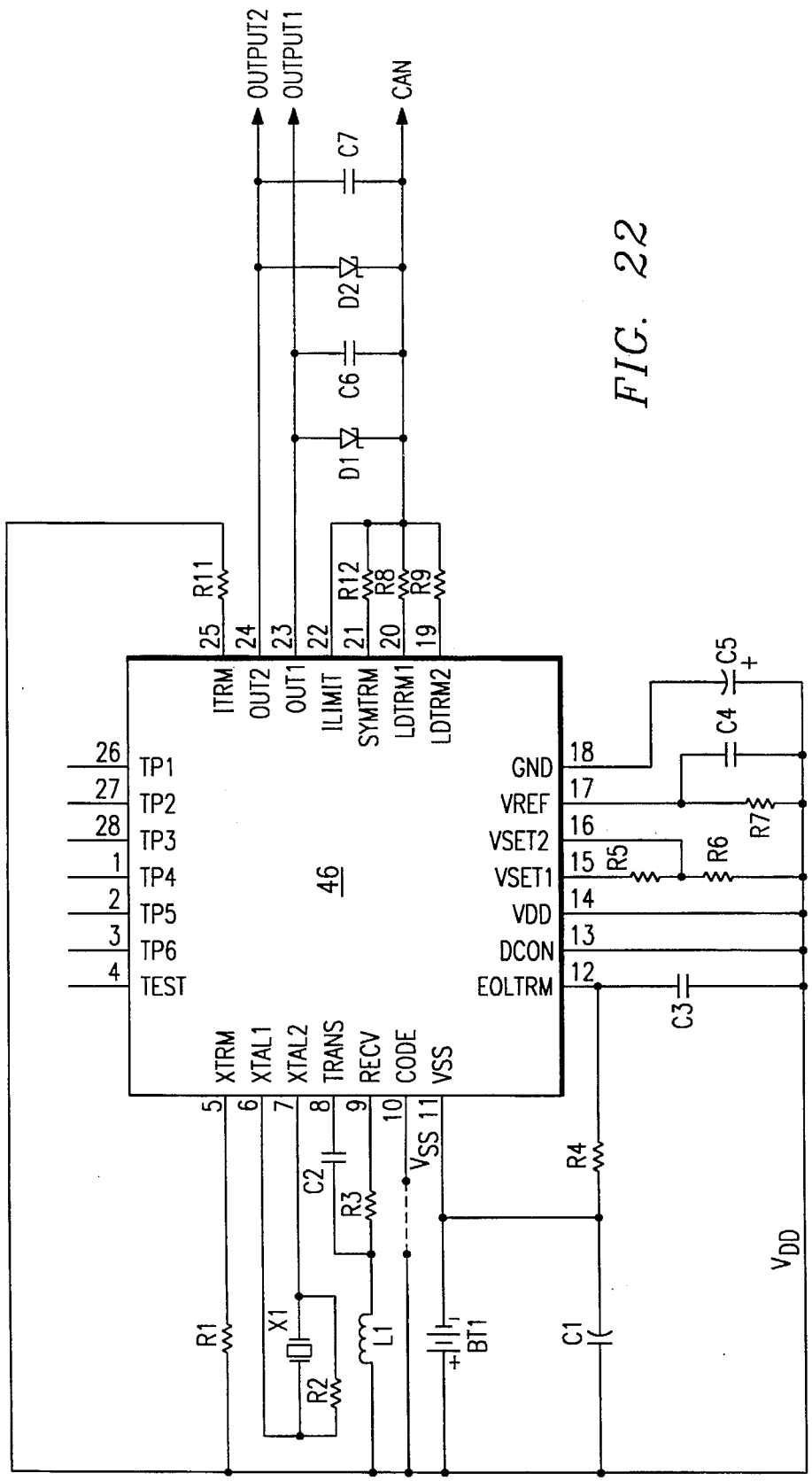
FIG. 22 illustrates schematically the circuit depicted in FIGS. 8a and 8b configured for the DC mode of operation.

FIG. 22 illustrates schematically the circuit depicted in FIGS. 8a and 8b configured for the DC output signal. Integrated circuit 46 has substantially the same configuration for the DC output as for the AC output. There are the following differences: DCON is connected to $V_{DD}$ to indicate the DC mode of operation. OUT2 is connected to the second cathode. Each output has a parallel zener diode/ capacitor combination between it and LDTRM1. Diode D1 and capacitor C6 are connected in parallel between OUT1 and ILIMIT. Diode D2 and capacitor C7 are connected in parallel between OUT2 and ILIMIT. ILIMIT is connected to the anode, CAN.

Certain resistors and capacitors may have different values to reflect the DC configuration. This adjustment can be made by one skilled in the art in connection with the foregoing description.

E. PROGRAMMER/MONITOR

Figure 23:
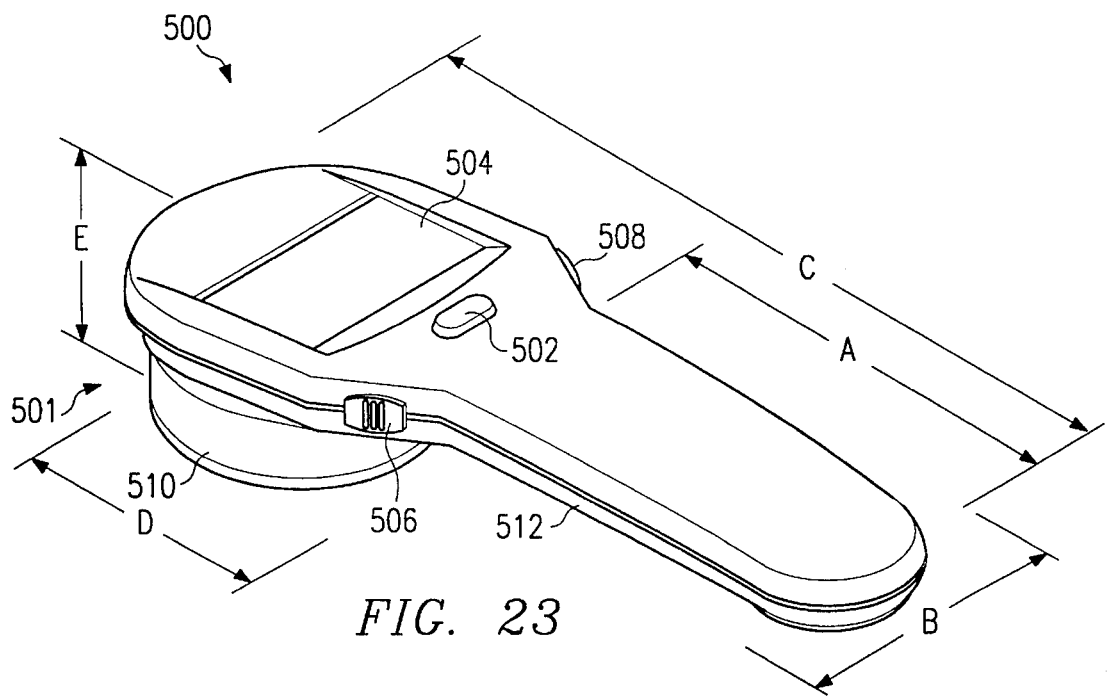
FIG. 23 is a hand-held programmer/monitor unit.

FIG. 23 is a hand-held programmer/monitor (P/M)unit 500. In this embodiment, P/M 500 is used to program, monitor and otherwise control ITGS 10 of FIG. 1. (Unless otherwise noted, any interaction between AC ITGS 10 is likewise applicable to DC ITGS 26 of FIG. 3. Only ITGS 10 is referred to in the specification and FIGURES for simplicity.)

P/M 500 includes a housing shown generally at 501, for enclosing the internal components of P/M 500. Housing 501 is designed for one-handed operation of P/M 500. Specifically, handle 512 is designed to be comfortably gripped by the human hand. Handle 512 has a length A, which is approximately 130.5 millimeters, and a width B, which is approximately 47.6 millimeters. These dimensions have been shown to allow comfortable one-handed operation of P/M 500 for extended periods of time.

Figure 35:
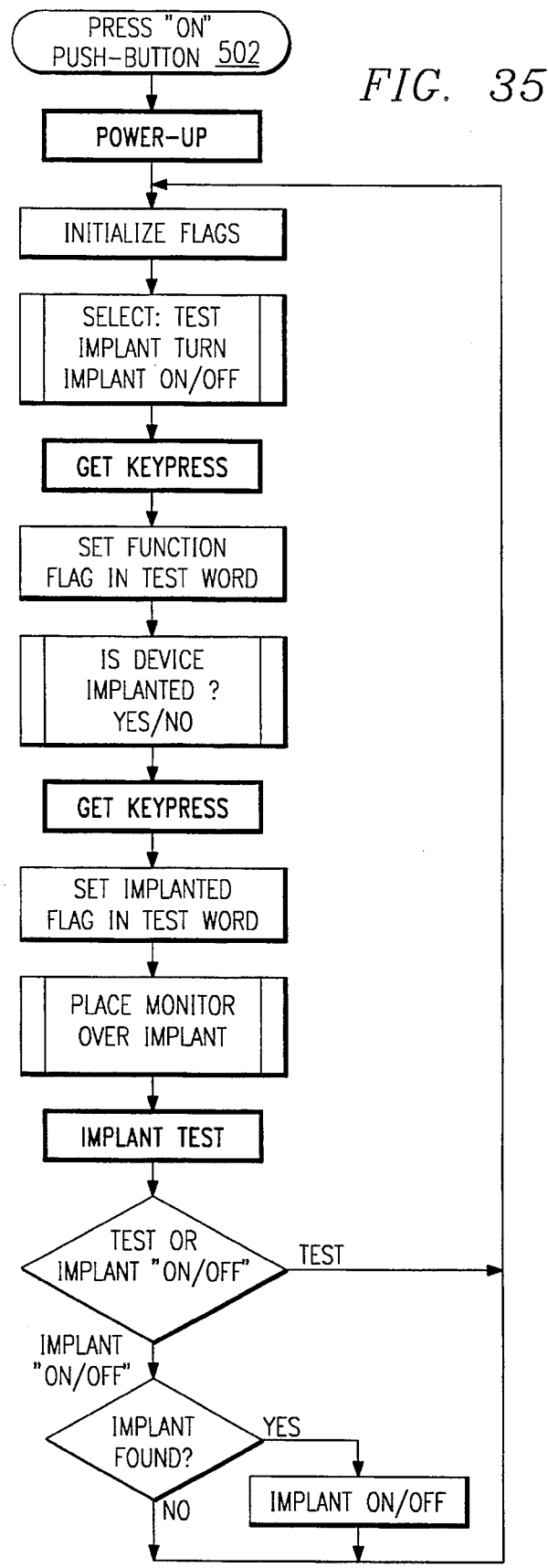
FIG. 35 is a flow chart of the P/M Program executed by the processor of FIG. 26.

P/M 500 also includes a power "on" switch 502. P/M 500 further includes a display 504 for displaying an interactive menu and the status of both ITGS 10 and P/M 500. The interactive menu displays two function choices. The two function choices are arranged in such a way on display 504 that one function choice is selected by pressing a push-button 506 (KEY1) and the remaining function choice is selected by pressing a push-button 508 (KEY2). By using push buttons 506 and 508, a user can "walk through" the menu and select programming or monitoring functions for P/M 500 to implement relative to ITGS 10. For example, the first two function choices displayed on display 504, after P/M 500 is turned "on", are "TEST IMPLANT" as the first function choice and "TURN IMPLANT ON/OFF" as the second function choice, as shown in FIG. 35, which will be discussed in detail below. To select the first function choice for testing ITGS 10, push-button 506 is pressed. To select the second function choice for toggling the "on/off" state of ITGS 10, push-button 508 is pressed. Other function choices are phrased in the form of a question. This is how P/M 500 prompts for input of necessary data. For example, FIG. 35 also shows a second display "IS DEVICE IMPLANTED? YES/NO". To indicate affirmatively that ITGS 10 is implanted, push-button 506 is pressed. To indicate negatively that ITGS 10 is not implanted, push-button 508 is pressed. The interactive program and the monitoring and programming functions of P/M 500 are discussed in detail below in conjunction with FIGS. 35–48.

P/M 500 also has an antenna coil housing 510, which is part of housing 501, for covering the transmit and receive antenna coils to be discussed below in conjunction with FIGS. 31–34.

1. Circuit Description

Figure 24:
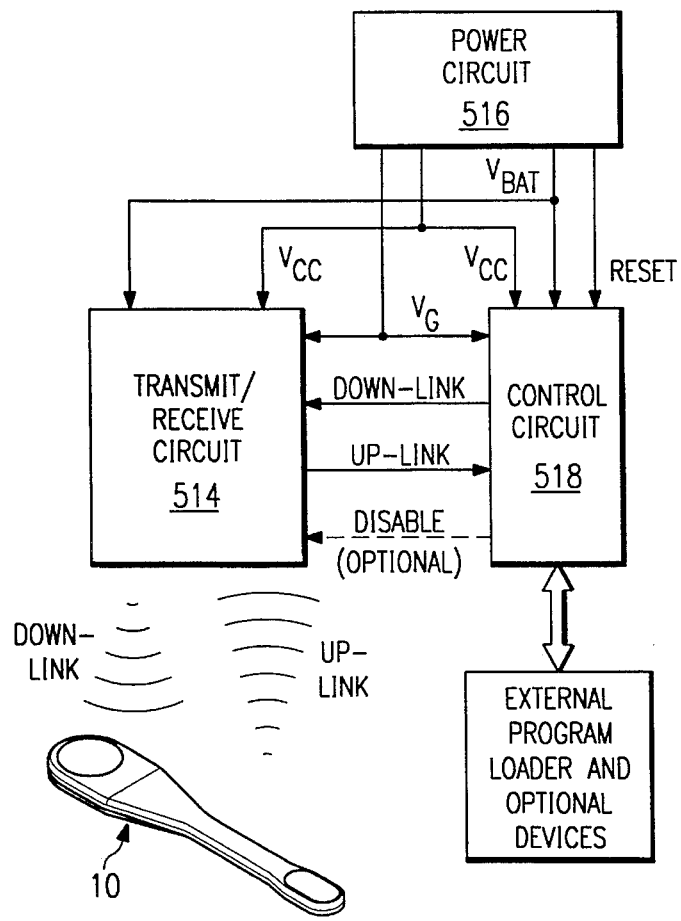
FIG. 24 is a block diagram of the electronic circuitry disposed within the programmer/monitor unit of FIG. 23.

FIG. 24 is a block diagram of the electronic circuitry disposed within P/M 500. This circuitry includes transmit/receive circuit 514 for transmitting the down-link program data word of FIG. 9b (hereinafter DOWN-LINK) to and receiving the up-link handshake of FIG. 9c (hereinafter UP-LINK) from ITGS 10.

Control circuit 518 generates the interactive menu and implements the selected function. Control circuit 518 also generates the DOWN-LINK which transmit/receive circuit 514 transmits to ITGS 10 (FIG. 1). Control circuit 518 also processes the UP-LINK which transmit/receive circuit 514 receives from ITGS 10. Additionally, control circuit 518 may generate a DISABLE signal for disabling the receiving capabilities of transmit/receive circuit 514 during the time transmit/receive circuit 514 is transmitting. This prevents transmit/receive circuit 514 from receiving its own transmission. However, as will be discussed below, some embodiments of transmit/receive circuit 514 do not require the above described disable feature. Control circuit 518 is also coupled to an external program loader for loading the program which control circuit 518 must execute to function as described above. Control circuit 518 may be coupled to other external devices such as a computer, printer, or display device.

Power circuit 516 provides three voltages, VBat, Vcc, and Vg to transmit/receive circuit 514 and control circuit 518. In this embodiment, VBat is approximately 9 volts, Vcc is approximately 5 volts, and Vg is ground which equals approximately 0 volts. Power circuit 516 also provides a RESET signal to reset control circuit 518 when "on" switch 502 is pressed.

a. Power Circuit

Figure 25:
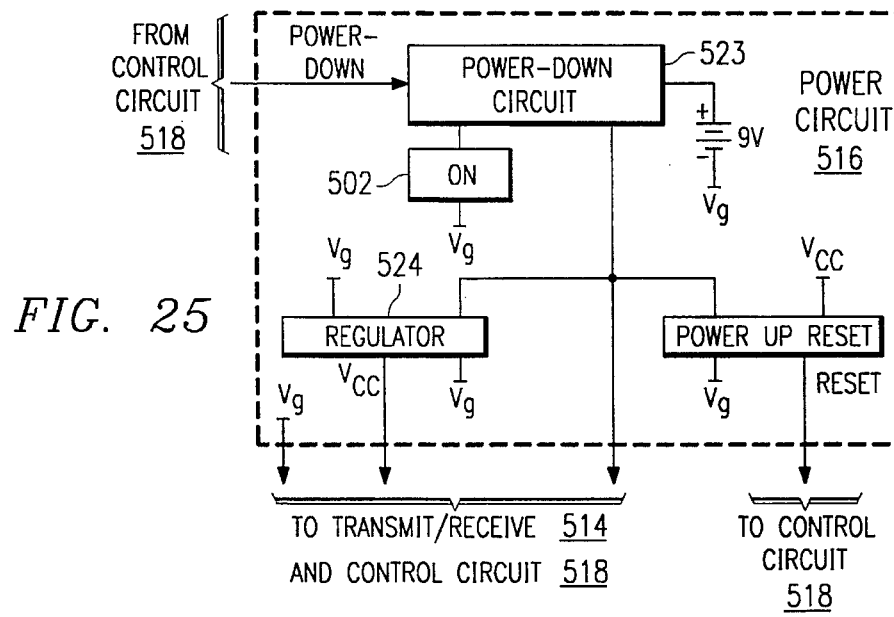
FIG. 25 is a block diagram of the power circuit of FIG. 24.

FIG. 25 is a block diagram of power circuit 516. Power-down circuit 523 begins to or continues to provide voltage VBat from a 9 volt battery when "on" switch 502 is pushed. In response to a POWER-DOWN signal from control circuit 518, power-down circuit 523 ceases to provide VBat, thus turning P/M 500 "off". In this embodiment, control circuit 518 generates the POWER-DOWN signal when P/M 500 has been inactive for approximately 2 minutes, i.e., neither push-button 506 nor push-button 508 has been pressed. Regulator 524 converts VBat into Vcc. Power-up reset circuit 526 provides a RESET signal to control circuit 518 when switch 502 is pressed and power-down circuit 523 begins to provide VBat. If power-down circuit 523 is already providing VBat, pressing "on" switch 502 has no affect upon power-up reset circuit 526, and no RESET signal is generated.

b. Control Circuit

Figure 26:
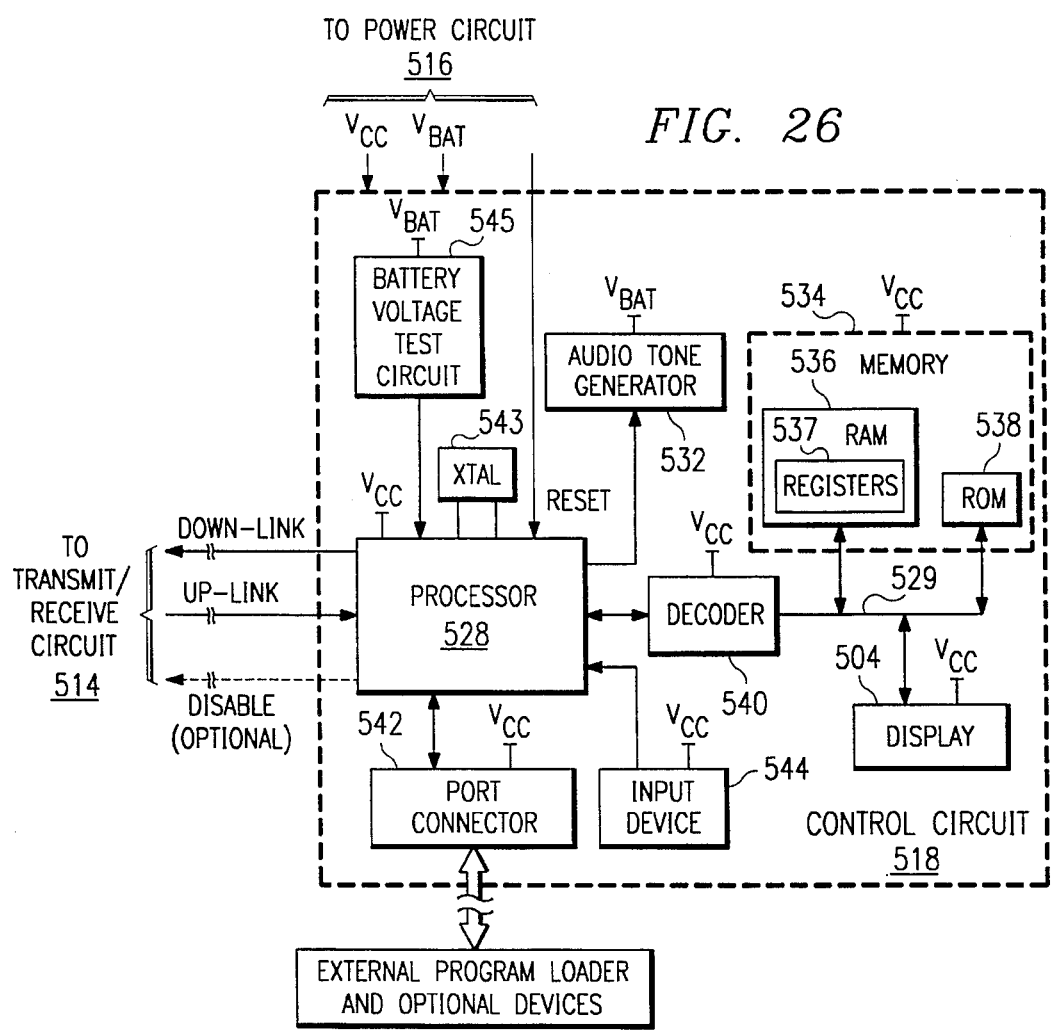
FIG. 26 is a block diagram of the control circuit of FIG. 24.

FIG. 26 is a block diagram of control circuit 518. A processor 528 generates the interactive menu on display 504 via an address/data bus 529. In this embodiment, display 504 is a Liquid Crystal Display (LCD), although other embodiments may include different types of displays. Both processor 528 and display 504 are powered by voltage Vcc. Additionally, processor 528 generates the DOWN-LINK for transmit/receive circuit 514 to transmit to ITGS 10. Also, processor 528 processes the UP-LINK from transmit/receive circuit 514. As discussed above, the UP-LINK is transmitted by ITGS 10 in response to the DOWN-LINK. Processor 528 instructs audio tone generator 532, which is powered by voltage VBat, to generate one of several audible tones in response to the UP-LINK, or lack thereof. This tone generation will be discussed below in more detail in conjunction with FIGS. 36, 39 and 43–48.

Still referring to FIG. 26, a memory 534, powered by voltage Vcc, is provided for storing data and instructions for processor 528. The instructions are in the form of a program (part of which includes the interactive program discussed above) and subprograms which will be discussed below and in conjunction with FIGS. 35–48. Memory 534 includes a Random Access Memory (RAM) 536 for temporary storage of data. RAM 536 includes a block of registers 537, each of which is used for temporary storage of data during execution of the program and various subprograms by processor 528. Register block 537 will be discussed in more detail below in conjunction with FIGS. 27 and 28. Memory 534 also includes a Read Only Memory (ROM) 538 for permanent storage of the program and subprograms mentioned above. The program and subprograms include instructions for instructing processor 528 to generate and implement the interactive menu, generate the DOWN-LINK, process the UP-LINK, and determine and display the status of both ITGS 10 and P/M 500. Processor 528 communicates with memory 534 via address/data bus 529. A decoder 540, powered by voltage Vcc, provides an interface between processor 528 and the address/data bus 529.

Again referring to FIG. 26, the program and subprograms are loaded into ROM 538 via processor 528 and a port connector 542 which is powered by voltage Vcc. An external program loader downloads the program and subprograms through the external interface provided by port connector 542. Other external devices, such as a computer, display or printer may be interactively coupled to processor 528 via port connector 542. For example, the UP-LINK received from ITGS 10 may be fed to an external computer for processing. In response to the UP-LINK, the external computer may command processor 528 via port connector 542 to send appropriate instructions via a DOWN-LINK to ITGS 10.

Control circuit 518 also includes an input device 544, which includes push-buttons 506 and 508, coupled to processor 528 and powered by voltage Vcc, for allowing selection between the function choices provided by the displayed interactive program. A crystal 543 sets the internal clock signal of processor 528 to a stable frequency whose optimum value is typically provided by the manufacturer of processor 528. A battery voltage test circuit 545 provides a test voltage to processor 528 which is proportional to voltage VBat. Processor 528 processes the test voltage to determine whether or not the 9 volt battery is "low" (i.e., Vbat is sufficient for proper operation of P/M 500, but is low enough to suggest the 9 volt battery will soon need to be replaced) or at its "end of life" (i.e., Vbat is insufficient for proper operation of P/M 500).

FIG. 27 is a detailed view of register block 537 of FIG. 26. Register block 537 includes four registers: FLAG-REG, TEMP1-REG, TEMP2-REG, AND STATUS-REG. FLAG-REG bits indicate whether certain conditions of both ITGS 10 and P/M 500 have occurred or have not occurred, or which states ITGS 10 and P/M 500 are in. The structure of FLAG-REG will be discussed in more detail below in conjunction with FIG. 28. TEMP1-REG and TEMP2-REG are used for temporary storage of the UP-LINK during execution of the Read UP-LINK subprogram which is discussed below in conjunction with FIG. 41. STATUS-REG stores the status of ITGS 10 as derived from the UP-LINK during execution of the Read UP-LINK subprogram.

FIG. 28 is a detailed description of the character of each bit position of FLAG-REG. The "'ON/OFF'" bit is set if ITGS 10 is in the "on" state. The "IMPLANTED" bit is set if ITGS 10 is implanted (derived from data input during execution of the Program of FIG. 35) in a body. The "IMPLANT FOUND" bit is set if communications between ITGS 10 and P/M 500 have been established by the reception of an UP-LINK transmitted in response to a DOWN-LINK. The state ("set" or "not set") of the "'ON/OFF'" and "IMPLANTED" bits is determined from the UP-LINK received during execution of the Read UP-LINK subprogram discussed below in conjunction with FIG. 41.

Still referring to FIG. 28, "BATTERY EOL" is set if the 9 volt battery powering P/M 500 is at its "end of life" as discussed above. "BATTERY LOW" is set if the 9 volt battery powering P/M 500 is "low" as discussed above. "MEMORY O.K." is set if the circuit within control circuit 518 (FIG. 26) comprising processor 528, decoder 540 and memory 534 is not functioning properly. "PROCESSOR O.K." is set if processor 528 is not functioning properly. "CIRCUIT VOLTAGE O.K." is set if any of the voltages at certain nodes of the circuitry of FIG. 24 are not at a proper level. "COMMUNICATIONS CIRCUITRY O.K." is set if the transmit/receive circuit 514 or its interface with control circuit 518 is not functioning properly. The state of the above six bits is determined during execution of the Self Diagnostic subprogram discussed below in conjunction with FIG. 38.

Again referring to FIG. 28, "KEY1 PRESSED" is set if and when KEY1, i.e., push-button 506, is pressed in response to a function selection prompt on display 504. "KEY2 PRESSED" is set if and when KEY2, i.e., push-button 508, is pressed in response to a function selection prompt on display 504. The state of the above two bits is determined during execution of the Get Keypress subprogram discussed below in conjunction with FIG. 39.

Figure 29A:
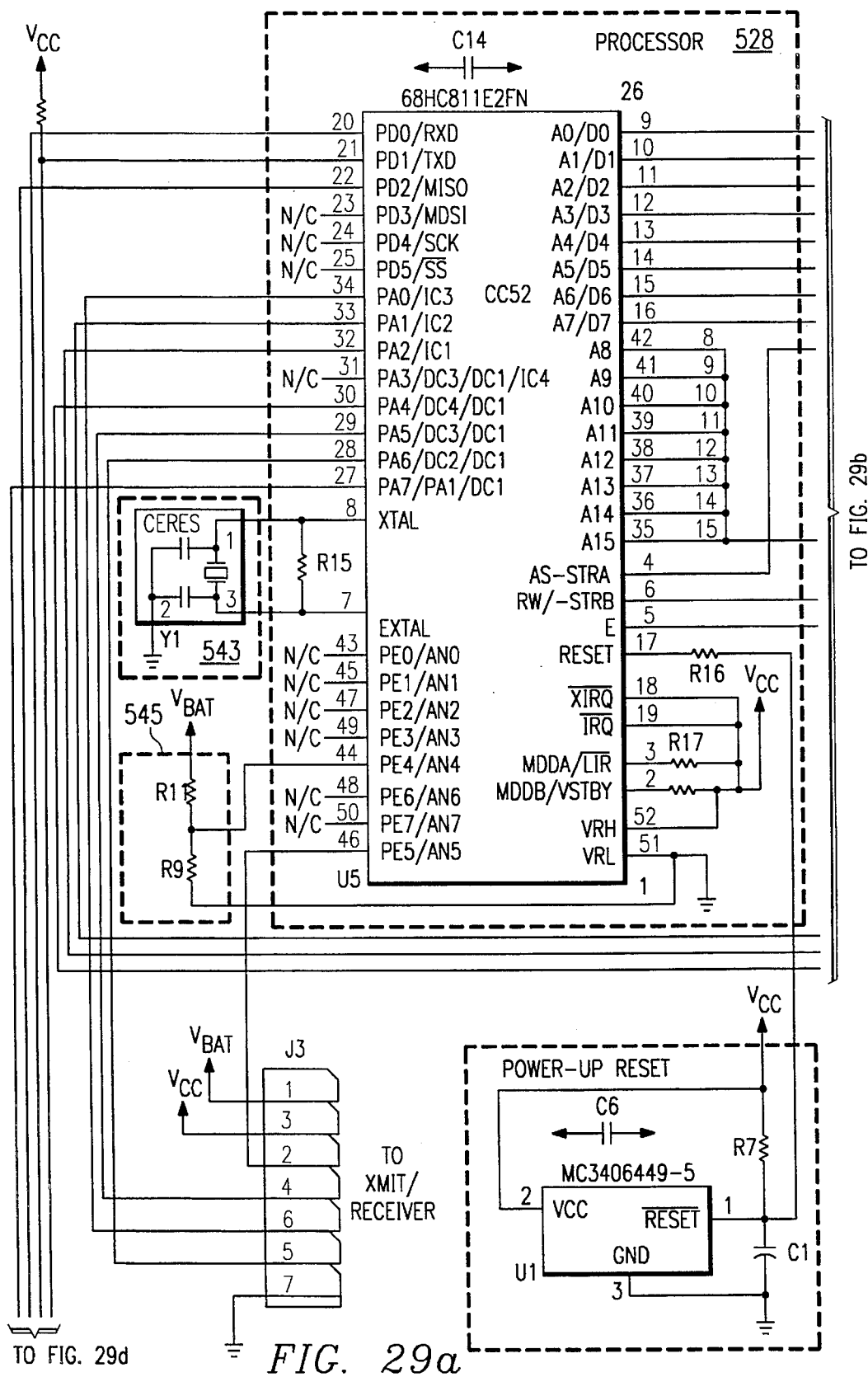
FIG. 29a–d are detailed schematic of one embodiment of the power circuit of FIG. 25 and the control circuit of FIG. 26.

FIGS. 29a–d is a detailed schematic of the preferred embodiment of power circuit 516 and control circuit 518. FIG. 29a shows processor 528 and its peripheral circuitry. In this embodiment, processor 528 is a Motorola 6811, although other embodiments may use other processors. Battery voltage test circuit is shown in this embodiment to consist of a resistive voltage divider for providing the test voltage to processor 528. Here, processor 528 has an internal Analog-To-Digital Converter (not shown) for converting the analog test voltage into a digital word for internal processing by processor 528. Also shown are the implementations of crystal oscillator circuit 543 and the power-up reset circuit.

Figure 29B:
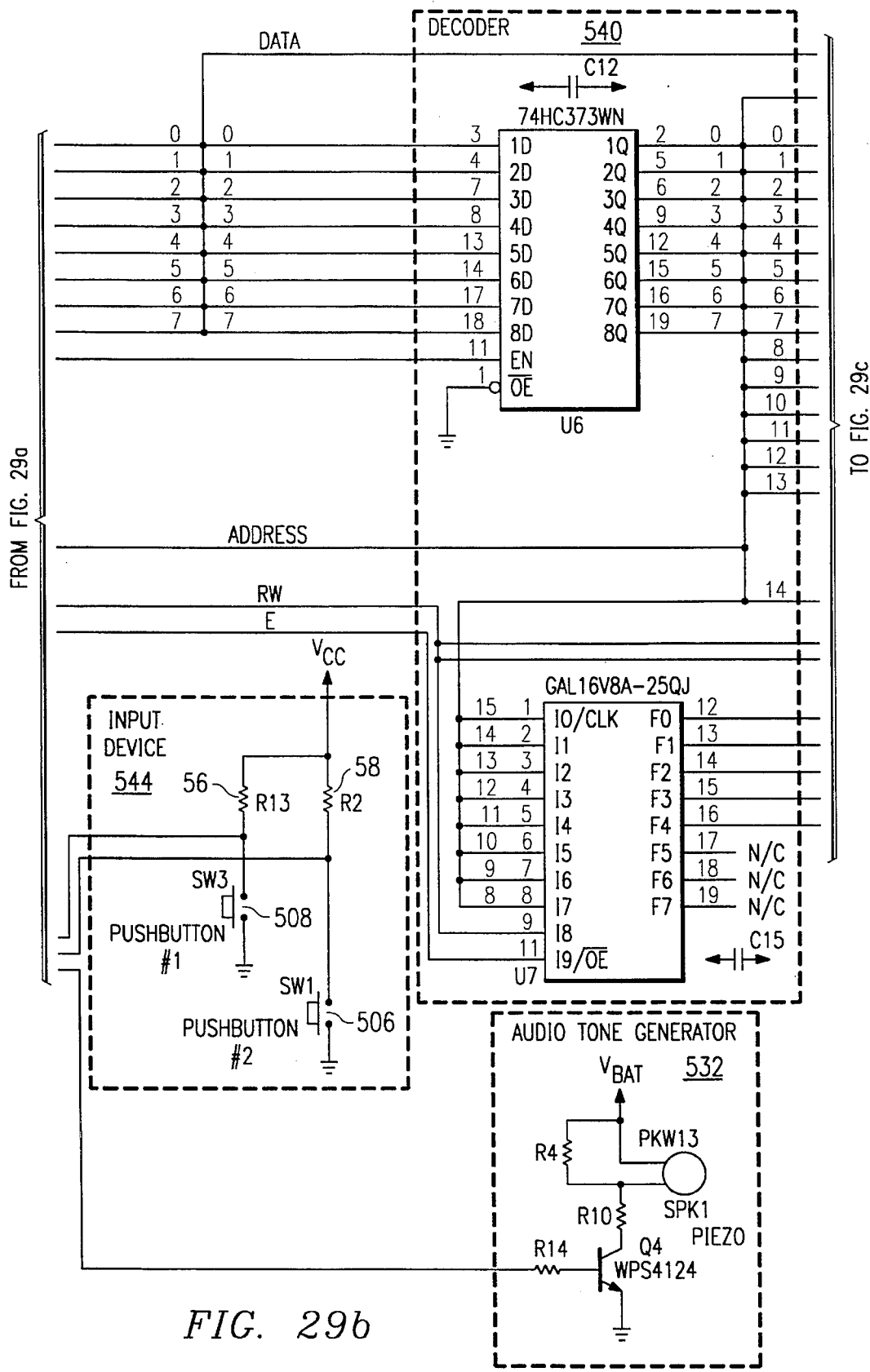

FIG. 29b shows decoder 540. In this embodiment, decoder 540 consists of 74HC373 latch interconnected with a 16V8 PAL. Audio tone generator 532 is shown to include a transistor coupled to a piezoelectric device for audible sound generation. Input device 544 is shown to include both push-buttons 506 and 508. Both push-buttons are of the type which electrically close when pressed and are electrically open when not pressed. As discussed above, two function choices of the interactive menu are displayed at one time on display 504. Push button 506, i.e., KEY1, when pressed, signals processor 528 that the first choice has been selected. Likewise, push-button 508, i.e., KEY2, when pressed, signals processor 528 that the second choice has been selected.

Figure 29C:
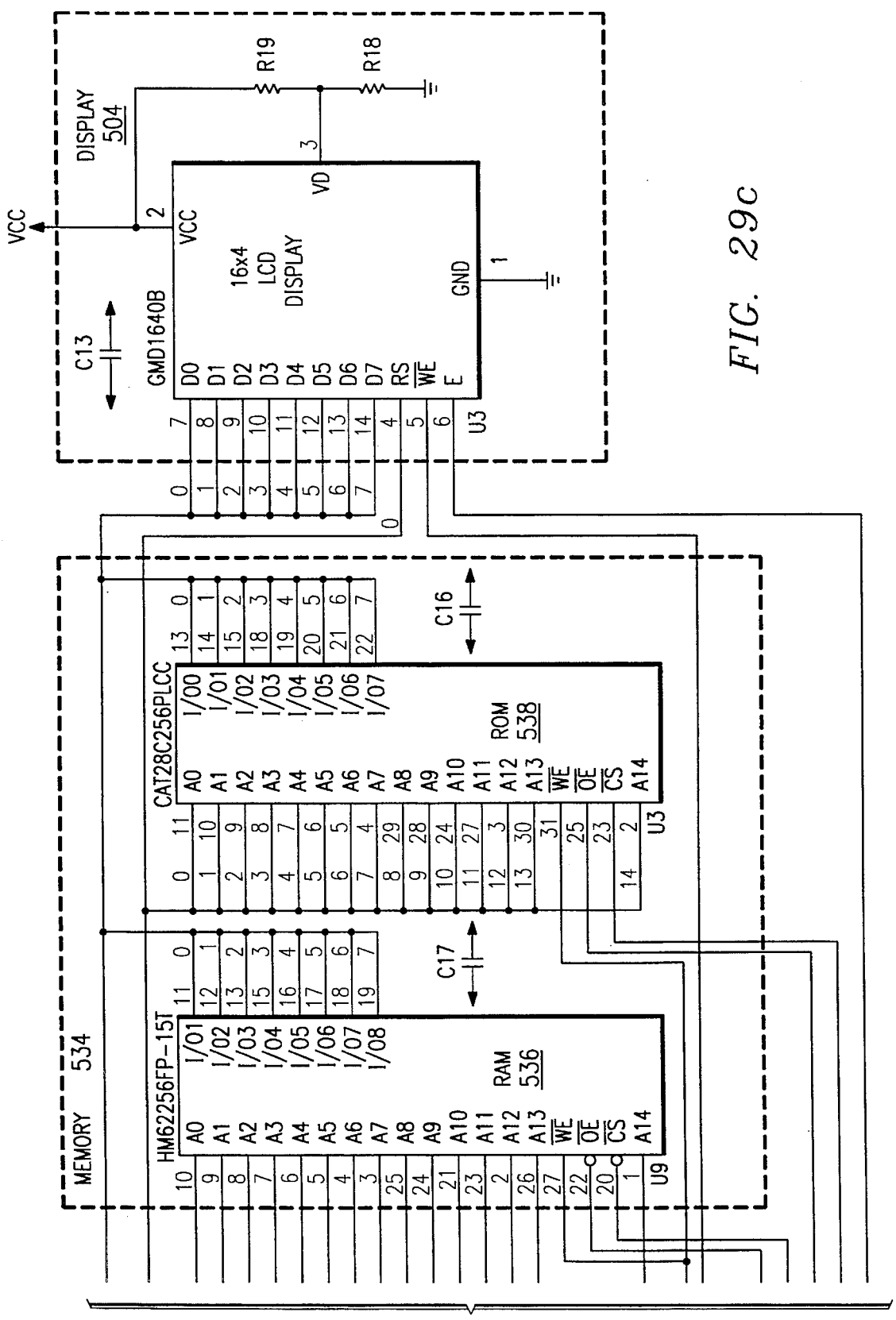

FIG. 29c shows memory 534 consisting of an HH62256 Ram as RAM 536 and a CAT28C256 EEPROM as ROM 538. Display 504 comprises a GND16-406 16×4 LCD display.

Figure 29D:
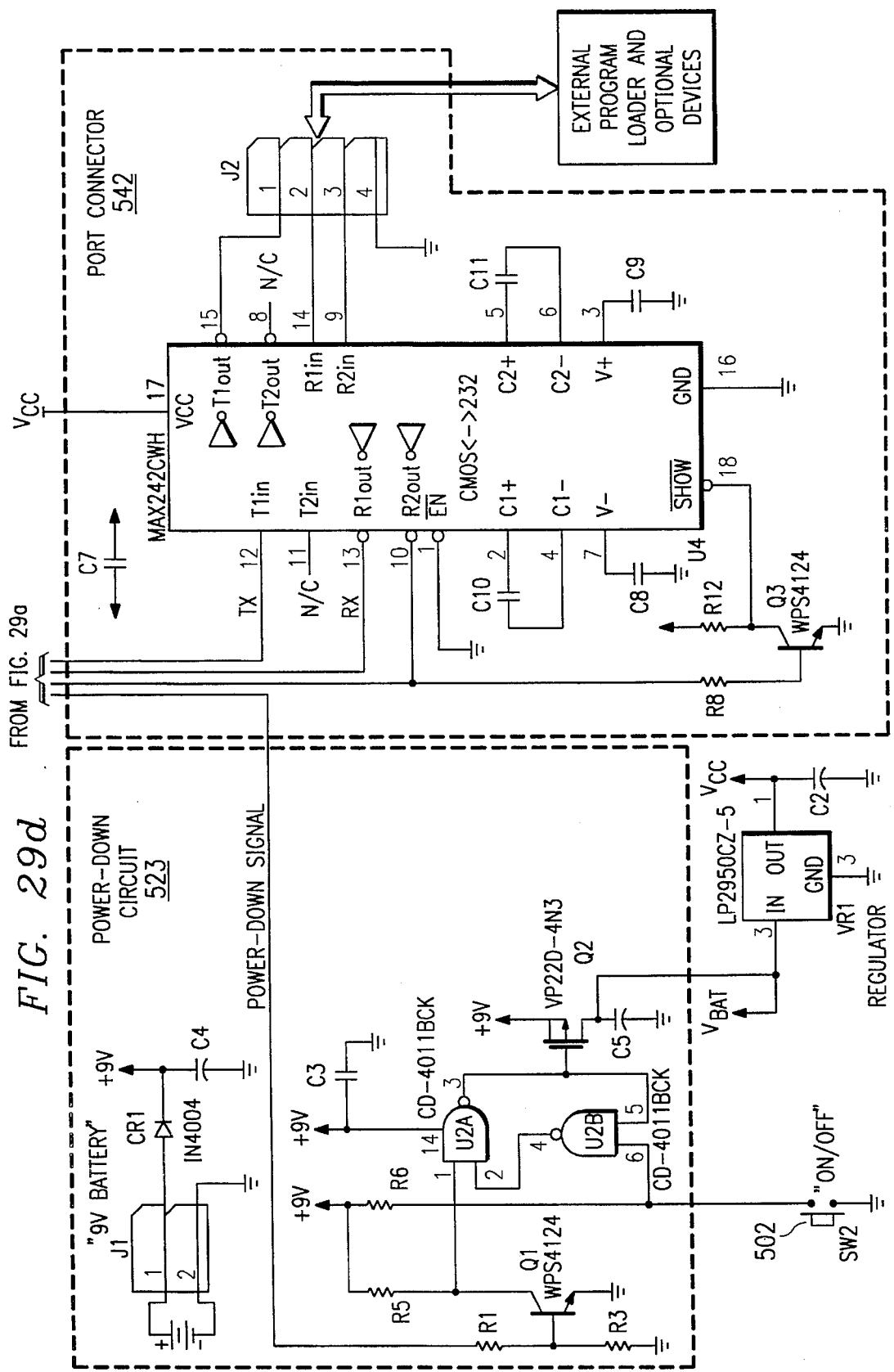

FIG. 29d shows a MAX242 device used for port connector 542. The circuit implementation of power-down circuit 523 is also shown. The two NAND gates form a flip-flop. When the output of the flip-flop is low voltage, i.e., approximately ground or 0 volts, transistor Q2 closes and conducts to provide VBat. When the power-down signal is generated by processor 528, transistor Q1 conducts and toggles the output of the flip-flop to a high voltage, i.e., approximately 9 volts. Thus, transistor Q2 opens, ceases to conduct and VBat is no longer provided. P/M 500 is now "off" until "on" switch 502 is pressed.

c. Transmit/Receive Circuit

FIG. 30 is a more detailed view of transmit/receive circuit 514. Transmit module 520 receives the DOWN-LINK from control circuit 518 and conditions the DOWN-LINK for transmission via antenna 521 to the ITGS 10. Receive module 522 receives the UP-LINK via antenna 521 from ITGS 10 and conditions the UP-LINK for processing by control circuit 518. Some embodiments of receive module 522, as discussed below, also receive the DISABLE signal from control circuit 518. Transmit module 520 and receive module 522 will be discussed in more detail below in conjunction with FIGS. 31–34.

i. Preferred Embodiment

FIG. 31 is a block diagram of the preferred embodiment of transmit/receive circuit 514 of FIG. 30. Transmit module 520 includes a pulse generator 546 which receives from processor 528 the DOWN-LINK which comprises a series of pulses as described above in conjunction with FIG. 9b. The DOWN-LINK from processor 528 is a signal in digital form, i.e., the digital DOWN-LINK. Pulse generator 546 amplifies the DOWN-LINK and feeds the DOWN-LINK to a transmit coil 548 of antenna 521. The DOWN-LINK from pulse generator 546 is a signal in analog form, i.e., the analog DOWN-LINK. The DOWN-LINK transmitted from transmit coil 548 is a signal in electromagnetic form, i.e., the electromagnetic DOWN-LINK. Transmit coil 548 is powered by voltage $V_{cc}$. Antenna 521 also includes a receiver coil 550, powered by voltage $V_{Bat}$, for coupling the electromagnetic UP-LINK, radiated from ITGS 10 as described above in conjunction with FIG. 14, to receiver module 522. In this embodiment, transmit coil 548 and receive coil 550 are wound on the same bobbin, i.e., core, although in other embodiments each of the coils 548 and 550 may be wound on separate cores.

Receiver module 522 includes a clipper circuit 552, powered by voltage $V_{cc}$, for limiting the peak excursions of the analog UP-LINK coupled by receiver coil 550. A disable circuit 554 powered by voltage $V_{cc}$, acts as a switch responsive to a DISABLE signal from processor 528 to uncouple any received signal from the input of AC coupler 556. Otherwise, the AC coupled signal is fed from the output of AC coupler 556 to the input of a differential amplifier 558, which is powered by voltages Vcc and Vg. The amplified signal is then fed via an AC coupler 559 to an inverting amplifier 560, powered by voltages Vcc and Vg, which outputs the UP-LINK in a digital form. The digital UP-LINK is then coupled to processor 528 of FIG. 26 for further processing. In this embodiment of receiver module 522, differential amplifier 558 and inverting amplifier 560 each have a gain of 15, although in other embodiments, either differential amplifier 558, inverting amplifier 560, or both may have gains other than 15.

FIG. 32 is a detailed schematic of transmit/receive circuit 514 of FIG. 31. Pulse generator 546 includes a transistor 562 coupled between voltage $V_g$ and transmit coil 548. The gate of transistor 562 is driven by the digital DOWN-LINK from processor 528. Clipper circuit 552 includes two diodes in parallel as shown. Disable circuit 554 comprises a transistor acting as a switch, while AC couplers 556 and 559 each comprise a single capacitor. Differential amplifier 558 comprises an operational amplifier configured as a differential amplifier, while inverting amplifier 560 comprises an operational amplifier in an inverting configuration.

A) Operation of Preferred Embodiment

In operation of transmit/receive circuit 514 of FIGS. 31 and 32, processor 528 (FIG. 26) sends the DOWN-LINK, in digital form, to pulse generator 546. As discussed above, the digital DOWN-LINK consists of a series of pulses. Transistor 562 acts like a switch and closes for the duration of each digital DOWN-LINK pulse. When transistor 562 is closed, one end of transmit coil 548 is coupled to voltage Vg (ground). A pulse of current flows through transmit coil 548 during the time transistor 562 is closed. This pulse of current causes transmit coil 548 to radiate an electromagnetic pulse. A series of electromagnetic pulses are radiated, one for each pulse in the digital DOWN-LINK. Thus, the electromagnetic DOWN-LINK is generated. Under normal conditions, the electromagnetic DOWN-LINK is received by ITGS 10 (FIG. 1) as described above. Requirements for normal conditions include having P/M 500 (FIG. 23) close enough to the receiver 64 (FIG. 18) of ITGS 10 so that the attenuation of the electromagnetic pulses forming the electromagnetic DOWN-LINK is small enough to insure reception. This may require antenna housing 510 (FIG. 23) to be aimed toward ITGS 10.

ITGS 10 processes the received electromagnetic DOWN-LINK and then transmits back to P/M 500 (FIG. 23) the electromagnetic UP-LINK, which also comprises a series of electromagnetic pulses, as described above. Again under normal conditions, each pulse of the electromagnetic UP-LINK will induce a pulse of voltage across receive coil 550. These induced pulses form the analog UP-LINK.

Each analog pulse of voltage across receive coil 550 is then "clipped" by clipper circuit 552. Clipper circuit 552 comprises a pair of parallel diodes which centers each analog pulse of the analog UP-LINK around $V_{cc}$ and limits the peak excursion of each pulse analog to between $V_{cc}-0.7$ volts and $V_{cc}+0.7$ volts. Typically, each analog pulse at the input of clipper circuit 552 has an amplitude of approximately 4 microvolts superimposed on $V_{cc}$. Each "clipped" analog pulse is then fed to AC coupler 556. AC coupler 556 comprises a capacitor which blocks, i.e., filters, the DC component of the "clipped" analog pulses which is equal to $V_{cc}$. Each analog pulse output from AC coupler 556 has a peak excursion between −0.7 volts and +0.7 volts. (Each pulse is centered around approximately 0 volts instead of $V_{cc}$ since $V_{cc}$ has been filtered from the signal.)

Each analog pulse of the analog UP-LINK is then amplified by differential amplifier 558 which, as discussed above, has a gain of approximately 15. Each amplified analog pulse is then fed to AC coupler 559. In the same fashion as AC coupler 556, the capacitor making up AC coupler 559 blocks any DC component given to the amplified analog pulses by differential amplifier 558. Each pulse is then fed to inverting amplifier 560. Inverting amplifier 560 converts each analog pulse into a digital pulse whose logic leads are compatible with processor 528 (FIG. 26). Thus, inverting amplifier 560 generates the digital UP-LINK. Here, a low level, or logic "0", is represented by a voltage of approximately $V_g$, and a high level or logic "1" is represented by a voltage of approximately Vcc. Each digital pulse of the digital UP-LINK is then fed to processor 528 for processing.

ii. Alternate Embodiment

Figure 33:
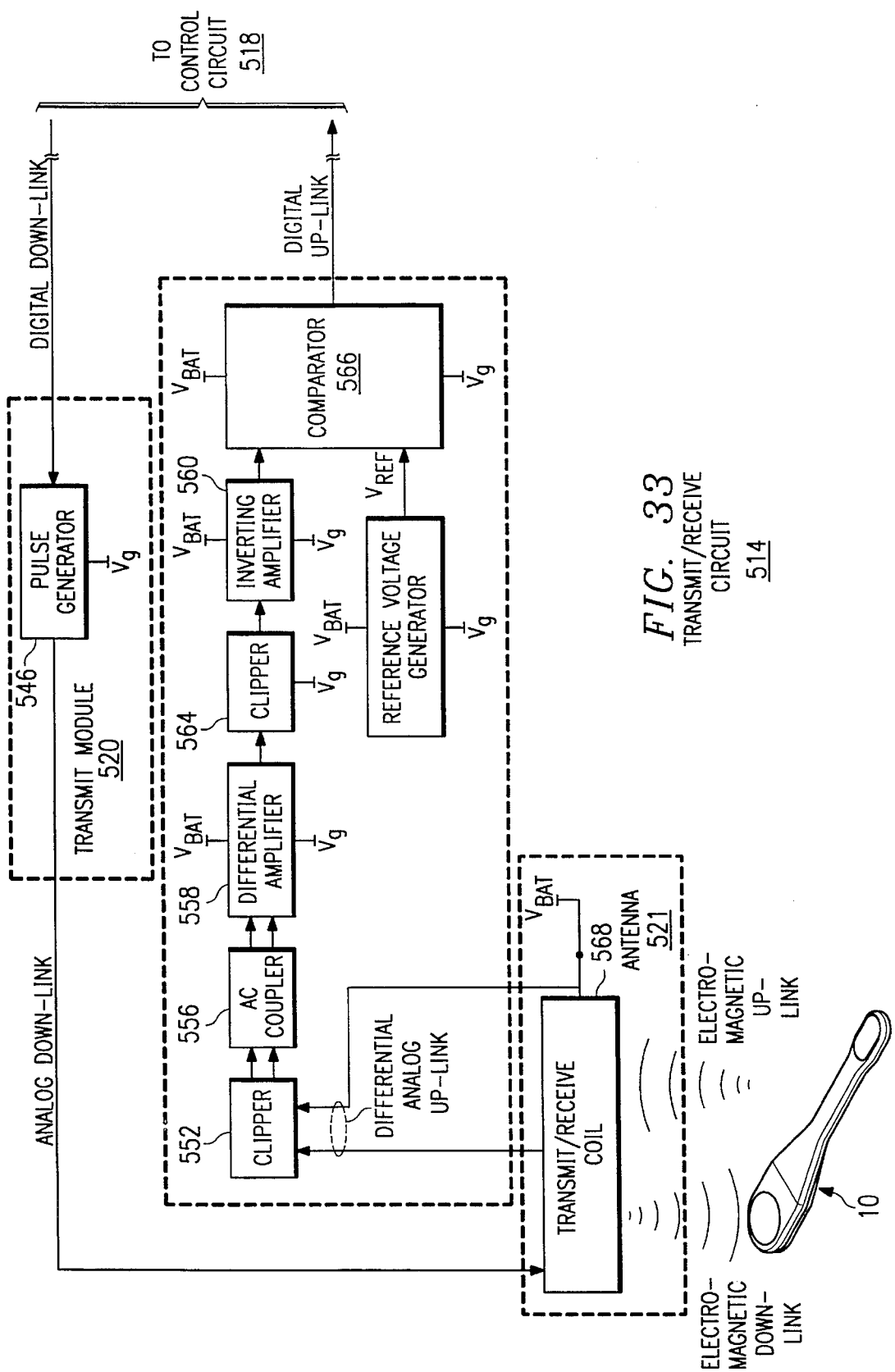
FIG. 33 is a block diagram of an alternate embodiment of the transmit/receive circuit of FIG. 30.

FIG. 33 is a block diagram of an alternative embodiment of transmit/receiver module 514 of FIG. 30. Pulse generator 546 amplifies the digital DOWN-LINK and couples the digital DOWN-LINK to one end of a transmit/receive coil 568. Transmit/receive coil 568 is a single coil which is used both to transmit the electromagnetic DOWN-LINK and to receive the electromagnetic UP-LINK. The opposite end of transmit/receive coil 568 is coupled to voltage VBat. Both ends of transmit/receive coil 568 are differentially coupled to clipper circuit 552. Clipper circuit 552 differentially limits the peak excursions of the analog UP-LINK. The differentially clipped analog UP-LINK is differentially fed to AC couple circuit 556. The differential output of AC couple circuit 556 is differentially fed to differential amplifier 558. Differential amplifier 558 converts the differential input into a single-ended output. A clipper circuit 564 limits the peak excursions of the single-ended output from differential amplifier 558 and couples the analog UP-LINK to the input of inverting amplifier 560. The output from inverting amplifier 560 is fed to a first input of a comparator 566. A reference voltage generator provides a reference voltage Vref which is coupled to a second input of comparator 566. Comparator 566 generates the digital UP-LINK which is fed to processor 528 (FIG. 26).

FIG. 34 is a detailed schematic of the alternative embodiment of FIG. 33. Clipper circuit 552 comprises two diodes coupled in parallel across the differential input and output of clipper circuit 552. AC coupler 556 includes two capacitors, each one serially coupled to a different one of the two differential input/output lines. Differential amplifier 558 comprises an operational amplifier which amplifies the differential analog UP-LINK and converts it into a single-ended signal. Clipper circuit 564 comprises two parallel diodes which "clip" the single-ended signal. Inverting amplifier 560 comprises an operational amplifier in an inverting configuration which amplifies and inverts the "clipped" signal. Comparator 566 consists of a comparator which compares the analog UP-LINK output from inverting amplifier 560 with a voltage Vref. Reference voltage generator 562 comprises a resistive voltage divider which generates Vref from VBat. The digital UP-LINK is output from comparator 566.

A) Operation of Alternative Embodiment

Referring to FIGS. 33 and 34, the alternative embodiment of transmit/receive circuit 514 operates similarly to the preferred embodiment of FIGS. 31 and 32. One major difference is that transmit/receive coil 568 acts as both a transmit coil and a receive coil. Another major difference is that the analog pulses of voltage induced by the electromagnetic UP-LINK across transmit/receive coil 568 are differentially coupled through to differential amplifier 558. These differentially coupled analog pulses form the differential analog UP-LINK. One advantage of differential coupling is that it is less sensitive to common mode voltage and current fluctuations than is single line coupling.

Still referring to FIGS. 33 and 34, each analog pulse of the differential analog UP-LINK induced across transmit/receive coil 568 is differentially coupled to clipper circuit 552. Clipper circuit 552 restrains the differential voltage excursion of each analog pulse to between ±0.7 volts. Each analog pulse is then differentially AC coupled by the two capacitors of AC coupler 556. AC coupler 556 removes any DC voltage component from the differentially coupled pulses.

Each analog pulse is then differentially coupled to differential amplifier 558 which converts each pulse from a differential signal to a single ended signal. The single ended analog pulses are then fed to clipper circuit 564 which "clips" the peak excursion of each analog pulse to between ±0.7 volts. Each "clipped" analog pulse is converted to a digital pulse by the combination of inverting amplifier 560 and comparator 566. Thus, the digital UP-LINK is generated at the output of comparator 566. As described above in conjunction with FIGS. 31 and 32, each digital pulse of the digital UP-LINK is compatible with processor 528 (FIG. 26). Each digital pulse of the digital UP-LINK is fed to processor 528 for processing.

2. Programming/Monitoring of ITGS

FIG. 35 illustrates, in flow chart form, the interactive operation of P/M 500 (FIG. 23). The normal, single-bordered blocks represent the stated operation performed by P/M 500. Bold single-bordered blocks indicate the execution by processor 528 of a subprogram whose operation is discussed in more detail below in conjunction with another FIGURE. Double-bordered boxes show the contents of display 504 at that particular point in the flow chart. The diamond boxes represent a decision to be made by processor 528 at that point of the program or subprogram.

Referring to FIG. 35, the flow chart of the P/M Program executed by processor 528 is illustrated. P/M 500 is switched "on" with power "on" switch 502. Immediately, processor 528 executes a Power-Up subprogram. The Power-Up subprogram is discussed in detail in conjunction with FIG. 36. The flags within FLAG-REG (FIG. 28) are then initialized to "not set".

Display 504 prompts for input signalling whether ITGS 10 should be toggled "on" or "off" (depending upon its present state) or whether ITGS 10 should be tested. The first choice, "TEST IMPLANT" is selected by pressing, pushbutton 506 (KEY1), while the second choice, "TURN IMPLANT ON/OFF", is selected by pressing push-button 508 (KEY2). After displaying the above selection choices, processor 528 executes a Get Keypress subprogram to determine which key is pressed, and hence, whether ITGS 10 is to be tested or toggled "on/off". The Get Keypress subprogram is discussed in detail below in conjunction with FIG. 39. TEMP1-REG, representing whether ITGS 10 is to be tested or toggled "on/off", is then set to indicate the latter or not set to indicate the former.

Display 504 prompts for input data, signaling whether ITGS 10 is presently implanted or not, by displaying "IS DEVICE IMPLANTED? YES/NO". "YES" is selected by pressing push-button 506 and "NO" is selected by pressing push-button 508 as described above. The Get Key Press subprogram, as described above, determines which response is chosen, and the flag in "IMPLANTED" FLAG-REG is set only if the received input data indicates ITGS 10 is implanted.

A message "PLACE MONITOR OVER IMPLANT" instructing that P/M 500 be placed over ITGS 10 (or over the area where ITGS 10 is implanted), is displayed on display 504. As discussed previously, antenna housing 501 typically needs to be facing in the general direction of ITGS 10 in order that ITGS 10 and P/M 500 may communicate with each other. The details of transmission and reception in both P/M 500 and ITGS 10 are discussed above.

If ITGS 10 is to be toggled "on/off", P/M 500 transmits the proper DOWN-LINK (FIG. 9*b*) instructing ITGS 10 to transmit back its status via the UP-LINK (FIG. 9*c*). If the UP-LINK is not received by P/M within a reasonable time (here, 2 seconds) processor 528 returns to the Initialize Flags subprogram as shown. If the UP-LINK is received, processor 528 executes an Implant ON/OFF subprogram to determine whether ITGS 10 is presently "on" or "off". If "on", P/M 500 transmits a DOWN-LINK instructing ITGS 10 to turn "off". If ITGS 10 is presently "off", P/M 500 transmits a DOWN-LINK instructing ITGS 10 to turn "on". Processor 528 then returns to the Initialize Flags subprogram.

If a test of ITGS 10 is to be performed, processor 528 executes an Implant Test subprogram as shown. The Implant Test subprogram is discussed in detail below in conjunction with FIG. 40. Processor 528 then returns to the Initialize Flags subprogram as shown.

Figure 36:
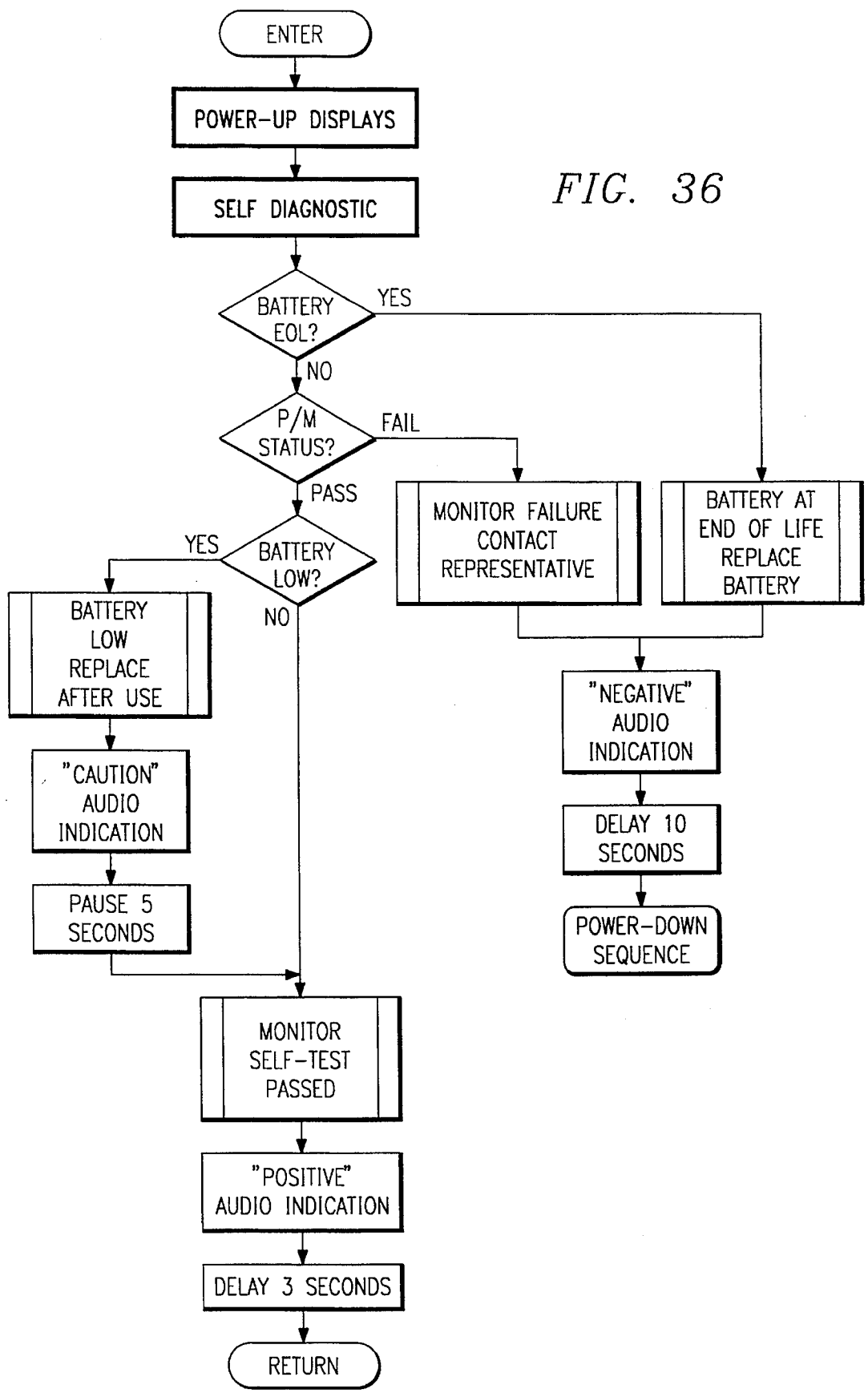
FIG. 36 is a flow chart of the Power-Up subprogram of FIG. 35.

FIG. 36 is a flow chart of the Power-Up subprogram of FIG. 35. Processor 528 first executes a Power-Up Displays subprogram. This subprogram is executed immediately after P/M 500 is switched "on". The Power-Up Displays subprogram is discussed in detail below in conjunction with FIG. 37. Processor 528 then executes a Self Diagnostic subprogram, which is discussed in detail below in conjunction with FIG. 38.

Next, processor 528, determines whether or not the 9 volt battery supplying $V_{Bat}$ is at the end of its useful life by reading the "Battery EOL (end of life)" flag in FLAG-REG. In this embodiment, battery "end-of-life" occurs when $V_{Bat}$ falls below a predetermined "end-of-life" threshold. If the "Battery EOL" flag is set, display 504 displays "BATTERY AT END OF LIFE REPLACE BATTERY". A "negative" audio tone, generally indicating a problem has occurred, is generated by audio tone generator 532 for approximately 10 seconds. Processor 528 then executes a Power-Down subprogram by sending a power down signal to power down circuit 523 to power down, i.e, turn "off", P/M 500.

If the "Battery EOL" flag is not set, processor 528 determines whether any of the P/M status flags have been set. If any of these flags are set, "MONITOR FAILURE CONTACT REPRESENTATIVE" is displayed on display 504. The "negative" audio tone is generated for approximately 10 seconds and processor 528 executes the Power-Down subprogram.

If none of the P/M status flags are set, processor 528 determines if the "Battery Low" flag is set. If set, "BATTERY LOW REPLACE AFTER USE" appears on display 504. Audio tone generator 532 generates a "caution" audio tone, which is discernable from the "negative" audio tone, for approximately 5 seconds. If the "Battery Low" flag is not set (or if it is, after the "caution" tone is generated), "MONITOR SELF-TEST PASSED" appears on display 504. A "positive" audio tone, discernable from both the "negative" and "caution" tones, is generated for approximately 3 seconds. Processor 528 then exits the Power-Up subprogram.

Figure 37:
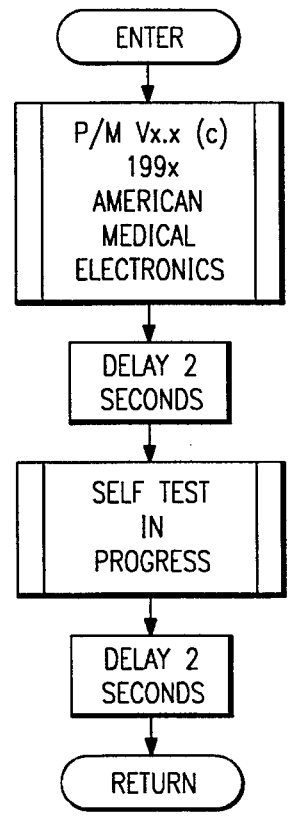
FIG. 37 is a flow chart of the Power-Up Displays subprogram of FIG. 36.

FIG. 37 is a flow chart of the Power-Up Displays subprogram of FIG. 36 When P/M 500 is switched "on", "P/M Vx.x (c) 199x AMERICAN MEDICAL ELECTRONICS" appears on display 504. This message indicates the software version of the program and subprograms which P/M 500 is executing, the year the software version was published, and the manufacturer. The aforementioned display is generated for approximately 2 seconds, then "SELF TEST IN PROGRESS" appears on display 504 for approximately 2 seconds. This message indicates that processor 528 is executing the Self Diagnostic subprogram of FIG. 38.

Figure 38:
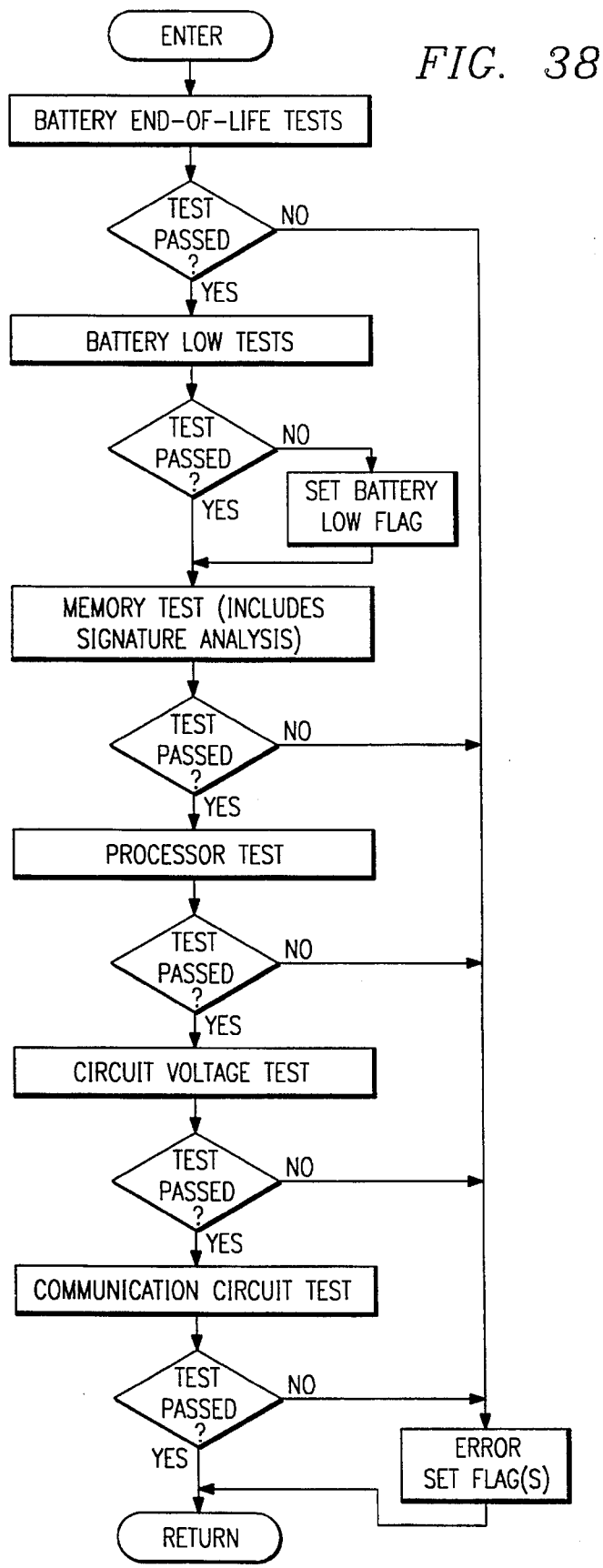
FIG. 38 is a flow chart of the Self Diagnostic subprogram of FIG. 36.

FIG. 38 is a flow chart of the Self Diagnostic subprogram of FIG. 36. Six tests are performed in a serial fashion. The first test performed is the Battery "End of Life" test. This test is performed by processor 528. Processor 528 converts the analog test voltage provided by battery voltage test circuit 545 (FIG. 26) into a digital word and from this digital word determines whether or not $V_{Bat}$ is above or below a predetermined "end of life" threshold. If $V_{Bat}$ is above this threshold, then the 9 volt battery is not at its "end of life" and the test is passed. If $V_{Bat}$ is below this threshold, the battery is at its "end of life", needs to be replaced, and the test is failed. If the 9 volt battery fails this test, the "Battery EOL" flag in FLAG-REG is set and the Self Diagnostic subprogram is exited.

If the battery passes the Battery "End Of Life" test, the Battery "Low" test is performed. The Battery Low test is performed by processor 528 in a way almost identical to that of the Battery "End Of Life" test. The only difference is that the predetermined battery "low" threshold is higher than the "end of life" threshold. If $V_{Bat}$ is below the battery "low" threshold (but above the battery "end of life" threshold), it is still high enough for proper operation of P/M 500, but it is likely that the 9 volt battery will soon need to be replaced. If the battery "low" test is failed, the "BATTERY LOW" flag in FLAG-REG is set. If the battery "low" test is passed, no flag in FLAG-REG is set. Processor 528 then continues on to the next test.

The remaining four test subprograms are collectively called the "P/M STATUS" tests, because they each test the status of a different component of the internal circuitry of P/M 500. The Memory test checks memory 534 of FIG. 26. During this test, various circuit components, such as memory 534, are tested to insure their proper functioning. For example, processor 528 may write a particular word to a particular register of RAM 536. Processor 528 would then read the same register and see if the contents are identical to the particular word. If identity is established, communication pathways between processor 528 and the particular register are functioning properly. Every register of RAM 536 may be tested in this way to determine whether RAM 536 is functioning properly. Other circuit components may be similarly tested by processor 528 to verify their proper functioning. Tests of the aforementioned type are well known and will, therefore, not be discussed in detail here. If memory 534 is not functioning properly, the test is failed. The "MEMORY O.K." flag of FLAG-REG is set, and processor 528 exits the Self Diagnostic subprogram.

If memory 534 is functioning properly, the Memory test is passed, and processor 528 executes the Processor test, during which processor 528 actually checks its own internal circuit components for proper functioning. Each processor has its own unique processor test which is either provided by the processor manufacturer or executed automatically by the processor when commanded to do so. Therefore, the specifics of the Processor test need not be discussed here in detail. If processor 528 fails the Processor test, the "PROCESSOR O.K." flag of FLAG-REG is set, and processor 528 exits the Self Diagnostic subprogram.

If processor 528 passes the Processor test, the Circuit Voltage test is next executed. During this test, processor 528 measures the voltage at predetermined circuit nodes within transmit (receive circuit 514, power circuit 516, and control circuit 518 of FIG. 24). If the voltage at a certain node is not at its proper level, a problem, such as a short or open circuit, is indicated. Processor 528 sets the "CIRCUIT VOLTAGE O.K." flag in FLAG-REG and exits the Self Diagnostic subprogram.

If the Circuit Voltage test is passed, processor 528 executes the Communications Circuit test. This test checks for proper functioning of transmit/receive circuit 514. For example, processor 528 simply transmits a DOWN-LINK via transmit/receive circuit 514. The receive portion of transmit/receive circuit 514 would then be monitored by processor 528 to see if the transmitted signal is received. That is, the actual signal transmitted is immediately received by the receiver if the transmit/receive circuit 514 is functioning properly. This differs from normal operation in that processor 528 is not receiving an UP-LINK from ITGS 10, but is simply receiving the DOWN-LINK it has sent. It is as if P/M 500 is short circuiting its transmit/receive circuitry 514 so that whatever is transmitted is also received. If processors 28 determines that it has received what it had transmitted, then transmit/receive circuit 514 is functioning properly. If transmit/receive circuit 514 is not functioning properly, processor 528 sets the "COMMUNICATIONS CIRCUIT O.K." flag in FLAG-REG and exits the Self Diagnostic subprogram. If transmit/receive circuit 514 is functioning properly, processor 528 exits the Self Diagnostic subprogram without setting any of the flags in FLAG-REG. By examining the contents of FLAG-REG, the cause of the P/M 500 failure can be determined.

Figure 39:
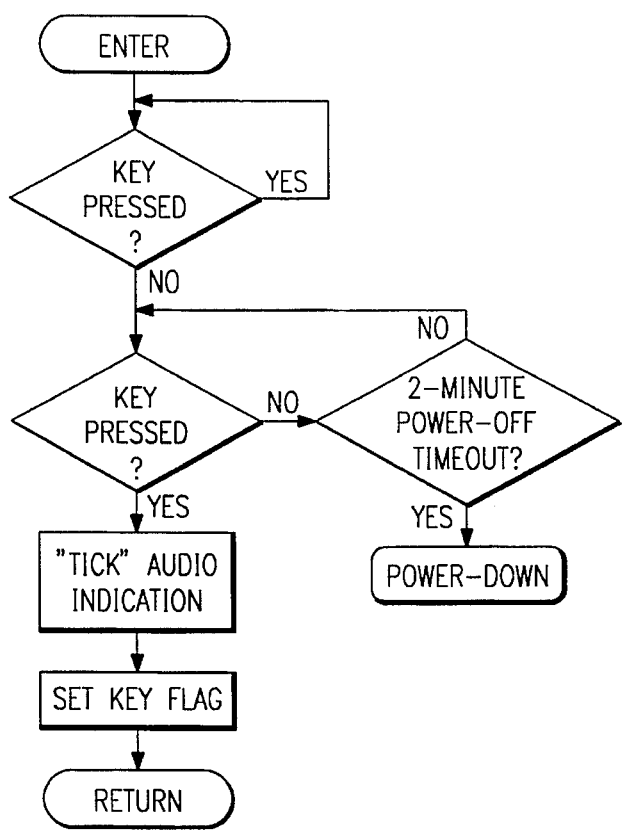
FIG. 39 is a flow chart of the Get Keypress subprogram of FIG. 35.

FIG. 39 is a flow chart of the Get Keypress subprogram of FIG. 35. The Get Keypress subprogram determines when and which "key" is pressed. As stated above, push-button 506 is "KEY1" and push-button 508 is "KEY2". Processor 528 begins executing the Get Keypress subprogram by reading the "KEY1" and "KEY2" flags in FLAG-REG. If one or both of the flags is set, processor 528 ignores this initial "key" press, and waits until the pressed "key" has been released before continuing. This prevents an inadvertent selection caused by a pressing of a "key" before the "SELECT: TEST . . . " prompt of FIG. 35 appears on display 504. Once the "key" is released, or if there was no initially pressed "key" processor 528 waits for a period of up to approximately 2 minutes for a "key" to be pressed, i.e., a selection of one of the function choices to be made. If no "key" is pressed within this time, processor 528 executes the POWER-DOWN subprogram P/M 500 by sending a POWER-DOWN signal to power-down circuit 523, thus shutting P/M 500 "off". Executing the Power-Down subprogram prevents needless power drain on the 9 volt battery when P/M 500 is inadvertently left "on". If a "key" is pressed within 2 minutes, audio tone generator 532 generates a "tick" sound to indicate a "key" has been pressed. Processor 528 sets the appropriate key flag in FLAG-REG and exits the Get Keypress subprogram.

Figure 40:
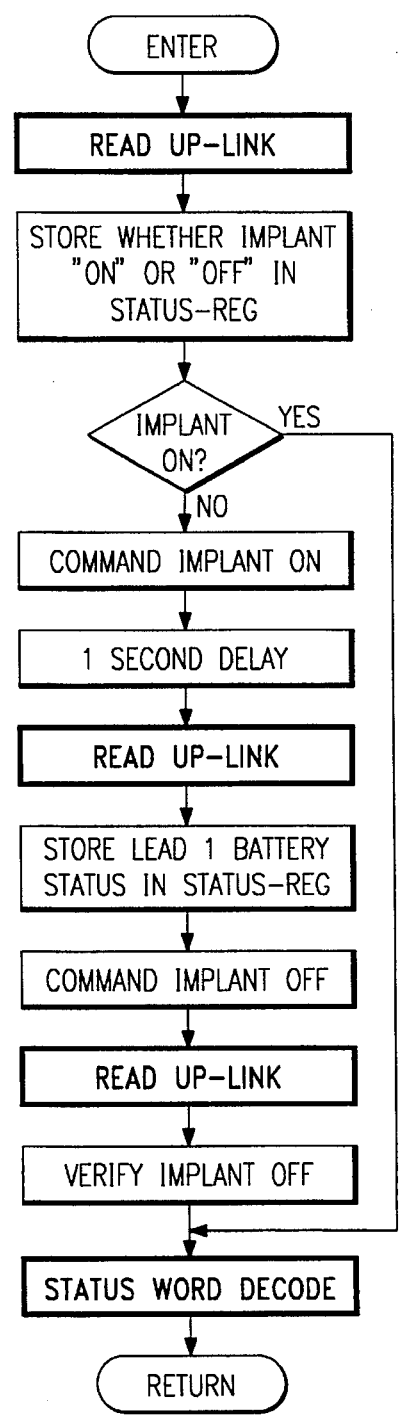
FIG. 40 is a flow chart of the Implant Test subprogram of FIG. 35.

FIG. 40 is a flow chart of the Implant Test subprogram of FIG. 35. Processor 528 first executes the Read UP-LINK subprogram in order to determine whether ITGS 10 is "on" or "off" (FIG. 9b). The Read UP-LINK subprogram is discussed further in conjunction with FIG. 41. Processor 528 then stores the 8 bits of the UP-LINK of FIG. 9c starting with STIM0 and ending with BATT1 in STATUS-REG (FIG. 27) to form a status word. If ITGS 10 is "on", processor 528 begins executing a Status Word Decode subprogram discussed in conjunction with FIG. 42.

If ITGS 10 is "off", processor 528 causes the generation and transmission of a DOWN-LINK with the appropriate values for STIM0 and STIM1 to turn "on" ITGS 10. Any one of the "on" modes shown in FIG. 9b is appropriate. Processor 528 delays for approximately 1 second before executing the Read UP-LINK subprogram. Processor 528 replaces the 6 bits of STATUS-REG starting with DCON and ending with BATT1 with the corresponding bits of the UP-LINK (FIG. 9c) received from ITGS. STIM0 and STIMi of status register, are not replaced. Processor 528 generates and causes the transmission of a DOWN-LINK instructing ITGS 10 to shut "off", thus returning ITGS 10 to the state it was in before processor 528 began executing the Implant Test subprogram. Processor 528 executes the Read UP-LINK subprogram and verifies that ITGS 10 is "off". Processor 528 begins execution of the Status Word Decode subprogram.

Figure 41:
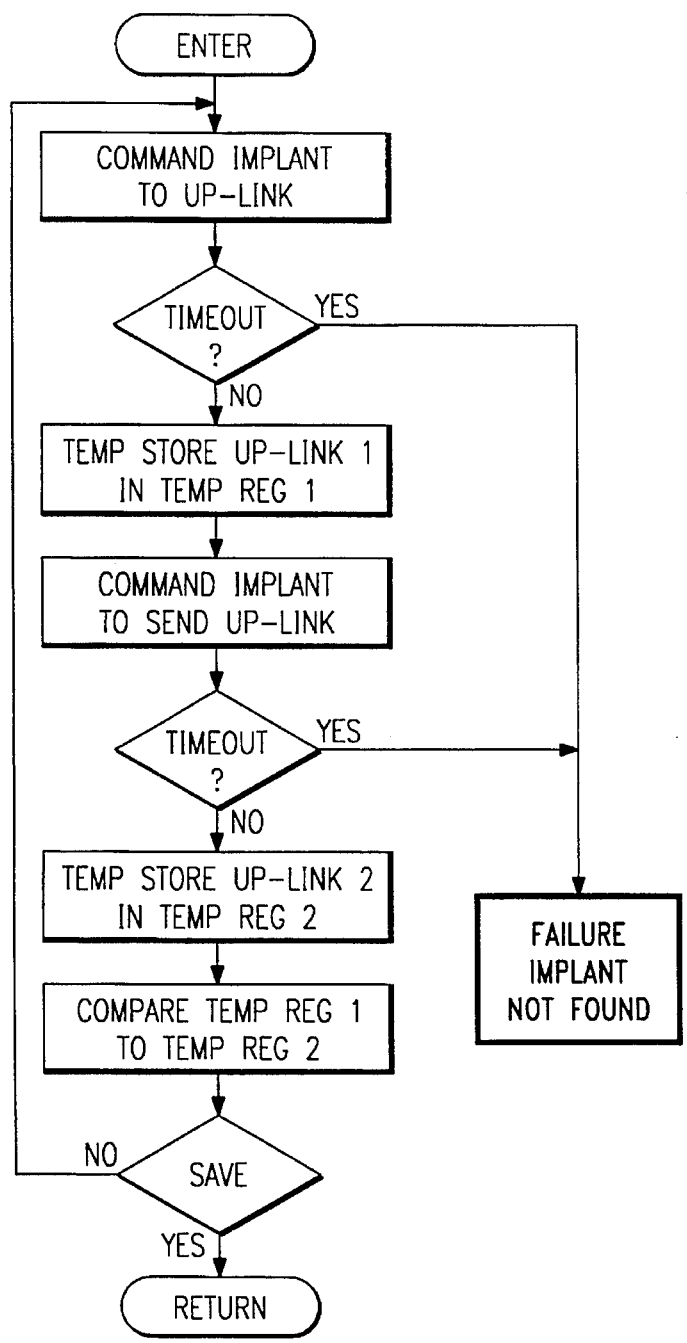
FIG. 41 is a flow chart of the Read UP-LINK subprogram of FIG. 40.

FIG. 41 is a flow chart of the Read UP-LINK subprogram. Processor 528 generates and causes the transmission of a DOWN-LINK instructing ITGS 10 to transmit an UP-LINK. If no UP-LINK is received within approximately 2 seconds, a timeout error occurs, and processor 528 begins executing the Implant Not Found subprogram described below in conjunction with FIG. 47. If an UP-LINK is received within the allotted time, processor 528 temporarily stores it in register TEMP1-REG (FIG. 27). Processor 528 then generates and causes transmission of a second DOWN-LINK instructing ITGS 10 to transmit a second UP-LINK. Again, if no UP-LINK is received within the allotted time, processor 528 begins executing the Implant Not Found subprogram. Normally, the second UP-LINK is received within the allotted time, and processor 528 stores it in register TEMP2-REG. Processor 528 then compares the contents of TEMP1-REG to TEMP2-REG. If the contents of TEMP1-REG and TEMP2-REG are not identical to one another, processor 528 begins executing the Read Up-Link subprogram from the beginning, because it is probable a communication error occurred during transmission or reception of one of the two UP-LINKS. Processor 528 will continue to execute the Read UP-LINK subprogram until a timeout error occurs or two consecutively received UP-LINKs are identical. Typically, two consecutively received UP-LINKS will be identical and processor 528 ends execution of the Read UP-LINK subprogram.

Figure 42:
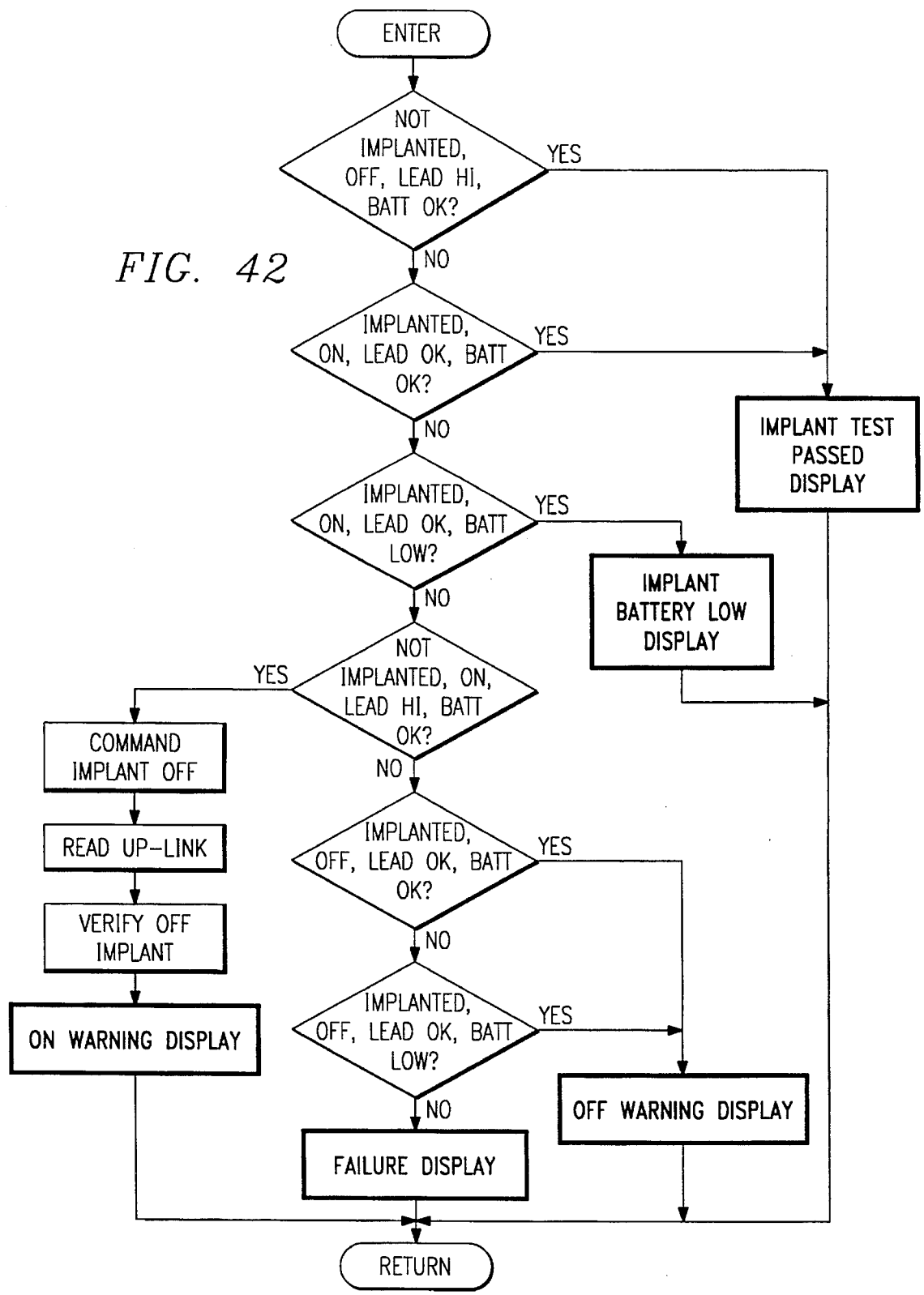
FIG. 42 is a flow chart of the Status Word Decode subprogram of FIG. 40.

FIG. 42 is a flow diagram of the Status Word-Decode subprogram of FIG. 40. The purpose of this subprogram is to determine and display on display 504 the status of ITGS 10 from the UP-LINK received from ITGS 10 during the Implant Test subprogram of FIG. 40. There are six possible non-failure states in which ITGS 10 can be. If ITGS 10 is in any other state, it is not operating properly.

In this embodiment of the Status Word Decode subprogram, processor 528 tests for each one of the non-failure states in the order shown in FIG. 42. However, processor 528 could test for the non-failure states in any order without changing the results achieved by the Status Word-Decode subprogram. Processor 528 first determines, from the UP-LINK stored in register STATUS-REG, whether or not ITGS 10 is in a first state of "not implanted, 'off', lead hi, battery o.k." If so, processor 528 executes the Implant Test Passed Display subprogram, discussed below in conjunction with FIG. 43, to indicate ITGS 10 is in either the first or second non-failure state. Processor 528 then exits the Status Word Decode subprogram.

If ITGS 10 is not in the first state, processor 528 determines whether or not it is in a second state of "implanted, 'on', lead o k., battery o.k." If so, processor 528 executes the Implant Test Passed Display subprogram to indicate 10 is in either the first or second non-failure state. Processor 528 then exits the Status Word Decode subprogram.

If ITGS 10 is not in the second state, processor 528 determines whether or not it is in a third state of "implanted, 'on' lead o.k., battery lowz". If so, processor 528 executes the Implant Battery Low Display subprogram of FIG. 48 to indicate that the battery powering ITGS 10 is "low". Processor 528 then exits the Status Word Decode subprogram.

If ITGS 10 is not in the third state, processor 528 determines whether or not it is in a fourth state of "not implanted, 'on' lead hi battery o.k.". If so, processor 528 generates and causes transmission of a DOWN-LINK instructing ITGS 10 to turn "off", because allowing ITGS 10 to be "on" when it is not implanted is an unnecessary drain on the ITGS 10 battery. Processor 528 next executes the Read UP-LINK subprogram discussed above in conjunction with FIG. 41, and verifies that ITGS 10 is "off". Processor 528 performs the verification by reading bits STIM0 and STIM1 of the UP-LINK (FIG. 9c). Processor 528 then executes the "On" Warning Display subprogram discussed below in conjunction with FIG. 44 and exits the Status Word Decode subprogram.

If ITGS 10 is not in the fourth state, processor 528 determines whether or not it is in a fifth state of "implanted, 'off' lead o.k., battery low". If ITGS 10 is in the fifth state, processor 528 executes the "Off" Warning Display subprogram, discussed below in conjunction with FIG. 45, to indicate that the implanted ITGS 10 is "off". Processor 528 then exits the Status Word Decode subprogram.

If ITGS 10 is not in the fifth state, processor 528 determines whether or not it is in the last non-failure state of "implanted, 'off' lead o.k., battery low". If ITGS 10 is in this last non-failure state, processor 528 executes the "Off" Warning Display subprogram and then exits the Status Word Decode subprogram.

If ITGS 10 is not in any of the six non-failure states, processor 528 executes a Failure Display subprogram discussed below in conjunction with FIG. 46.

Figure 43:
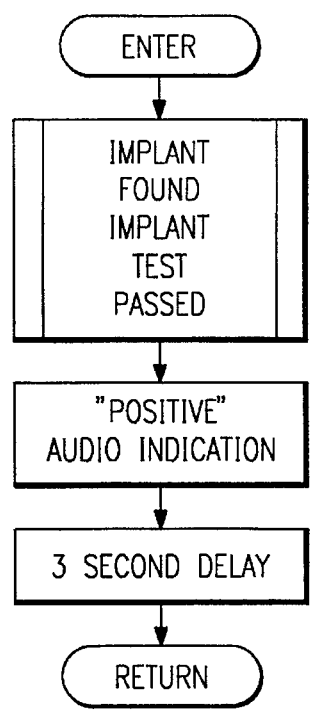
FIG. 43 is a flow chart of the Implant Test Passed Display subprogram of FIG. 42.

FIG. 43 is a flow chart of the Implant Test Passed Display subprogram of FIG. 41. The message "IMPLANT FOUND IMPLANT TEST PASSED" is displayed on display 504. This message indicates that communications with ITGS 10 have been established and that ITGS 10 is functioning properly. A "positive" audio tone is generated by audio tone generator 532 of FIG. 26. The message and the tone are generated for approximately 3 seconds, as shown by the three second delay, before processor 528 exits the subprogram.

Figure 44:
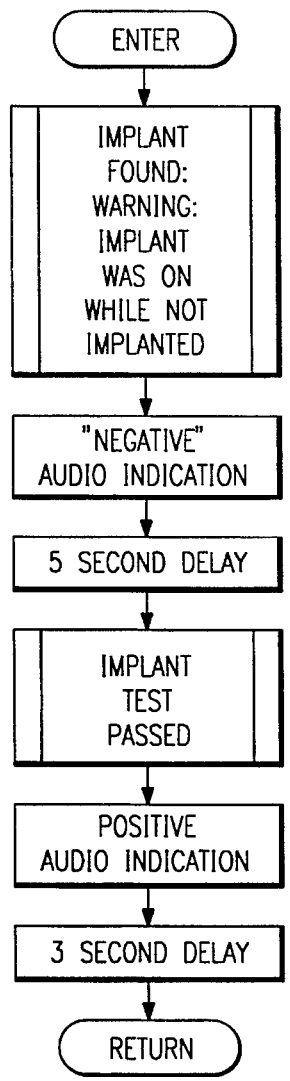
FIG. 44 is a flow diagram of the On Warning Display subprogram of FIG. 42.

FIG. 44 is a flow chart of the "On" Warning Display subprogram of FIG. 42. This subprogram is executed to warn that the non implanted ITGS 10 is "on". Typically, ITGS 10 should be "off" when not implanted to conserve battery power. This warning is to insure that the non implanted ITGS 10 is not inadvertently left "on". The message "IMPLANT FOUND: WARNING: IMPLANT WAS ON WHILE NOT IMPLANTED" is displayed on display 504. Audio tone generator 532 of FIG. 26 generates a "negative" audio tone. Both the message and the tone are generated for approximately 5 seconds as indicated by the 5 second delay. Next, processor 528 instructs display 504 to display the message "IMPLANT TEST PASSED" to indicate ITGS 10 is functioning properly. Audio tone generator 532 generates a "positive" audio tone. Both the message and the tone are generated for approximately 3 seconds as indicated by the 3 second delay. Processor 528 then exits the "On" Warning Display subprogram.

Figure 45:
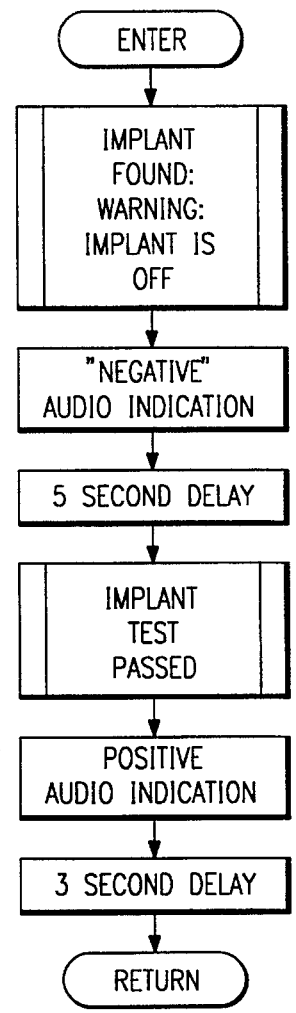
FIG. 45 is a flow chart of the Off Warning Display subprogram of FIG. 42.

FIG. 45 is a flow chart of the "Off" Warning Display subprogram of FIG. 42. This subprogram is executed to warn that the implanted ITGS 10 is "off". Typically, ITGS 10 should be "on" when implanted to promote the healing of a tissue site. This warning is to insure that the implanted ITGS 10 is not inadvertently left "off". Processor 528 instructs display 504 to display the message "IMPLANT FOUND: WARNING: IMPLANT IS OFF". Audio tone generator 532 is instructed by processor 528 to generate a "negative" audio tone. Both the message and the tone are generated for approximately 5 seconds as shown by the 5 second delay. Processor 528 next instructs display 504 to display the message "IMPLANT TEST PASSED" to indicate ITGS 10 is functioning properly. Audio tone generator 532 is instructed to generate a "positive" audio tone. Both the message and the tone are generated for approximately 3 seconds as shown by the 3 second delay. Processor 528 then exits the "Off" Warning Display subprogram.

Figure 46:
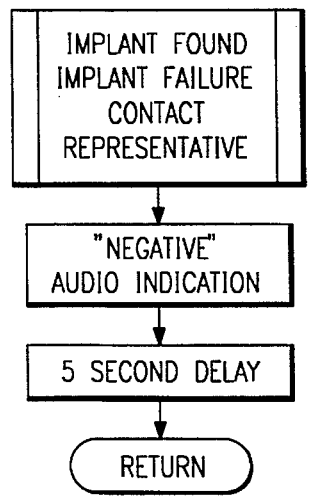
FIG. 46 is a flow chart of the Failure Display subprogram of FIG. 42.

FIG. 46 is a flow chart of the Failure Display subprogram of FIG. 42. The function of this subprogram is to warn that ITGS 10, whether or not it is implanted, is not functioning properly and needs servicing. Processor 528 instructs display 504 to display the message "IMPLANT FOUND IMPLANT FAILURE CONTACT REPRESENTATIVE". Audio tone generator 532 is instructed by processor 528 to generate a "negative" audio tone. Both the message and the tone are generated for approximately 5 seconds, as shown by the 5 second delay. Processor 528 then exits the Failure Display subprogram.

Figure 47:
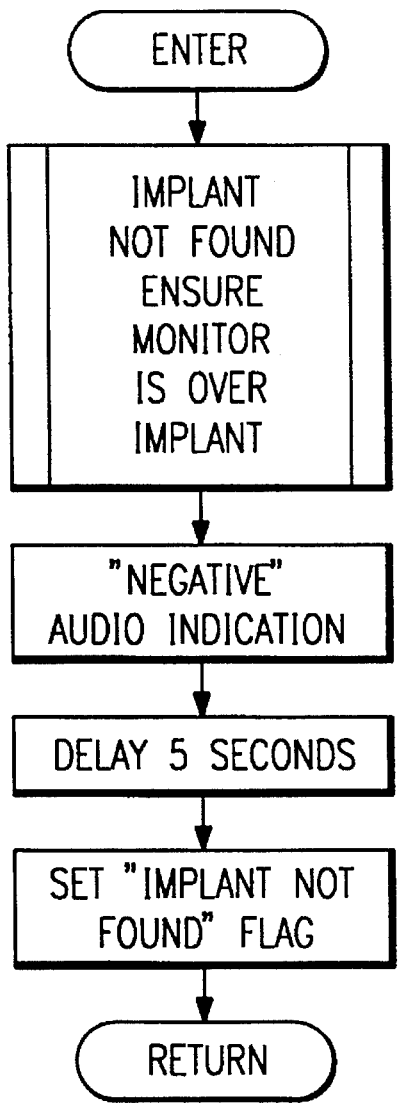
FIG. 47 is a flow chart of the Failure Implant Not Found subprogram of FIG. 41.

FIG. 47 is a flow chart of the Failure Implant Not Found subprogram of FIG. 41. The function of this subprogram is to indicate that communications have not been established between P/M 500 and ITGS 10. Processor 528 instructs display 504 to display the message "IMPLANT NOT FOUND ENSURE MONITOR IS OVER IMPLANT". This message suggests communications may not have been established because antenna housing 501 of P/M 500 is not directly over and facing ITGS 10 or the area in which ITGS 10 is implanted, if it is implanted. Audio generator 532 is instructed by processor 528 to generate a "negative" audio tone. Both the message and the tone are generated for approximately 5 seconds as shown by the 5 second delay. Processor 528 then sets the "Implant Not Found" flag in FLAG-REG and exits the Failure Implant Not Found subprogram.

Figure 48:
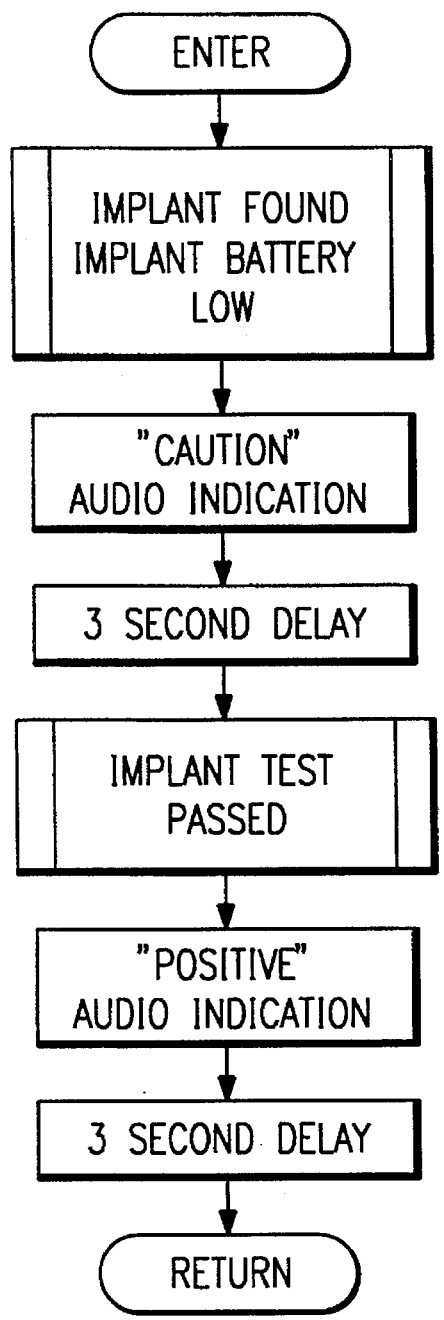
FIG. 48 is a flow chart of the Implant Battery Low Display of FIG. 42.

FIG. 48 is a flow chart of the Implant Battery Low Display subprogram of FIG. 42. The function of this subprogram is to indicate that the ITGS battery is becoming weaker, and will probably need to be replaced soon. The subprogram also indicates that ITGS 10 is functioning properly. Processor 528 instructs display 504 to display the message "IMPLANT FOUND IMPLANT BATTERY LOW". Audio tone generator 532 is instructed by processor 528 to generate a "caution" audio tone. Both the message and the tone are generated for approximately 3 seconds as shown by the 3 second delay. Processor 528 next instructs display 504 to display the message "IMPLANT TEST PASSED". Audio tone generator 532 is instructed by processor 528 to generate a "positive" audio tone. Both the message and the tone are generated for approximately 3 seconds as shown by the 3 second delay. Processor 528 then exits the Implant Battery Low Display subprogram.

In this embodiment, as evident from FIGS. 35–48, messages appear on display 504 of P/M 500 to indicate to a human user the status of both P/M 500 of FIG. 23 and ITGS 10 of FIG. 1. However, in other embodiments, processor 528 may send these status messages to an external device, such as a computer, for further processing as shown in FIGS. 24 and 26. The computer would communicate with processor 528 via port connector 542. In response to these status messages, the computer could issue instructions to P/M 500 via port connector 542 and processor 528. The external computer could also generate and cause transmission of a DOWN-LINK to ITGS 10 via port connector 542, processor 528 and transmit/receive circuit 514.

F. MODIFIED IMPLANTABLE TISSUE GROWTH STIMULATOR

FIG. 49 is an alternative embodiment to the application specific integrated circuit (ASIC) 46 (FIGS. 8a and 8b) of ITGS 10 (FIG. 1). In this embodiment, many of the functions performed by ASIC 46 are now performed by processor 600. ASIC 602 includes additional circuitry for performing additional functions which will be discussed below in detail. All remaining functions are performed in the same way and by the same internal circuitry and structure as discussed in conjunction with FIGS. 8–22.

Processor 600 is reset during power up by power up reset circuit 604, which operates in the same way as power-up reset circuit 50 of FIG. 8a. Crystal oscillator 606 provides a signal which processor 600 converts into an internal timing signal. Memory 608 includes a ROM 610 for storing operating program code for processor 600. Memory 608 also includes RAM 612 for temporary storage of data. RAM 612 includes a register VOLTAGE OUT-REG whose use will be discussed below in greater detail. An address/data bus provides a two-way communications path between processor 600, memory 608 and ASIC 602.

As FIG. 49 shows, the transmit/receive function is performed by microprocessor 600 in conjunction with external circuitry. PPM decoder 614 decodes the PPM signals (FIGS. 9a–c) transmitted between ITGS 10 and P/M 500. The internal circuitry of PPM decoder 614 is similar to that shown in FIG. 11. Transmitter/receiver 618 converts the digital UP-LINK generated by processor 600 via PPM decoder 614 to an analog UP-LINK for driving transmitter/receiver coil 620. Transmitter/receiver coil 620 converts the analog UP-LINK to an electromagnetic UP-LINK for reception by antenna 521 (FIG. 28) of P/M 500. Transmit/receive coil 620 also converts an electromagnetic DOWN-LINK received from P/M 500 into an analog DOWN-LINK suitable for coupling to transmitter/receiver 618. Transmitter/receiver 618 converts the analog DOWN-LINK to a digital DOWN-LINK coupled via PPM decoder 614 to processor 600. Although PPM decoder 614, transmitter/receiver 618 and transmitter/receiver coil 620 are shown in this alternative embodiment as external circuitry, other alternative embodiments may have these components disposed within ASIC 602.

Still referring to FIG. 49, ASIC 602 includes a status/control register 622 for sending status information (UP-LINK) and receiving commands (DOWN-LINK) respectively via processor 600 to and from P/M 500. Output driver circuit 624 drives output terminals with signals OUT1 and OUT2 as does output driver 54 (FIGS. 8b AND 13). However, as will be discussed in detail below in conjunction with FIG. 50, output driver 624 monitors the impedance between electrodes 14 and 16 in AC mode, or between cathodes 30 and anode 28, in DC mode of operation of IRGS 10. This impedance is sent to microprocessor 600 as a sense voltage. Additionally, an analog ground is coupled between ASIC 602 and processor 600. An Analog to Digital Converter (ADC) 626 is included within processor 600 for converting the sense voltage into a digital signal compatible with processor 600.

FIG. 50 is a block diagram of output circuit 624 of FIG. 49. Output circuit 624 includes an output driver controller 628 which sets the amount of current output by output driver 630 in response to a DOWN-LINK received via processor 600 and status/control register 622 from P/M 500. Output driver controller 628 is discussed in more detail below in conjunction with FIG. 49. Differential amplifier 632 senses and amplifies the voltage across cathodes 30 and anode 28 (FIG. 3) in DC mode. In AC mode, Differential Amplifier 632 senses and amplifies the voltages between electrode 14 and $V_g$ and electrode 16 and $V_g$ respectively (FIG. 1). In either mode of operation, the amplified voltage is the sense voltage which is coupled to ADC 626 of processor 600.

Figure 51:
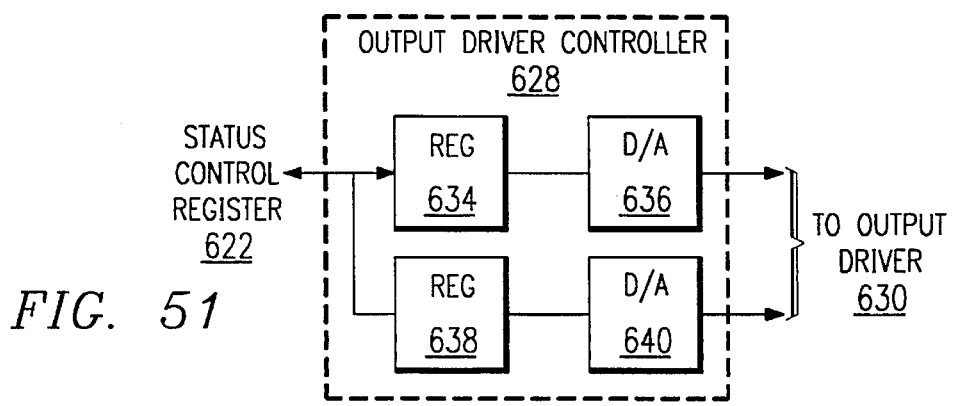
FIG. 51 is a block diagram of the output driver controller of FIG. 50.

FIG. 51 is a block diagram of output driver controller 628 of FIG. 50. A register 634 receives and stores a digital command from status/control register 622. This digital command represents the value of the current to be output from output driver 630. This digital value is then converted into a corresponding voltage by Digital to Analog Converter (DAC) 636. This corresponding voltage is coupled to output driver 630. In response to this analog voltage, output driver 630 sets the current output to the cathode 30 and anode 28 in DC mode, and to electrodes 14 and 16 in AC mode, to the value represented by the digital command.

Still referring to FIG. 51, a register 638 also receives and stores a second digital command from status/control register 622. This second digital command represents the duty cycle of the waveform generated by output driver 630 when ITGS 10 is operating in AC mode (FIG. 1). This second digital command is then converted to a corresponding voltage by DAC 640. In response to the corresponding voltage, output driver 630 generates an output waveform (FIG. 4) with the desired duty cycle.

FIG. 52a shows a modified DOWN-LINK with two additional commands from the DOWN-LINK of FIG. 9b. The command "Write Current" indicates the DOWN-LINK contains the value for the current to be loaded into register 638 of FIG. 51. The "Write Duty Cycle" command (only used in AC mode) indicates the DOWN-LINK contains the value for the duty cycle to be loaded into register 634 of FIG. 51. To accommodate the two additional commands, the size of the DOWN-LINK must be increased by one bit from 11 bits to 12 bits. The Read Not Write commands (shown here as "Write" and "Read") remain the same as in FIG. 9b.

FIGS. 52b–c show the two additional UP-LINKs required for the operation of the modified ITGS 10. The first UP-LINK, remains identical to that shown in FIG. 9c. The second, UP-LINK2, provides voltage-out, the contents of VOLTAGEOUT-REG, i.e., the impedance measurement, to P/M 500. The third, UP-LINK3 (used in AC mode only), provides the Duty-Cycle contents of register 638, i.e., the current duty cycle of the output waveform. UP-LINK1 is transmitted immediately after UP-LINK2. When ITGS 10 is operating in AC mode, UP-LINK3 is transmitted immediately after UP-LINK2. The Read UP-LINK subprogram of FIG. 41 is modified slightly in that all three UP-LINKs are read twice as a group of three, and the first group is compared to the second group for verification of error free reception.

1. Circuit Operation

In operation, registers 634 and 638 of FIG. 51 are loaded with predetermined values by microprocessor 600 upon power up of ITGS 10 (FIG. 1). This results in a predetermined current amplitude during both AC and DC operation, and a predetermined duty cycle in AC operation. The current and duty cycle characteristics of the waveform are collectively called the "burst pattern" of the waveform.

During AC operation, differential amplifier 632 of FIG. 50 alternately provides, as the second voltage, the voltage differences between terminal OUT1 and Vg then between OUT2 and Vg, and depending upon which terminal is presently providing output current at the time. In this embodiment, OUT1 provides current during the positive going portions of the waveform of FIG. 4, and OUT2 provides current during the negative going portions of the same waveform, the same as output driver 54 of FIGS. 8b and 13.

ADC 626 of processor 600 in FIG. 49 receives the sense voltage and continually converts it into a digital word. Processor 600 continually updates register VOLTAGEOUT-REG in RAM 612 with the most recent of these digital words. Only the most recent contents of register VOLTAGEOUT-REG is needed to compute the impedance between the electrodes 14 and 16.

Figure 53:
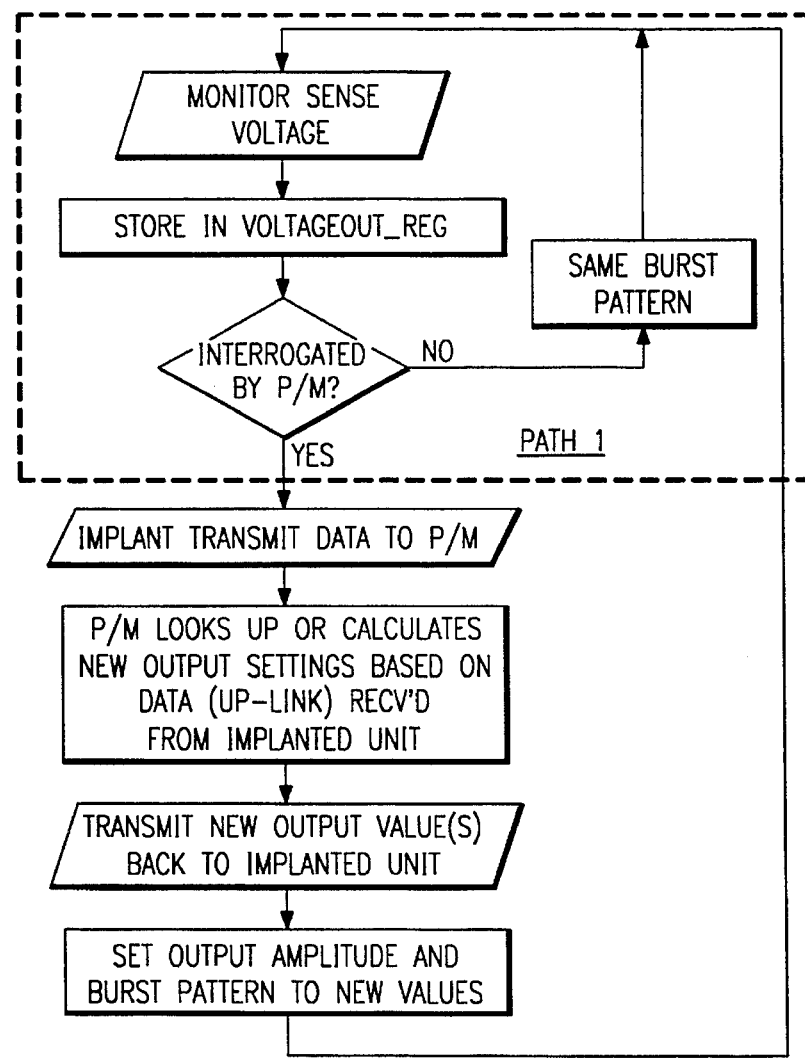
FIG. 53 is a flow diagram of the Set Burst Pattern subprogram executed in conjunction with the alternative embodiment of FIG. 49.

During DC operation, differential amplifier 632 provides, as the sense voltage, the voltage difference between terminal OUT1 and terminal OUT2. The impedance calculated is, therefore, that between cathodes 30 and anode 28. The remaining function is identical to that as described above for AC operation. Path 1 of the flow chart of FIG. 53 summarizes this process for both the AC and DC modes of operation.

2. Interactive Programming/Monitoring of Modified Implantable Tissue Growth Stimulator At an arbitrary time later, P/M 500 "interrogates" ITGS 10 for the measurement stored in register VOLTAGEOUT-REG, as shown in the flow chart of FIG. 53. ITGS 10 then transmits this measurement to P/M 500. In response to this received measurement, programmer/monitor 500 may generate a DOWN-LINK representing a new current setting for ITGS 10. If ITGS 10 is operating in AC mode, P/M 500 may generate a DOWN-LINK representing a new duty cycle setting. The DOWN-LINK containing the new current setting is transmitted to ITGS 10 and loaded into register 634. The DOWN-LINK containing the new duty cycle setting is transmitted to ITGS 10 and loaded into register 638 (AC mode only). Output driver 630 then sets the burst pattern (current in DC mode, current and duty cycle in AC mode) of the waveform at OUTPUT1 and OUTPUT2 to the new values.

Although the present invention and its advantages have been described in detail, it should be understood that various changes, substitutions and alterations can be made therein without departing from the spirit and scope of the invention as defined by the appended claims.

What is claimed is:

1. A remote unit for controlling and monitoring an implantable tissue growth stimulator via a two-way wireless communications protocol, the remote unit comprising:

a control circuit having means for generating a down-link message to be transmitted to the stimulator and for decoding an up-link message from the stimulator; and a transmit/receive circuit coupled to and in communication with said control circuit;

said transmit/receive circuit having a pulse generator coupled to receive said down-link message from said control circuit;

said transmit/receive circuit further including a transmit coil coupled to an output of said pulse generator having means for transmitting said down-link message to the stimulator;

said transmit/receive circuit further including a receive coil for receiving said up-link message from the stimulator; and a power circuit, coupled to and in communication with said control circuit and said transmit/receive circuit, said power circuit having means for powering down the remote unit when a down-link message is not generated for a predetermined period of time.

2. The remote unit of claim 1 further comprising a display, coupled to and in communication with said control circuit, for displaying a status of the stimulator, decoded from said up-link message, in response to a display signal from said control circuit.

3. The remote unit of claim 1 further comprising:

an input device, coupled to and in communication with said control circuit, having means for providing data to said control circuit; and wherein said control circuit generates said down-link message in response to said data.

4. The remote unit of claim 3, said control circuit further comprising means for generating a disable Signal so as to disable the receive coil when the remote unit is transmitting said down-link message.

5. The remote unit of claim 3 further comprising:

a display, coupled to and in communication with said control circuit, having means for displaying a plurality of data choices; and wherein said input device is activated to select said data from said data choices.

6. The remote unit of claim 1 wherein said control circuit comprises:
 a processor having means for executing an interactive program for generating said down-link message and for decoding said up-link message; and
 a memory, coupled to and in communication with said processor, having means for storing said interactive program.

7. The remote unit of claim 1 further comprising a data port coupled to said control circuit, said data port having means for providing a communication pathway between said control circuit and an external device.

8. A remote control unit for programming and monitoring an implantable tissue growth stimulator having a status via a two-way wireless communications protocol, the remote control unit comprising:
 a processor having means for executing an interactive program for converting a stimulator instruction into a down-link signal in response to choice selection data, for generating at least one choice prompt, and for decoding the status of the stimulator from an up-link signal;
 a memory, coupled to and in communication with said processor, having means for storing said interactive program;
 a display, coupled to and in communication with said processor, having means for displaying said choice prompt and the status of the stimulator;
 an input device, coupled to and in communication with said processor, having means for receiving said choice selection data and providing said choice selection data to said processor; and
 a transmit/receive circuit coupled to and in communication with said processor;
 said transmit/receive circuit having a pulse generator coupled to receive said down-link signal from said processor, said pulse generator having an output;
 said transmit/receive circuit further including a transmit coil coupled to an output of said pulse generator having means for transmitting said down-link signal to the stimulator;
 said transmit/receive circuit further including a receive coil for receiving said up-link signal from the stimulator; and
 a power circuit, coupled to and in communication with said processor, said memory, said display, said input device and said transmit/receive circuit, said power circuit having means for powering down the remote control unit when said choice selection data is not provided by said input device for a predetermined period of time.

9. The remote control unit of claim 8 said processor further comprising means for generating a disable signal so as to disable the receive coil when the remote control unit is transmitting said down-link signal.

10. The remote control unit of claim 8 wherein said display is divided into first and second portions, said first portion having means for displaying a first choice prompt and said second portion having means for displaying a second choice prompt.

11. The remote control unit of claim 10 wherein said input device comprises a first selector corresponding to said first portion of said display and a second selector corresponding to said second portion of said display, and wherein said first selector is activated to provide choice selection data indicated by said first choice prompt to said processor and said second selector is activated to provide choice selection data indicated by said second choice prompt to said processor.

12. The remote control unit of claim 8 further comprising:
 a housing with a hollow interior having disposed therein said processor, said memory, said display, said input device and said transmit/receive circuit.

13. The remote unit of claim 8 wherein said processor further comprises means for converting said stimulator instruction into said down-link signal, said stimulator instruction for commanding a power circuit disposed within the growth stimulator to provide power to the growth stimulator.

14. The remote unit of claim 8 wherein said processor further comprises means for converting said stimulator instruction into said down-link signal, said stimulator instruction commanding a driver controller disposed within the growth stimulator to set to a predetermined value the amplitude of a waveform generated by the growth stimulator.

15. The remote unit of claim 8 wherein said processor further comprises means for converting said stimulator instruction into said down-link signal, said stimulator instruction commanding a driver controller disposed within the growth stimulator to set to a predetermined value a duty cycle of a waveform generated by the growth stimulator.

16. The remote unit of claim 8 wherein said processor further comprises means for determining from the stimulator status a condition of a battery powering the growth stimulator.

17. The remote unit of claim 8 wherein said processor further comprises means for determining from the stimulator status a impedance between a pair of output leads across which the stimulator generates a waveform.

18. The remote unit of claim 8 wherein said processor further comprises means for determining from the stimulator status whether a power circuit disposed within the growth stimulator is providing power to the growth stimulator.

19. The remote unit of claim 8 wherein said processor further comprises means for determining from the stimulator status a mode in which the growth stimulator is operating.

20. The remote unit of claim 8 wherein said processor further comprises means for determining from the stimulator status a duty cycle of a waveform generated by the growth stimulator.

21. The remote unit of claim 8 wherein said processor further comprises means for determining from the stimulator status a amplitude of a waveform generated by the growth stimulator.

22. The remote unit of claim 8 wherein said processor further comprises means for testing said memory, display, input device and transmit/receive circuit for proper functioning.

23. The remote unit of claim 8 further comprising an audio tone generator, coupled to and in communication with said processor, for generating an audible tone associated with the stimulator status in response to a signal from said processor.

24. A method for programming an implantable tissue growth stimulator and for monitoring a status of the stimulator with a remote control unit via a two-way communication protocol, the method comprising the steps of:
 providing data from an input device to a control circuit, said control circuit coupled to said input device;
 generating a down-link message in response to said data;

transmitting said down-link message to the stimulator with a transmit coil of a transmit/receive circuit coupled to said control circuit;

receiving an up-link message with a receive coil of said transmit/receive circuit;

providing said received up-link message to said control circuit;

decoding said up-link message with said control circuit; and powering down the remote control unit when said data is not received from said input device for a predetermined period of time.

25. The method of claim 24 further comprising the steps of:

decoding the status of the growth stimulator from said up-link message with said control circuit;

displaying the stimulator status on a display coupled to said control circuit in response to a signal from said control circuit.

26. The method of claim 24 further comprising the step of disabling said receive coil when said transmit coil transmits a down-link message.

27. The method of claim 24 further comprising the steps of:

displaying a plurality of data choices on a display coupled to said control circuit; and selecting said data from said data choices with said input device.

28. The method of claim 24 further comprising the steps of:

executing with a processor of said control circuit an interactive program for generating said down-link message and for decoding said up-link message; and storing said interactive program in a memory coupled to said processor.

29. The method of claim 24 further comprising the step of providing a communication pathway between said control circuit and an external device with a data port circuit coupled to said control circuit.

30. A system for therapeutic stimulation of a tissue site comprising:

an implantable tissue growth stimulator having a status, said stimulator including, first and second plate electrodes, having first and second voltages respectively, for subcutaneous implantation at a predetermined distance from the tissue site, a thin elongate member of elastomer for generally maintaining a predetermined distance between said first and second electrodes;

a driver coupled to said first and second plate electrodes having means for generating an alternating current between said first and second electrodes, said alternating current operative to stimulate tissue growth at the tissue site, a receiver coupled to said driver for receiving a down-link signal, and a transmitter coupled to said drive having means for transmitting an up-link signal; and a remote unit for programming and monitoring the stimulator via a two-way communication protocol, the remote unit including, a control circuit having means for converting a stimulator instruction into said down-link signal and for decoding said status from said up-link signal, and a transmit/receive circuit, coupled to and in communication with said control circuit, having means for transmitting said down-link to said stimulator and for receiving said up-link from said stimulator.

31. The system of claim 30 wherein said remote unit further comprises a display, coupled to and in communication with said control circuit, having means for displaying said status in response to a display signal from said control circuit.

32. The system of claim 30 wherein said remote unit further comprises:

an input device, coupled to and in communication with said control circuit, having means for providing data to said control circuit; and wherein said control circuit converts said stimulator instruction into said down-link signal in response to said data.

33. The system of claim 32 wherein said remote unit further comprises:

a display, coupled to and in communication with said control circuit, having means for displaying a plurality of data choices; and wherein said input device is activated to select said data from said data choices.

34. The system of claim 30 wherein said control circuit comprises:

a processor having means for executing an interactive program for converting said instruction into said down-link signal and for decoding said status from said up-link signal; and a memory, coupled to and in communication with said processor, having means for storing said interactive program.

35. The system of claim 30 wherein said implantable tissue growth stimulator further comprises:

a decoder, coupled to and in communication with said receiver, having means for decoding said stimulator instruction from said down-link; and a driver controller, coupled in and in communication with said decoder, having means for adjusting a parameter of said alternating current in response to said stimulator instruction.

36. The system of claim 35 wherein said driver controller further comprises means for adjusting a duty cycle of said alternating current in response to said stimulator instruction.

37. The system of claim 35 wherein said driver controller further comprises means for adjusting a amplitude of said alternating current in response to said stimulator instruction.

38. The system of claim 30 wherein said implantable tissue growth stimulator further comprises a modem circuit, coupled to and in communication with said transmitter, having means for converting said status into said up-link signal.

39. The system of claim 38 wherein said modem circuit further comprises means for converting said status into said up-link signal in response to said down-link signal.

* * * * *